United States Patent
Galagan et al.

(10) Patent No.: US 11,801,000 B2
(45) Date of Patent: Oct. 31, 2023

(54) HORMONE ELECTROCHEMICAL BIOSENSOR

(71) Applicant: Trustees of Boston University, Boston, MA (US)

(72) Inventors: James Galagan, Needham, MA (US); Uros Kuzmanovic, Brookline, MA (US); Abdurrahman Addokhi, Cambridge, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 17/734,042

(22) Filed: Apr. 30, 2022

(65) Prior Publication Data

US 2022/0361782 A1 Nov. 17, 2022

Related U.S. Application Data

(60) Provisional application No. 63/182,169, filed on Apr. 30, 2021.

(51) Int. Cl.
| | |
|---|---|
| *A61B 5/145* | (2006.01) |
| *A61B 5/1477* | (2006.01) |
| *A61B 5/1486* | (2006.01) |

(52) U.S. Cl.
CPC ........ *A61B 5/14546* (2013.01); *A61B 5/1451* (2013.01); *A61B 5/1477* (2013.01); *A61B 5/1486* (2013.01); *A61B 5/14517* (2013.01)

(58) Field of Classification Search
CPC .............. A61B 5/14546; A61B 5/1451; A61B 5/14517; A61B 5/1477; A61B 5/1486; C12Q 1/002; C12Q 1/001

See application file for complete search history.

(56) References Cited

U.S. PATENT DOCUMENTS

| | | |
|---|---|---|
| 6,241,863 B1 | 6/2001 | Monbouquette |
| 6,605,200 B1 | 8/2003 | Mao et al. |
| 6,736,777 B2 | 5/2004 | Kim et al. |
| | (Continued) | |

FOREIGN PATENT DOCUMENTS

| | | |
|---|---|---|
| CN | 102053161 A | 5/2011 |
| CN | 105136885 A | 12/2015 |
| | (Continued) | |

OTHER PUBLICATIONS

D'Arcy, B.M., Swingle, M.R., Schambeau, L. et al., "Development of a Synthetic 3-ketosteroid Δ1-dehydrogenase for the Generation of a Novel Catabolic Pathway Enabling Cholesterol Degradation in Human Cells", Sci Rep 9, 5969 (2019) (Year: 2019).*

(Continued)

*Primary Examiner* — Matthew Kremer
*Assistant Examiner* — Kyle W. Kretzer
(74) *Attorney, Agent, or Firm* — Burns & Levinson LLP; Steven M. Mills

(57) ABSTRACT

Disclosed is a hormone electrochemical biosensor, e.g. an amperometric biosensor, for the detection of a hormone and measurement of the concentration of a hormone. The disclosed hormone biosensor comprises a hormone-catalyzing enzyme, such as KSDH1. Also described herein are systems comprising an amperometric biosensor, e.g., chronoamperometric biosensor and methods of using the chronoamperometric biosensor.

22 Claims, 47 Drawing Sheets

Specification includes a Sequence Listing.

(56) References Cited

U.S. PATENT DOCUMENTS

| | | | |
|---|---|---|---|
| 7,794,994 | B2 | 9/2010 | Cranley et al. |
| 9,820,692 | B2 | 11/2017 | Wang et al. |
| 10,182,795 | B2 | 1/2019 | Heikenfeld et al. |
| 10,646,142 | B2 | 5/2020 | Heikenfeld et al. |
| 11,331,020 | B2 | 5/2022 | Galagan et al. |
| 2003/0027239 | A1 | 2/2003 | Schaffar |
| 2008/0057528 | A1 | 3/2008 | Sayre et al. |
| 2008/0160625 | A1 | 7/2008 | Palleschi et al. |
| 2009/0061451 | A1 | 3/2009 | Shi et al. |
| 2009/0099434 | A1 | 4/2009 | Liu et al. |
| 2011/0033869 | A1 | 2/2011 | Bertin |
| 2012/0088258 | A1* | 4/2012 | Bishop ............... A61B 5/14532 435/7.1 |
| 2012/0181189 | A1 | 7/2012 | Merchant |
| 2013/0172705 | A1 | 7/2013 | Petillo et al. |
| 2015/0260674 | A1 | 9/2015 | Tsao |
| 2019/0004005 | A1* | 1/2019 | Oja .................... G01N 27/3277 |
| 2019/0153403 | A1 | 5/2019 | Xu et al. |
| 2019/0195894 | A1* | 6/2019 | Galagan ................ C07K 14/34 |
| 2021/0259585 | A1 | 8/2021 | Galagan et al. |

FOREIGN PATENT DOCUMENTS

| | | |
|---|---|---|
| CN | 107058444 A | 8/2017 |
| CN | 110573868 A | 12/2019 |
| EP | 1194585 A2 | 4/2002 |
| EP | 1845371 A1 | 10/2007 |
| WO | 0100865 A2 | 1/2001 |
| WO | 2005048834 A1 | 6/2005 |
| WO | 2013059534 A1 | 4/2013 |
| WO | 2017210465 A1 | 12/2017 |
| WO | 2018144879 A1 | 8/2018 |
| WO | 2018202793 A2 | 11/2018 |
| WO | 2019204485 A1 | 10/2019 |
| WO | 2019224628 A1 | 11/2019 |
| WO | 2021158973 A1 | 8/2021 |

OTHER PUBLICATIONS

Grazon C, Baer RC, Kuzmanović U, Nguyen T, Chen M, Zamani M, Chern M, Aquino P, Zhang X, Lecommandoux S, Fan A, Cabodi M, Klapperich C, Grinstaff MW, Dennis AM, Galagan JE, "A progesterone biosensor derived from microbial screening", Nat Commun, Mar. 9, 2020 (Year: 2020).*

R. Cooper Baer, "Discovery, characterization, and ligand specificity engineering of a novel bacterial transcription factor inducible by progesterone", Jun. 1, 2020 (Year: 2020).*

Ainla et al., "Open-Source Potentiostat for Wireless Electrochemical Detection with Smartphones," Analytical Chemistry, 2018, 90, pp. 6240-6246, DOI: 10.1021/acs.analchem.8b00850.

Ang et al., "Study of Different Molecular Weights of Chitosan as an Immobilization Matrix for a Glucose Biosensor," PLoS One, Aug. 5, 2013, 8(8):e70597.

Apilux et al., "Paper-Based Immunosensor with Competitive Assay for Cortisol Detection," J. Pharm. Biomed. Anal. 178, 112925, doi:10.1016/j.jpba.2019.112925 (2020) 7 pages.

Arugula et al., "Novel Trends in Affinity Biosensors: Current Challenges and Perspectives," Measurement Science and Technology, 2014, 25(3), 032001, 22 pages.

Attili et al., "A Piezoelectric Immunosensor for the Detection of Cortisol," Annl. Lett. 28, 2149-2159, doi:10.1080/00032719508000035 (1995).

Bataillard et al., "An Integrated Silicon Thermopile as Biosensor for the Thermal Monitoring of Glucose, Urea, and Penicillin," Biosen. Bioelect. 8:89-98 (1993).

Bauer et al., "A Genetic Enrichment for Mutations Constructed by Oligodeoxynucleotide-Directed Mutagenesis," Gene 37 (1985), pp. 73-81.

Carlson et al., "An Automated Handheld Biosensor for Aflatoxin," Biosens. Bioelectr. 14:841 (2000).

Choi et al., "Real-Time Measurement of Human Salivary Cortisol for the Assessment of Psychological Stress Using a Smartphone," Sensing and Bio-Sensing Research 2, 8-11 (2014).

Craik, "Use of Oligonucleotides for Site-Specific Mutagenesis," Bio Technologies, Jan. 1985, pp. 12-19.

Dexter et al., "Development of a Bioluminescent ATP Assay to Quantify Mammalian Bacterial Cell Number from a Mixed Population," Biomaterials, 2003, 24:27-34.

Diaz-Gonzale et al., "Recent Advances in Electrochemical Enzyme Immunoassays," Electroanalysis 17, 2005, No. 21, pp. 1901-1918.

Dodeigne et al., "Chemiluminescence as a Diagnostic: A Review," Talanta 2000, 51:415-439.

Fahnrich et al., "Recent Applications of Electrogenerated Chemiluminescence in Chemical Analysis," Talanta, 2001, 54:531-59.

Ferri et al., "Review of Glucose Oxidases and Glucose Dehydrogenases: A Bird's Eye View of Glucose Sensing Enzymes," SAGE Publications, 2011.

Frenzel et al., "Expression of Recombinant Antibodies," Frontiers in Immunology, 2013,4, 217.

Ganguly et al., "A Combinatorial Electrochemical Biosensor for Sweat Biomarker Benchmarking," SLAS Technol., 25, pp. 25-32, doi:10.1177/2472630319882003 (2020).

Gschwend et al., "Optical Detection of Mitochondria NADH Content in Intact Human Myotubes," Cell. Mol. Biol. 47:OL95-104 (2001).

Haggstrom et al., "Diagram of the Pathways of Human Steroidogenesis," Wikiversity Journal of Medicine, 2014 1(1), doi:10.15347/wjm/2014.005.

Hornsby et al., "A High Through-Put Platform for Recombinant Antibodies to Folded Proteins," Molecular & Cellular Proteomics, MCP.2015, 14(10), 2833-27.

Jo et al., "Localized Surface Plasmon Resonance Aptasensor for the Highly Sensitive Direct Detection of Cortisol in Human Saliva," Sensors and Actuators:B—Chemical 304, 127424, 8 pages, doi:12742410.1016/j.snb.2019.127424, 2020.

Kaushik et al., Recent Advances in Cortisol Sensing Technologies for Point-of-Care Application, Biosens Bioelectron 53, 499-512, doi:10.1016/j.bios.2013.09.060 (2014).

Kinnamon et al., "Portable Biosensor for Monitoring Cortisol in Low-Volume Perspired Human Sweat," Sci Rep 7, 13312, doi:10.1038/s41598-017-13684-7 (2017).

Leca et al., "Screen Printed Electrodes as Disposable or Reusable Optical Devices for Luminol Electrochemiluminescence," Sens Actuat. B, 2001, 74:190-193.

Lee et al., "A Pharmacokinetic Model of a Tissue Implantable Cortisol Sensor," Adv Healthcare Materials 5, 3004-3015, doi:10.1002/adhm.201600650 (2016).

Loew et al., "Mediator Preference of Two Different FAD-Dependent Glucose Dehydrogenases Employed to Disposable Enzyme Glucose Sensors," Sensors, 2017, 17(11):2636.

Lv, "Chemiluminescence Biosensor Chip Based on a Microreactor Using Carrier Airflow for Determination of Uric Acid in Human Serum," Analyst 2002, 127:1176-1179.

Marrazza, "Aptmer Sensors," Biosensors (Basel) 2017, (75), 3 pages.

Muehlbauer et al., "Model for a Thermoelectric Enzyme Glucose Sensor," Anal. Chem. 61:77-83 (1989).

Mugo et al., "Flexible Molecularly Imprinted Electrochemical Sensor for Cortisol Monitoring in Sweat," Anal Bioanal Chem 412, 1825-1833, doi:10.1007/500216-020-02430-0 (2020).

Pasha et al., Electrochemical Immunosensing of Saliva Cortisol,: Journal of the Electrochemical Society 161(2), B3077-B3082 (2014).

Pires et al., "Measurement of Salivary Cotisol by a Chemiluminescent Organic-Based Immunosensor," Biomed Mater Eng 24, 15-20, doi:10.3233/BME-130778 (2014).

Ramanathan et al., "Principles and Applications of Thermal Biosensors," Biosens Bioelectr. 16:417-4223 (2001).

Rice et al., "CortiWatch—Watch-Based Cortisol Tracker," Future SCI OA 5, FSO416,doi:10.2144/fsoa-2019-0061 (2019).

(56) References Cited

OTHER PUBLICATIONS

Roberts et al., "Comparison of Electrode Materials for the Detection of Rapid Hydrogen Peroxide Fluctuations Using Background-Subtracted Fast Scan Cyclic Voltammetry," Analyst, 2011; 1136, pp. 3550-3556.
Schneckenberger et al., Time-Gated Microscopic Imaging and Spectroscopy in Medical Diagnosis and Photobiology: Opt. Eng. 33:2600-2666 (1994).
Sekar et al., "Carbon Fiber Based Electrochemical Sensor for Sweat Cortisol Measurement," Sci Rep 9, 403, doi:10.1038/s41598-018-37243-w (2019).
Shiwaku et al., "A Printed Organic Circuit System for Wearable Amperometric Electrochemical Sensors," Scientific Reports (2018) 8:6368, DOI: 10.1038/s41598-018-24744-x (8 pages).
Singh et al., "Electrochemical Sensing of Cortisol: A Recent Update," Appl Biochem Biotechnol 174, 1115-1126, (2014), doi:10.1007/s12010-014-0894-2.
Sooner et al., "The Microfluidics of the Eccrine Sweat Gland, including Biomarker Partitioning, Transport, and Biosensing Implications," Biomicrofluidics 9, 031301, 2015, doi:10.1063/1.4921039.
Steinberg et al., "A Wireless Potentiostat for Mobile Chemical Sensing and Biosensing," Talanta 143, 2015, pp. 178-183.
Stevens et al., "Detection of Cortisol in Saliva with a Flow-Filtered, Portable Surface Plasmon Resonance Biosensor System," Anal Chem 80, pp. 6747-6751, 2008, doi:10.1021/ac800892h.
Teepoo et al., "Electrospun Chitosan-Gelatin Biopolymer Composite Nanofibers for Horseradish Peroxidase Immobilization in a Hydrogen Peroxide Biosensor," Biosensors(Basel), Oct. 15, 2017; 7(4). pii:E47.
Torrente-Rodriguez et al., "Investigation of Cortisol Dynamics in Human Sweat Using a Graphene-Based Wireless Health System," Matter 2020.
Tsuruoka et al., "Bimolecular Rate Constants for FAD-Dependent Glucose Dehydrogenase from Aspergillus Terreus and Organic Electron Acceptors," International Journal of Molecular Sciences, 18(3):604, 2017.
Turner, "Biosensors: Then and Now," Trends in Biotechnology 31(3); pp. 119-120, 2013.
Turner et al., "Biosensors: Sense and Sensibility," Chem Soc Rev., 42(8):3184-96, Apr. 21, 2013.
Uygun et al., "Non-Invasive Cortisol Detection in Saliva by Using Molecularly Cortisol Imprinted Fullerene-Acrylamide Modified Screen Printed Electrodes," Talanta 206, 120225, 2020, doi:10.1016/j.talanta.2019.120225.
Vasudev et al., "An LTCC-Based Microfluidic System for Label-Free, Electrochemical Detection of Cortisol," Sensors and Actuators B—Chemical 182, pp. 139-146, 2013, doi:10.1016/j.snb.2013.02.096.
Ventura et al., "Cortisol Extraction Through Human Skin by Reverse Iontophoresis," Bioelectrochemistry, 114, 56-60, 2017, doi:10.1016/j.bioelechem.2016-12-004.
Venugopal et al., "A Realtime and Continuous Assessment of Cortisol in ISF Using Electrochemical Impedance Spectroscopy," Sensors and Actuators a—Physical, 172, pp. 154-160, 2011, doi:10.1016/j.sna.2011.04.028.
Vigneshvar et al., "Recent Advances in Biosensor Technology for Potential Applications—An Overview," Front Bioeng Biotechnol., 4:11, 2016, (9 pages).
Walder et al., "Oligodeoxynucleotide-Directed Mutagenesis Using the Yeast Transformation System" Gene, 42, pp. 133-139, 1986.
Wang et al., "Co-Immobilization of Polymeric Luminol, Iron (11)tris)5-Aminopheanthroiline) and Glucose Oxidase at an Electrode Surface, and Its Application as a Glucose Optrode," Analyst, 127:1507-1511, 2002, doi:10.1039/b203006n.
Willemsen et al., "Use of Specific Bioluminescence Cell Lines for Detection of Steroid Hormon [ani]agonists in Meat Producing Animals," Anal. Chim. Acta, 2002, 473:119-126.
Xie et al., "Development of a Thermal Micro-Biosensor Fabricated on a Silicon Chip," Sens. Actuat. B, 1992, 6:127-130.
Xie et al., "Fast Determination of Whole Blood Glucose with a Calorimetric Micro-Biosensor," Sens. Actuat. B, 1993, 15-16:141-144.
Xu et al., "Reusable Amperometric Immunosensor for the Determination of Cortisol," Analytical Letters, 1997, 30, 2675-2689, doi:10.1080/00032719708001813.
Kumar et al., "Ultrasensitive Detection of Cortisol with Enzyme Fragment Complementation Technology Using Functionalized Nanowire," Biosensors & Bioelectronics, 2007, 22, 2138-2144, doi:10.1016/j.bios.2006.09.035.
Hosu et al., Colorimetric multienzymatic smart sensors for hydrogen peroxide, glucose and catechol screening analysis. Talanta. Nov. 1, 2019;204:525-532. doi: 10.1016/j.talanta.2019.06.041. Epub Jun. 12, 2019.
Danielsson B. Enzyme thermistor devices. Bioprocess Technol. 1991;15:83-105.
International Preliminary Report on Patentability in Application No. PCT/US2021/016894, dated Jul. 28, 2022 (14 pgs.).
Thisted et al., "Optimization of a Nicotine Degrading Enzyme for Potential Use in Treatment of Nicotine Addiction," BMC Biotechnology, vol. 19, article 56, pp. 1-16 (Aug. 2, 2019).
D'Arcy et al., "Development of a Synthetic 3-ketosteroid delta1-dehydrogenase for the Generation of a Novel Catabolic Pathway Enabling Cholesterol Degradation in Human Cells," Scientific Reports, vol. 9, No. 1, Article No. 5969, pp. 1-17 (2019).
Invitation to Pay Additional Fees in PCT/US22/27170, dated Jul. 22, 2022 (3 pgs.).
International Search Report and Written Opinion in Application No. PCT/US22/27170, dated Sep. 27, 2022 (15 pps.).

* cited by examiner

| Enzyme | $K_M$ | $K_{cat}$ (s$^{-1}$) | $1/k_{cat}$ (s) | $k_{cat}/K_M$ (s$^{-1}$mM$^{-1}$) |
|---|---|---|---|---|
| Glucose oxidase (GO$_x$) | 33 - 110 mM | 1118.81 | 0.000894 | 22.04 |
| Lactate oxidase (LO$_x$) | 0.94 mM | 280 | 0.00357 | 297.87 |
| Nicotine oxidoreductase (NicA2)[1] | 43.5 ± 4.7 nM | (6.64 ± 0.17) * 10$^{-3}$ | 150.6024 | 152.64 |
| 3-ketosteroid-Δ1-dehydrogenase (KSDH1) vs Cortisol | 1182 μM | 14.99 | 0.0667 | 12.68 |
| 3-ketosteroid-Δ1-dehydrogenase (KSDH1) vs Progesterone | 97.85 μM | 5.07 | 0.197 | 51.81 |

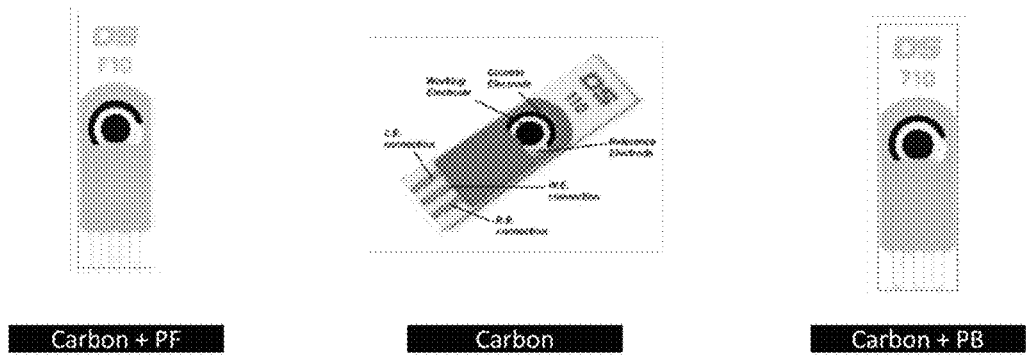
FIG. 14A
FIG. 14B
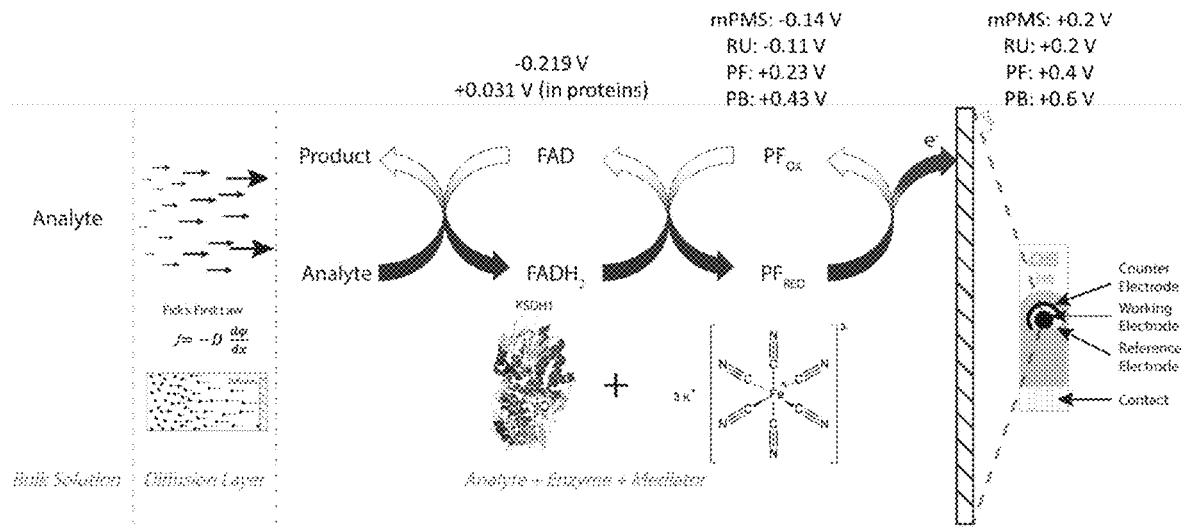
FIG. 15

HORMONE ELECTROCHEMICAL BIOSENSOR

CROSS-REFERENCE TO RELATED APPLICATION

This application claims benefit under 35 U.S.C. § 119(e) of U.S. Provisional Application No. 63/182,169, filed Apr. 30, 2021, the contents of which are incorporated herein by reference in their entirety.

GOVERNMENT SUPPORT

This invention was made with government support under Contract No. TTW-27-9661 awarded by the Uniformed Services University of the Health Sciences. The Government has certain rights in the invention.

SEQUENCE LISTING

The instant application contains a Sequence Listing which has been submitted electronically in ASCII format and is hereby incorporated by reference in its entirety. The ASCII copy, created Apr. 29, 2022, is named BU2020-085_SL.txt and is 7,000 bytes in size.

TECHNICAL FIELD

The technology described herein relates to enzyme-based electrochemical hormone biosensors.

BACKGROUND

The advent of rapid, facile sensing is changing daily life and empowering clinical decision making. The Fitbit™ and Apple Watch™ for monitoring pH, hydration, temperature, heart rate, oxygen, etc., and glucose sensors for managing type 2 diabetes are prime examples. However, enzymatic electrochemical based sensors are few in number and limited in analyte scope (e.g., glucose, fructose, lactate, glutamate, lysine, ethanol), despite the fact that the glucose sensor was developed/discovered approximately 60 years ago. Given the interest in sensing varied analytes for applications in medicine, health/nutrition, agriculture, and environmental management, there is need to develop new sensor designs and diagnostic technologies both for single use detection and for continuous monitoring.

Hormones are one such analyte of interest, is present throughout cells, and is a regulator of many bodily functions such as hunger, emotions, and reproduction. There is a need to identify patients who have a hormone imbalance or irregular fluctuation in hormone levels, some of which may be related to chronic conditions. Furthermore, there is a need to provide continuous monitoring of hormones in conjunction with metabolic function. Such needs represent paradigms in care where multiple decisions are guided by biology.

Current methods for measuring and monitoring hormone levels require sample collection followed by mass spectroscopy analysis. However, these methods are not practical for portable or point-of-need applications. Additionally, there are no continuous measurement options available. Quantitative levels of hormones are measured by expensive and time consuming analytical techniques such as gas or liquid chromatography-mass spectrometry (GCMS or LCMS). Such techniques are neither easily accessible or adaptable to point of care (POC) detection.

Accordingly, there is a need for a point-of-care biosensor device for specifically detecting the levels of hormones in fluid samples, which enables real-time and continuous detection, and can be easily and inexpensively manufactured.

SUMMARY

The technology described herein relates to an amperometric biosensor, e.g., a chronoamperometric biosensor for the measurement of hormone. In order to design a chronoamperometric sensor for hormones, a hormone sensing element, also referred to herein as a hormone biorecognition element, was identified from a bacterial source. In some embodiments, the disclosed hormone biosensor is a single use biosensor. In some embodiments, the disclosed biosensor is a wearable hormone biosensor. Hormones are human chemicals messengers that control bodily functions from hunger and emotion to reproduction. Cellular hormone-sensitive enzymes are a source of sensing element for detection and quantification of hormones. In the presence of the substrate, oxidase hormone enzymes produce hydrogen peroxide which may be used for amperometric measurement, e.g. chronoamperometric measurement. In the case of dehydrogenase hormone enzymes and in the presence of substrate, direct electron transfer is used to quantify hormone concentration from samples chronoamperometrically. Disclosed is a point-of-care (POC) hormone detection device with sensitivity and specificity for clinical use as well as quantification of hormones from samples.

One aspect of the disclosed technology is a hormone biosensor comprising an electrode comprising a surface, and on its surface, a hormone-catalyzing enzyme that can catalyze a hormone to produce an electrochemical signal. For example, a hormone-catalyzing enzyme that can catalyze a hormone analyte to release electrons that can be detected by a suitable electron detection method. In another aspect, the hormone-catalyzing enzyme is electronically coupled to a redox mediator (referred to herein as a "Med" or an "electronically active mediator"), so that when the hormone-catalyzing enzyme catalyzes a hormone analyte, it transfers electrons (i.e., causes a redox reaction) to a redox mediator (electronically active mediator), were the redox mediator (electronically active mediator) then transfers electrons, either directly (or indirectly, as discussed herein with the use of Intermediate Redox Enzymes) to a suitable electron detection method, for example, to an electrode to produce a current, or to an electronically excitable product which can be detected by fluorescence or colorimetric methods.

Accordingly, in one aspect, disclosed is a biosensor for measuring a concentration of a hormone. In embodiments, the biosensor comprises an electrode comprising a surface and a hormone-degrading enzyme deposited on the surface of the electrode. In embodiments, the enzyme is a recombinant 3-ketosteroid-Δ1-dehydrogenase enzyme. In embodiments, the recombinant 3-ketosteroid-Δ1-dehydrogenase enzyme is 3-ketosteroid-Δ1-dehydrogenase enzyme 1 (KSDH1) or 3-ketosteroid-Δ1-dehydrogenase enzyme 2 (KSDH2).

One embodiment is a hormone electrochemical biosensor for measuring a concentration of a hormone, comprising an electrode comprising a surface, and a recombinant 3-ketosteroid dehydrogenase enzyme 1 (KSDH1) deposited on the surface of the electrode. In embodiments, the KSDH1 enzyme catalyzes a hormone to produce an electrochemical signal. In embodiments, the catalyzed hormone analyte releases electrons that can be detected by an electron detection method. In the embodiments, the KSDH1 enzyme reduces an internal enzyme cofactor, e.g., flavin adenine dinucleotide (FAD) that releases electrons to produce an electrochemical signal in the presence of an appropriate electrical potential, wherein the electrochemical signal is detected by current passed to the electrode.

Another embodiment is a hormone biosensor that comprises: (a) an electrode comprising a surface; (b) an electronically active mediator deposited on the surface of the electrode; and (c) a hormone-catalyzing enzyme, e.g., a KSDH1 dehydrogenase enzyme deposited on the surface of the electrode, wherein the hormone-catalyzing enzyme catalyzes a hormone to produce electrons that can be detected by a detection method.

In the embodiments, the hormone is progesterone or hydrocortisone.

In the embodiments, the biosensor is an amperometric biosensor. In some embodiments, the amperometric biosensor is a chronoamperometric biosensor.

In the embodiments, the disclosed hormone biosensor produces a signal or response that is: (1) specific to a hormone, (2) occurs in real-time, and (3) is continuous. Moreover, the described hormone biosensor can also be easily and inexpensively manufactured, and manufactured at scale using well established methods. In some embodiments, the readout of the described biosensor requires simple, inexpensive, and miniaturizable electronics.

Another aspect of the disclosure is a method of using a biosensor to measure a concentration of a hormone comprising: a obtaining a hormone biosensor described herein that comprises an electrode comprising a surface and a KSDH1 dehydrogenase enzyme deposited on the surface of the electrode; providing a sample; and measuring a current produced by the oxidation of a hormone in the sample.

Disclosed is an enzyme-based electrochemical hormone biosensor that can specifically and continuously detect a hormone in real-time and at concentrations appropriate for a range of commercial and health applications. The underlying sensing part is a hormone degrading enzyme, for example, KSDH1 enzyme, which function similar to glucose dehydrogenase found in commercially available continuously monitoring glucose biosensors. Thus, the KSDH1 enzyme can be used as a biorecognition element and combined with known biosensor components for the generation of a small scale, portable biosensor, that can be a point-of-care (POC) monitor that can measure hormone levels in fluids, e.g., bodily fluids. Accordingly, the disclosed hormone biosensor can be used to test hormone levels from fluids, e.g., bodily fluids, such as human bodily fluids.

Accordingly, another aspect of the disclosed technology is a wearable hormone biosensor device. In some embodiments, a wearable KSDH1 device comprises two parts, an electroconductive part comprising a housing with a removable lid, and within the housing an electric control circuit to control the screen printed electrode (SPE), a battery, and PDMS layer housing a paper channel to wick sweat or interstitial fluid from the skin of a subject into the SPE. Magnets or other means can be used to attach the removable lid to the housing. The housing is positioned above or adjacent to a two electrode-screen printed electrode (SPE), where at least one electrode has a KSDH1 enzyme deposited on, where the KSDH1 serves as the hormone biorecognition element, and where the SPE is in fluid communication via the paper channel to a wicking apparatus, where the wicking apparatus contacts the skin of the wearer (i.e., the subject) and wicks sweat or interstitial fluid from the surface of skin of a subject. In particular, the SPE is in fluid communication via a paper channel with a wicking paper, where the wicking paper wicks sweat or interstitial fluid from the skin surface of a subject, and 1) the sweat or interstitial fluid is wicked onto the SPE by the paper channel, and then, 2) sweat or interstitial fluid is drawn towards the sink by capillary action and passed onto of the 2-electrode sensor comprising the KSDH1 biorecognition element, and 3) sweat or interstitial fluid is collected at the sink after measurement. The wearable hormone biosensor has high sensitivity and can repeatedly measure hormones in numerous samples, and has a sensitivity to be able to detect hormone.

Another embodiment is a wearable electrochemical hormone biosensor device comprising: an electroconductive part comprising a housing containing an electric control circuit; a working electrode comprising a surface; and a recombinant KSDH1 enzyme deposited on the surface of the working electrode. In embodiments, the biosensor is electrically connected to a potentiostat. In some embodiments, the potentiostat is linked to at least the working electrode of the biosensor, and the working electrode is in fluid communication with a wicking paper that wicks sweat or interstitial fluid from the surface of the skin of a subject.

In some embodiments, when attached to the skin of a subject, the wearable hormone biosensor is operable to detect the amount of hormone in the sweat or interstitial fluid of the subject, in a real time, quantitative and chronoamperometric manner.

A further embodiment is a method of using a biosensor to measure a concentration of a hormone, comprising providing the hormone biosensor described in the embodiments, providing a sample; and measuring a current produced by reduction of a hormone in the sample. In some embodiments, the KSDH1 dehydrogenase enzyme reduces an internal enzyme cofactor that releases electrons to produce an electrochemical signal. In some embodiments, the electrochemical signal is detected by current passed to the electrode. In some embodiments, the hormone is hydrocortisone or progesterone. In the embodiments, the internal enzyme cofactor is FAD.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The teachings in the present disclosure will be more fully understood from the following description of various illustrative embodiments, when read together with the accompanying drawings. It should be understood that the drawings described below are for illustration purposes only and are not intended to limit the scope of the present teachings in any way.

(FIG. 5B). New protein purification protocol provides higher purity. (FIG. 5C). KSDH1 pI=4.85, at pH 7 net charge=−28.92.

FIG. 6A is a schematic showing the Amplex® UltraRed mechanism for oxidase enzymes. Hormone is oxidized into product and $H_2O_2$ with presence of analyte and $O_2$. Horseradish peroxidase (HRP) then oxidizes Amplex® UltraRed in the presence of $H_2O_2$ into resorufin, which is fluorescent. FIG. 6B shows that the signal is analyte dependent and KSDH1 is responsive to progesterone and hydrocortisone, although the signal is weak; tested 500 µM final PRG, CRT, ESD, and ESN, 25 µM final ALD, 4.56 µM KSDH1; normalized (analytes without enzyme subtracted).

FIG. 8A is a schematic of an electron flow mechanism for the hormone biosensor that can be comprised composed of a carbon three-electrode screen printed electrode (SPE) with a Ag/AgCl reference electrode. The SPE is constructed by depositing a carbon and Prussian Blue mediator ink as the electrodes. Enzyme is then deposited onto the SPE working electrode (WE) with chitosan, a natural polymer. When analyte is added onto the three electrodes of the SPE the circuit is completed between them, and a current response can be measured when a constant potential is applied by a potentiostat. The presence of the analyte in the solution causes the creation of a diffusion layer and a gradient between regions of high and low analyte concentrations. This gradient creates flux governed by Fick's Law and drives the movement of analyte to the working electrode. FIG. 8B shows KSDH1 is slow for an oxidase based electrochemical biosensor, as compared to NicA2, an already slow oxidase.

(FIG. 11B). KSDH1 is closest to FAD glucose dehydrogenase (FADGDH) (FIG. 11C). Table from Ferri et al.

FIGS. 14A-B. Illustrates various screen printed electrodes (SPEs), DSF10: Carbon+Potassium ferricyanide (PF); DS110: Carbon; and DS710: Carbon+Prussian Blue (PB) (FIG. 14A), and soluble mediators with their corresponding redox potential and charge: mPMS −0.14 V, +/0; RU −0.11V, +3/+2; and PF +0.23 V, −3/−4 (FIG. 14B). Data from Loew et al.

FIG. 15 is a schematic of a second-generation electron flow mechanism for a hormone dehydrogenase electrochemical biosensor using an enzyme with an internal FAD cofactor (i.e. KSDH1) using soluble mediators or SPEs outlined in FIGS. 14A-B.

DETAILED DESCRIPTION

Figure 1A:
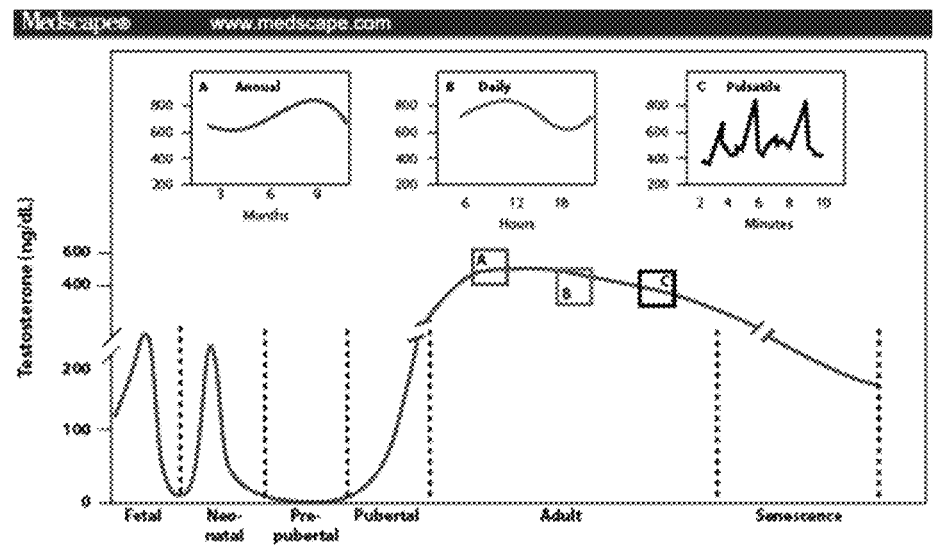
FIGS. 1A-B illustrate human chemical messengers that control bodily functions such as hunger, emotion, and reproduction.
Figure 1B:
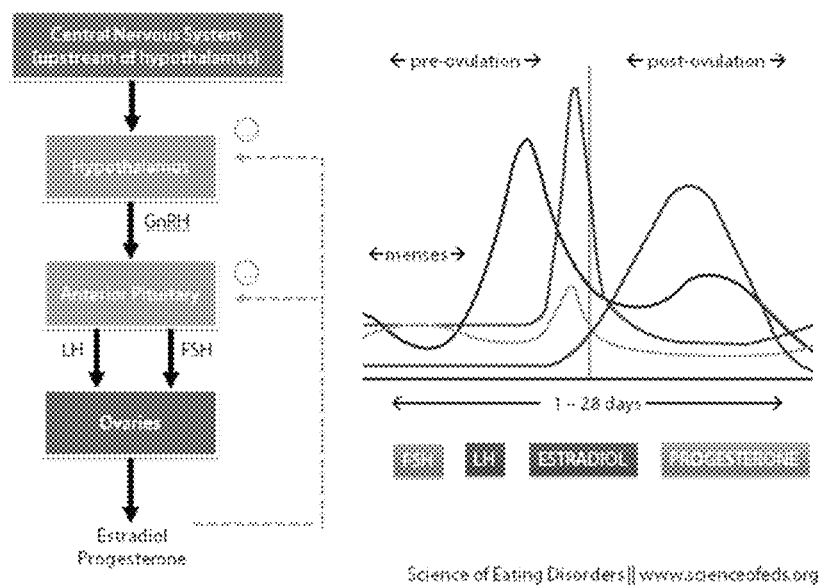
Figure 2A:
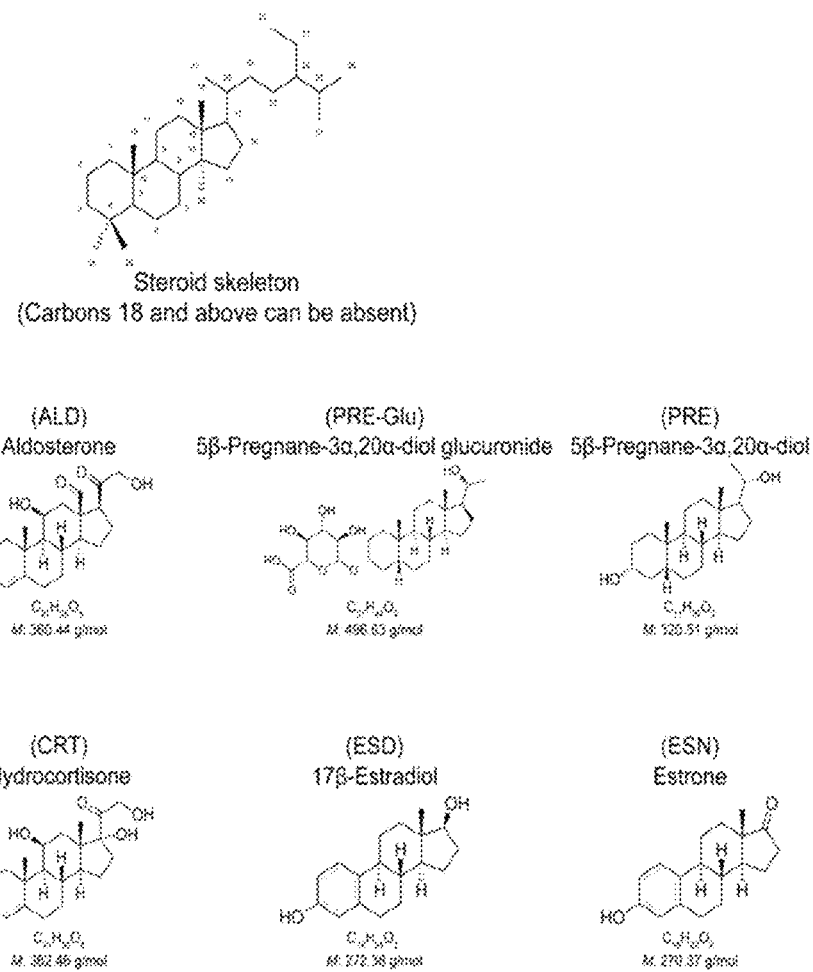
FIGS. 2A-2B illustrate common steroid structures (FIG. 2A), and cellular location and mechanism of hormone-responsive enzymes involved in human steroidogenesis (FIG. 2B). Häggström et al.
Figure 2B:
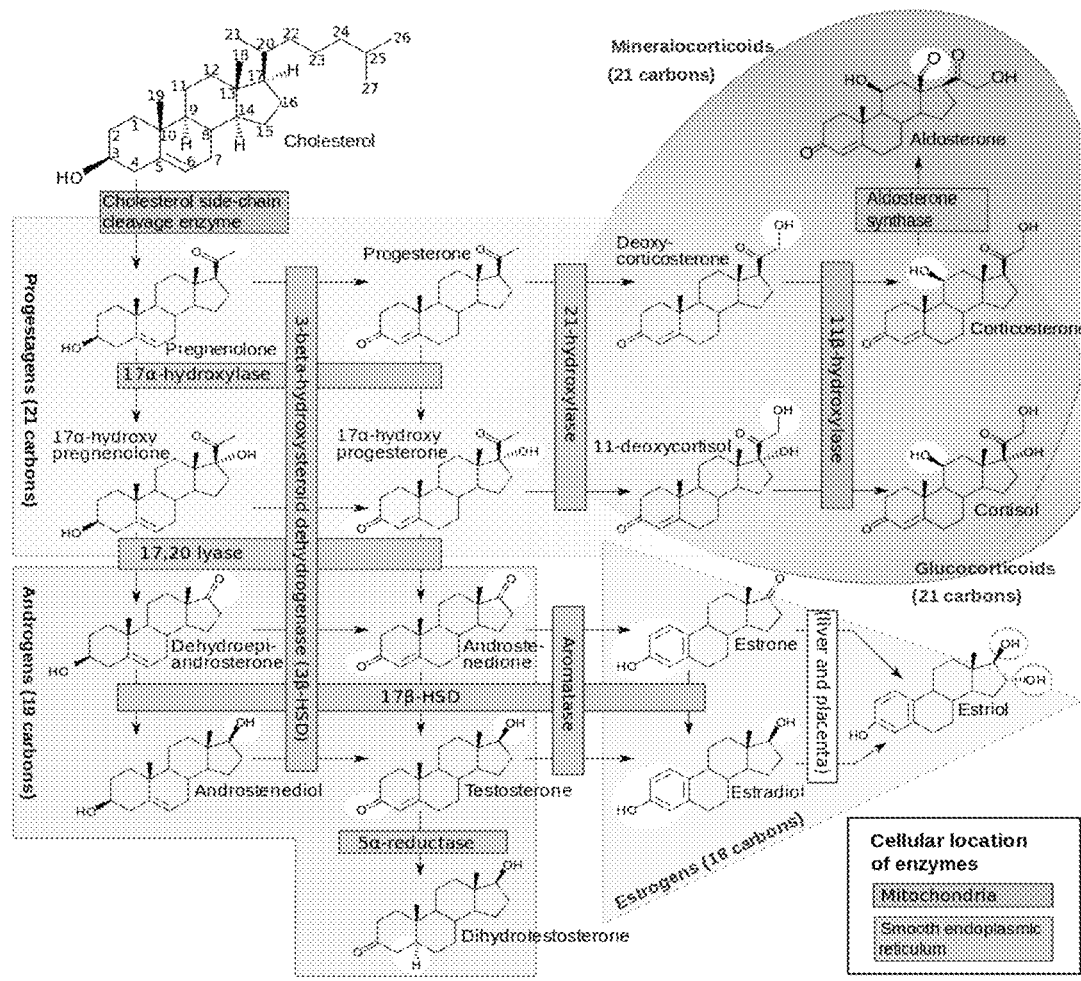

The technology described herein relates to an amperometric biosensor, e.g., chronoamperometric biosensor for the measurement of hormones. In order to design a chronoamperometric sensor for hormones, a hormone sensing element was identified from a bacterial source. Bacteria have evolved over 3 billion years to detect and respond to virtually all classes of stimuli or chemicals relevant to their surroundings. For example, *Pimelobacter simplex* is a source of 3-ketosteroid-Δ1-dehydrogenase (KSDH) that degrades hormones. Since *P. simplex* metabolizes hormones, identification and utilization of a ketosteroid enzyme can provide such a sensing element in a biosensor. In the presence of the substrate, KSDH produces degrades hormones and reduces its internal cofactor allowing for chronoamperometric measurement. Described herein is a recombinant KSDH1 enzyme for degrading hormone analyte and allowing detection and quantification of hormones. Also described is a prototype point-of-care (POC) detection device based on a recombinant KSDH1 enzyme with sensitivity and specificity for clinical use as well as quantification of hormone from samples. Accordingly, in one aspect, described herein is an amperometric biosensor, e.g., chronoamperometric biosensor comprising: (a) an electrode comprising a surface; and (b) a hormone-catalyzing enzyme deposited on the surface of the electrode, wherein the hormone-catalyzing enzyme is a dehydrogenase that catalyzes a hormone, such as progesterone or cortisol, reducing its internal cofactor (FAD) in the process.

I. Elements of a Hormone Biosensor Device

Label-free sensing of analytes such as hormones is of critical importance to biomedical research, point of care diagnostics, and environmental sensing, among other applications. Connected devices that monitor human biology or the environment in real-time represent the next frontier in biosensors. Monitoring hormones is of significant interest to subjects with hormone imbalance. However, the real-time monitoring of analytes such as a hormone is challenging from a biology, chemistry, and engineering perspective, with glucose detection being the one notable success. Using natural sensing elements from microbial species, e.g. native biomolecules that have evolved sensor and modulator capabilities, provides the opportunity to utilize a detection platform that is distinct from the typical antibody- or aptamer-based strategies for hormone detection. Described herein is an amperometric, e.g., a chronoamperometric biosensor for the measurement of hormones in a sample.

A biosensor is a device comprising a biological sensor element (also referred to as a biorecognition element or biological component) that typically produces electronic signals that are proportional to the concentration of a particular substance to be determined. As used herein the term "amperometric" refers to the measurement of current between electrodes, and "chronoamperometric" refers to the measurement of current between electrodes as a function of time.

Biosensors, e.g., nanobiosensors are a type of analytical device that use biological molecules to monitor biorecognition events and interactions. Generally, a biosensor comprises a biological component, a redox-mediator alongside nanoelectrodes; the various components can be equated with the electronic elements of a sensor because the components transduce the signal generated at the source (bioelement) to the detector (electrode). In general, a biological component of a biosensor can be a protein (e.g., enzyme or antibody), nucleic acid (DNA or RNA) or even entire cells.

The use of enzymes as bioactive interfaces is well known in the art, and such interfaces are used in analytical methods of detecting electronic transduction of enzyme-substrate reactions. Direct electrical activation of enzymes such as redox enzymes permits stimulation of bioelectrocatalyzed oxidation or reduction of enzyme substrates. Rapid transfer of electrons between an electrode and a given redox enzyme results in current generation corresponding to the rate of turnover of the electron exchange between the substrate and biocatalyst. In other words, the transduced current of the system correlates with enzyme substrate concentration. Electrical contacting of redox proteins in a biosensor and the electrode support contained therein may be mediated by direct electron transfer with electrode surfaces. Redox enzymes lacking direct electrical communication with electrodes may achieve electrical contact by mediated electron transfer via redox mediators that serve as active charge carriers.

For non-limiting examples of biosensors, see e.g., U.S. Pat. Nos. 6,241,863, 6,736,777, 7,794,994; US patent publications US 2003/0027239, US 2009/0099434, US 2009/0061451, US 2012/0181189, US 2019/0004005; PCT publications WO 2013/059534, WO 2005/048834; European patent 1194585; Vigneshvar et al. Front Bioeng Biotechnol. 2016, 4:11; Turner, Chem Soc Rev. 2013 Apr. 21, 42(8): 3184-96; Hosu et al., Talanta Volume 204, 1 Nov. 2019, Pages 525-532; the contents of each of which, including but not limited to biosensors and methods and systems comprising them, are incorporated herein by reference in their entireties.

One aspect of the disclosed technology is a hormone biosensor comprising an electrode, comprising on its surface a hormone-catalyzing enzyme, where the hormone-catalyzing enzyme binds to, and catalyzes the analyte hormone, and transfers electrons (i.e., causes a redox reaction) directly to an electrode, without a mediator.

Another aspect of the disclosed technology is a hormone biosensor, comprising an electrode comprising on its surface, a hormone-catalyzing enzyme, where the hormone-catalyzing enzyme is electronically coupled to a redox mediator (referred to herein as a "Med" or an "electronically active mediator"), so that when the hormone-catalyzing enzyme binds to, and catalyzes the analyte hormone, it transfers electrons (i.e., causes a redox reaction) to a redox mediator/electronically active mediator, were redox mediator/electronically active mediator then transfers electrons, either directly (or indirectly, as discussed herein with the use of Readout enzyme) to a suitable electron detection method, for example, to an electrode thereby producing a current, or to an electronically excitable product.

Without limitation to one aspect, in catalyzing hormone to a product, the hormone-catalyzing enzyme causes a redox event that is coupled to a redox mediator, which acts as a conductor of electrons to the detector, typically an electrode, thereby relaying the detection of the hormone analyte. In some embodiments, the amount of electrons produced, and detected by the electron detector is corresponds to the amount of the analyte, in this instance, the amount of hormone. In some embodiments, the biosensor is set up to allow multiple redox events, e.g., 2, or 3 redox events. In some embodiments, a redox event occurs between the transfer of electrons from the hormone to the redox mediator/electronically active mediator when the hormone is catalyzed to a product (step 1), and a second redox event occurs the when the reduced redox mediator returns to the oxidized form, thereby transferring electrons to the electron detector, typically an electrode (step 2). In another embodiment, a redox event occurs between the transfer of electrons from the hormone to a redox mediator/electronically active mediator when hormone is catalyzed to product (step 1), where the redox mediator/electronically active mediator can only accept the electrons in the presence of an intermediate redox enzyme (IRE), and a second redox event occurs when the reduced redox mediator produces a signal (step 2).

The disclosed technology relates to a hormone biosensor device comprising a hormone detecting or hormone catalyzing redox-enzyme. Redox-enzymes in general are responsible for the binding and recognition of the special target analyte, whether a small molecule or a large protein partner. The binding of the redox-enzyme to the target analyte is the basis for signal generation and a physical element, such a detectable signal is generated, and can an electrode, captures the signal as the output. Thus, coupling the redox-enzyme with a mediator or directly to the electrodes, translates information from the binding of the target analyte and redox-enzyme into a chemical or physical output with a defined sensitivity. The information that is detected can be chemical, energetic, such as detection of light, and/or signal detection and transduction.

A "redox enzyme" or "oxidoreductase" or "dehydrogenase" are used interchangeably herein and refer to an enzyme that catalyzes a reaction with one or more enzyme substrate(s), resulting in generation or utilization of electrons. Redox enzymes are proteins that catalyze electron transfer by reduction or oxidation of substrates within the redox network. The oxidoreductase or dehydrogenase (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection of reduced coenzyme nicotinamide adenine dinucleotide (NADH) or hydrogen peroxide has been used in galvanometer biosensors.

A redox reaction is a chemical reaction in which the oxidation states of atoms are changed. Any such reaction involves both a reduction process and a complementary oxidation process, two key concepts involved with electron transfer processes. Redox reactions include all chemical reactions in which atoms have their oxidation state changed; in general, redox reactions involve the transfer of electrons between chemical species.

Aspects of the biosensor described herein rely on catalyzing an electrochemical reaction (redox) of the redox-enzyme biosensor in the presence of a target analyte (i.e., substrate; e.g., a hormone). In use, an analyte specific to the redox-enzyme biosensor is catalyzed, changing electron flow through the biosensor. In one non-limiting embodiment, the redox-enzyme biosensor (or a functional portion thereof) catalyzes a redox event in the presence of a target analyte (i.e., where the analyte is a substrate of the redox enzyme). The redox event can be coupled to a redox-mediator (referred to herein as a "Med") which acts as a conductor of electrons to permit detection of the redox event between the target analyte (e.g., hormone) and the redox-enzyme (e.g., hormone-catalyzing or -detecting redox enzyme). In some embodiments, the redox event between the target analyte (e.g., hormone) and the redox-enzyme (e.g., hormone-catalyzing or -detecting redox enzyme), e.g. KSDH1, can be coupled to an intermediate redox enzyme (IRE), that acts as a conductor of electrons between the first redox event (between and the redox-enzyme (e.g., hormone-catalyzing or -detecting redox enzyme) and the redox-mediator (Med). In some embodiments, the redox-mediator can be linked to an electrode, nano-electrode or nanobioneedle, which all act as conductors of electrons to permit detection of any signal changes in the redox-enzyme biosensor.

In some embodiments, the redox-mediator generates a signal detectable by optical methods, such as, without limitation, fluorescence, surface plasmon resonance, or piezoelectric methods.

In some embodiments of the disclosed technology, the described hormone biosensor comprises a hormone-catalyzing enzyme (KSDH1) encoded by SEQ ID NO: 1 or a nucleic acid sequence that is at least 70%, at least 80%, at least 90%, at least 91%, at least 92%, at least 93%, at least 94%, at least 95%, at least 96%, at least 97%, at least 98%, at least 99%, or at least 99.5% identical to the sequence of SEQ ID NO: 1 that maintains the same function (e.g., hormone degradation).

SEQ ID NO: 1 (nucleic acid of KSDH1):

(SEQ ID NO: 1)
ATGGACTGGGCAGAAGAGTATGATGTGTTGGTAGCTGGATCCGGTGCTGG

CGGTATGGCTGGGACCTATACGGCAGCGCGTGAGGGTCTGTCCGTATGTC

TGGTAGAGGCTGGGGACAAATTTGGAGGCACTACTGCATACTCAGGCGGA

GGGGGAGCGTGGTTTCCTGCAAATCCGGTACTGTTGCGTGCGGGAACCGA

TGACACCATCGAGGATGCCCTGGAGTATTATCGTGCTGTAGTTGGTGACC

GTACCCCGGCTGACTTGCAAGAAACCTACGTACGCGGGGAGCTGGGTTG

GTCGCCTATTTGGAGGAGGATGACCATTTTTCGTTTGAATCGTACCCATG

GCCTGATTATTTTGGCGACGCCCCTAAGGCCCGTCGTGACGGTCAGCGTC

-continued
ATATTATTCCCACACCCCTGCCGGTACCCTCAGCCCCGGAGTTGCGCGAA

GTAGTTCGTGGTCCTTTGGATAATGATCGTTTGGGAACCCCTCAACCCGA

TGACCTGTTCATCGGCGGACGTGCCTTAGTTGCCCGTTTTCTTACTGCCT

TAGCTACCTACCCGCACGCAACTCTGGTCCGTGAGACTGCTTTAGCAGAG

CTTGTGGTTGAGGACGGGGTAGTAGTGGGGGCCATTGTAGAAACCGACGG

CGTCCGCCGTGCCATTCGCGCACGCCGTGGTGTACTGCTTGCAGCTGGGG

GTTTTGAGGCCAATGACGAATTACGTCAGAAGTATGGAGTGCCAGGAGTA

GCCCGCGACACAATGGGACCCCCCACGAACGTTGGCGCAGCGCATCAGGC

GGCCATCGCCGTTGGCGCTGATACCGACCTTATGGGTGAGGCCTGGTGGT

CGCCTGGACTGACACATCCTGACGGACGTTCTGCATTTGCGCTGTGGTTC

ACGGGAGGAATTTTTGTTGATGGAGCAGGTCGTCGTTTTGTAAATGAGTC

CGCCCCATACGATCGCCTGGGTCGTGCTGTTATTGACCACTTAACAGAGG

GAGGCGTAACCCCCCGTTATTGGATGGTTTACGACCATAAAGAGGGCTCC

ATTCCCCCTGTACGTGCGACTAACGTAAGTATGGTGGACGAGGAACAATA

TGTAGCAGCTGGACTGTGGCACACGGCAGACACCCTTCCTGAGCTTGCTG

CTTTAATCGGTGTCCCCGCTGATGCTCTTGTGGCGACCGTAGCCCGTTTC

AATGAACTTGTTGCGGATGGCTACGATGCGGATTTTGGTCGCGGGGCGA

AGCGTATGATCGCTTCTTTTCTGGAGGGGAACCTCCATTAGTATCAATTG

ACGAAGGTCCCTTCCACGCGGCCGCATTTGGAATCTCTGATTTGGGTACA

AAGGGAGGCTTACGCACGGATACCTCCGCCCGCGTATTAACAGCCGATGG

GACGCCCATTGGTGGATTGTATGCGGCTGGTAACACGATGGCCGCACCGA

GTGGAACCACGTACCCAGGGGGCGGAAATCCGATCGGAACGTCGATGTTG

TTCTCCCACCTTGCAGTGCGCCACATGGGTACCGAGGACGCGCGCGGTTC

GCACCACCACCACCACCACT

In some embodiments of the disclosed technology, the amino acid sequence of the hormone-catalyzing enzyme comprises SEQ ID NO: 2 or an amino acid sequence that is at least 70%, at least 80%, at least 90%, at least 91%, at least 92%, at least 93%, at least 94%, at least 95%, at least 96%, at least 97%, at least 98%, at least 99%, or at least 99.5% identical to the sequence of SEQ ID NO: 2 that maintains the same function of SEQ ID NO: 2 (e.g., hormone degradation).

SEQ ID NO: 2 (amino acid sequence KSDH1)(which is encoded by SEQ ID NO. 1).

(SEQ ID NO: 2)
MDWAEEYDVLVAGSGAGGMAGTYTAAREGLSVCLVEAGDKFGGTTAYSGG

GGAWFPANPVLLRAGTDDTIEDALEYYRAVVGDRTPADLQETYVRGGAGL

VAYLEEDDHFSFESYPWPDYFGDAPKARRDGQRHIIPTPLPVPSAPELRE

VVRGPLDNDRLGTPQPDDLFIGGRALVARFLTALATYPHATLVRETALAE

LVVEDGVVVGAIVETDGVRRAIRARRGVLLAAGGFEANDELRQKYGVPGV

ARDTMGPPTNVGAAHQAAIAVGADTDLMGEAWWSPGLTHPDGRSAFALWF

TGGIFVDGAGRRFVNESAPYDRLGRAVIDHLTEGGVTPRYWMVYDHKEGS

IPPVRATNVSMVDEEQYVAAGLWHTADTLPELAALIGVPADALVATVARF

```
-continued
NELVADGYDADFGRGGEAYDRFFSGGEPPLVSIDEGPFHAAAFGISDLGT

KGGLRTDTSARVLTADGTPIGGLYAAGNTMAAPSGTTYPGGGNPIGTSML

FSHLAVRHMGTEDARGSHHHHHH*
```

In some embodiments, directed evolution of the KSDH1 enzyme can be done to improve selectivity, catalytic efficiency ($k_{cat}/K_M$), and substrate affinity ($K_M$). In alternative embodiments, alternative hormone-catalyzing enzymes can be used, or hormone-catalyzing redox enzymes from other that have similar or enzymatic properties to KSDH1.

In some embodiments, the hormone-catalyzing enzyme is immobilized on an electrode of the biosensor. In some embodiments of any of the aspects, the hormone-catalyzing enzyme is deposited on electrodes without an immobilizing agent.

In an embodiment, the hormone-catalyzing enzyme is immobilized on the electrode with chitosan. Chitosan was selected as a matrix for immobilization of the enzyme because of its biocompatibility, non-toxicity, high mechanical strength and excellent membrane forming ability. Chitosan can be divided into three categories, namely low molecular weight (e.g., 50 kDa-190 kDa), medium molecular weight (e.g., 190 kDa-310 kDa), and high molecular weight (e.g., 310 kDa-375 kDa). Chitosan of higher molecular weight possesses longer molecular chains with the availability of more hydroxyl groups. There is also a higher possibility that there are more amino groups, although the number of amino groups is determined by the degree of deacetylation. These amino groups are responsible for crosslinking. In some embodiments of any of the aspects, higher molecular weight chitosan (e.g., medium molecular weight compared to low molecular weight chitosan) can improve enzyme retention activity and loading, and thus function as a suitable matrix for enzyme immobilization. Using this chitosan membrane as a biosensor can provide a better performance in terms of sensitivity and stability. In some embodiments of any of the aspects, an amperometric biosensor, e.g., chronoamperometric biosensor can comprise chitosan of different molecular weights as a matrix for enzyme immobilization using a variety of adsorption and crosslinking techniques. See e.g., Ang et al., Study on Different Molecular Weights of Chitosan as an Immobilization Matrix for a Glucose Biosensor, PLoS One. 2013 Aug. 5,8(8):e70597; Teepoo et al., Electrospun Chitosan-Gelatin Biopolymer Composite Nanofibers for Horseradish Peroxidase Immobilization in a Hydrogen Peroxide Biosensor, Biosensors (Basel). 2017 Oct. 15; 7(4). pii: E47. In some embodiments of any of the aspects, the hormone-catalyzing enzyme is immobilized on the working electrode of the biosensor as described further herein.

In some embodiments of any of the aspects, the hormone-catalyzing enzyme is immobilized on the electrode surface using crosslinking of a redox polymer. Generally, an aqueous mixture containing the enzymes, the redox polymer, and crosslinking agent in an aqueous solution are applied on an electrode and dried or allowed to dry to form a sensing film or coating on the electrode surface. See e.g., US patent publication US 2012/0181189.

In some embodiments of any of the aspects, the hormone-catalyzing enzyme is immobilized on the electrode surface on a self-assembled monolayer (SAM) comprising chemisorbed alkanethiols. In this embodiment, a gold electrode is preferred as the transducer in the sensor system since thiols chemisorb to gold to give a strong, stably bound layer. Other chemical groups suitable for adsorption to a metal surface include sulfates, sulfonates, phosphates, and selenides. In some embodiments, thiol chemisorption on gold yielding thiolate is preferred, due to the relative stability of the metal-sulfur bond. See e.g., U.S. Pat. No. 6,241,863, the content of which is incorporated by reference herein it its entirety.

In some embodiments of any of the aspects, the hormone-catalyzing enzyme is immobilized on the electrode surface using glutaraldehyde.

In some embodiments of any of the aspects, the hormone-catalyzing enzyme is deposited on the electrode surface and left to dry without an immobilizing agent.

A. Detection of a Signal from KSDH1 Catalysis of a Hormone.

In some embodiments, an exemplary hormone biosensor disclosed herein comprises KSDH1 dehydrogenase alone or with another hormone biosensing redox enzyme. In one embodiment, the hormone biosensor can operate with the following reaction steps shown in the reaction scheme 1 below:

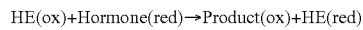

HE(ox)+Hormone(red)→Product(ox)+HE(red)

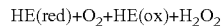

HE(red)+O$_2$+HE(ox)+H$_2$O$_2$

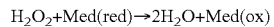

H$_2$O$_2$+Med(red)→2H$_2$O+Med(ox)

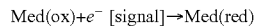

Med(ox)+$e^-$ [signal]→Med(red)

In another embodiment, the hormone biosensor can operate with the following reaction steps shown in the reaction scheme 2 below:

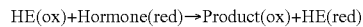

HE(ox)+Hormone(red)→Product(ox)+HE(red)

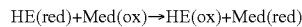

HE(red)+Med(ox)→HE(ox)+Med(red)

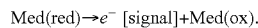

Med(red)→$e^-$ [signal]+Med(ox).

In another embodiment, the hormone biosensor can operate with the following reaction steps shown in the reaction scheme 1 below reaction scheme 3 below:

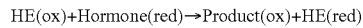

HE(ox)+Hormone(red)→Product(ox)+HE(red)

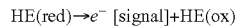

HE(red)→$e^-$ [signal]+HE(ox)

In the above reaction schemes 1, 2, and 3, HE(ox) is an oxidized form of the hormone enzyme (HE), e.g., KSDH1 dehydrogenase, HE(red) is a reduced form of the hormone enzyme (HE), e.g., KSDH1 dehydrogenase, Med(ox) is an oxidized from of the redox mediator, and Med(red) is a reduced form of the redox mediator.

In step 1, the hormone enzyme (HE), e.g., KSDH1 dehydrogenase oxidizes hormone to produce a product and the HE itself is reduced (specifically, its internal cofactor). In step 2, the reduced form of the hormone enzyme (HE), e.g., KSDH1 dehydrogenase reacts with oxygen in order to produce hydrogen peroxide. In step 3, hydrogen peroxide is oxidized into water while the oxidized form of the redox mediator Med(ox) is reduced to Med(red). In step 4, in the presence of an electric potential, the Med(red) is oxidized to regenerate Med(ox) and a measurable detectable signal is produced in the form of electrons. In some embodiments, the electrons are a detectable signal which can be measured as a current (amperometrically).

In some embodiments, a hormone can be identified through electrochemical methods ($2^{nd}$ generation) using a hormone NAD(P)-dependent dehydrogenase enzyme as shown in reaction scheme 1 as follows:

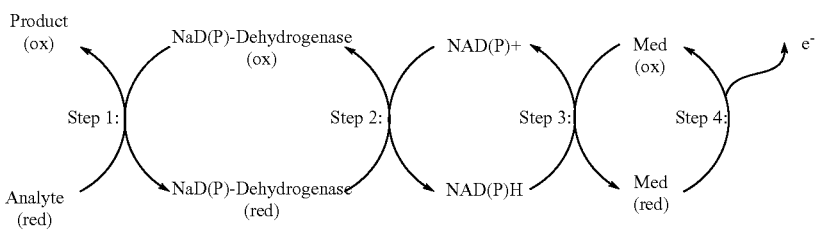

In some embodiments, a hormone can be identified through electrochemical methods (2$^{nd}$ generation) using a hormone FAD-dependent dehydrogenase enzyme, e.g. KSDH1.

In some embodiments, hormone can be identified through electrochemical methods (3$^{rd}$ generation) using the hormone NAD(P)-dependent dehydrogenase enzyme as shown in reaction scheme 2 as follows:

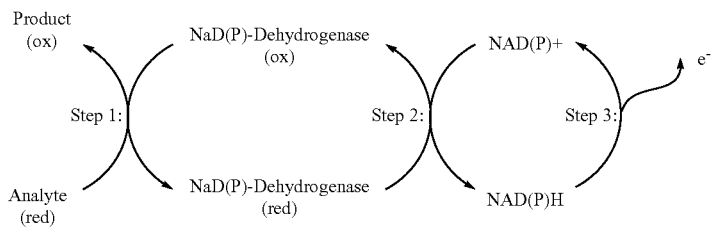

In the embodiments, a hormone can be identified through electrochemical methods (2$^{nd}$ generation) using a hormone FAD-dependent dehydrogenase enzyme, e.g. KSDH1.

In some embodiments, a hormone can be identified through electrochemical methods (2$^{nd}$ generation) using the hormone NAD(P)-independent dehydrogenase enzyme as shown in reaction scheme 3 as follows:

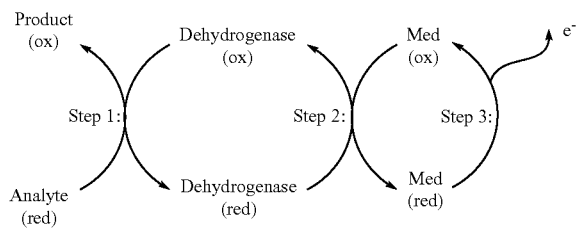

In the embodiments, a hormone can be identified through electrochemical methods (2$^{nd}$ generation) using a hormone FAD-dependent dehydrogenase enzyme, e.g. KSDH1.

In some embodiments, hormone can be identified through electrochemical methods (3 d generation) using the hormone NAD(P)-independent dehydrogenase enzyme as shown in reaction scheme 4 as follows:

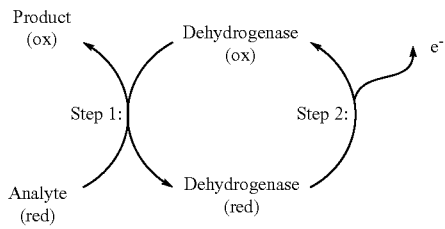

In the embodiments, a hormone can be identified through electrochemical methods (2$^{nd}$ generation) using a hormone FAD-dependent dehydrogenase enzyme, e.g. KSDH1.

In some embodiments, the hormone-catalyzing enzyme is not capable of transferring electrons to a redox mediator/ electrically active mediator directly. That is, a detectable signal is not produced when the hormone-catalyzing enzyme interacts with hormone. Accordingly, in some embodiments, hormone is detected by a hormone-catalyzing enzyme that is capable of interacting directly with hormone, but cannot exchange electrons with a redox mediator. Such an embodiment is useful where some redox-enzymes cannot exchange electrons directly with an electrode because their redox active sites are buried deep within the enzyme protein structure. Therefore, in order to transfer electrons between the redox active site of the enzyme and produce a detectable signal, a redox mediator (Med) also known as an "electron transfer agent" or an "electronically active mediator" is used. In some embodiments, the analyte-specific enzyme is cross-linked to the electron transfer agent. In some embodiments of any of the aspects, the amperometric biosensor, e.g., chronoamperometric biosensor described herein comprises an electronically active mediator deposited on the surface of the electrode.

In some embodiments, redox mediators are electroreducible and electrooxidizable ions or molecules having redox potentials (voltages) that are a few hundred millivolts above or below the redox potential (voltage) of the standard calomel electrode. In some embodiments, the redox mediators are not more reducing than about −150 mV and not more oxidizing than about +400 mV versus a standard calomel electrode. Examples of suitable redox mediators are disclosed, for example, in Mao et al. (U.S. Pat. No. 6,605,200) the entire content of which is herein incorporated by reference.

Accordingly, the biosensor disclosed herein comprises redox mediators (Med) that serve as electron carriers, or electron signal mediators. That is, they are multi-electron transfer mediators that function as electrochemically detectable signal mediators to produce a detectable signal when transfer of electrons occurs. Preferably a redox-mediator as disclosed herein is linearly or exponentially amplified by magnifying electrochemical signal output via recycling the enzyme substrates.

In some embodiments of any of the aspects, the electronically active mediator (Med) can be reduced from a reduced form (Med$_{red}$) to an oxidative form (Med$_{ox}$), wherein the Med$_{ox}$ produces a detectable signal. In some embodiments of any of the aspects, the detectable signal is produced when hormone is catalyzed by the hormone-catalyzing enzyme and transfers at least one electron from Med$_{red}$ to hydrogen peroxide (H$_2$O$_2$), resulting in its oxidation to Med$_{ox}$. In some embodiments of any of the aspects, the electronically active mediator Med$_{ox}$ is reduced by the electrode, producing a detectable signal due to the flow of electrons. In some embodiments, the redox-mediator is catalyzed to produce a detectable signal that is electrochemical or colorimetric. In some embodiments, the redox-mediator produces an optical readout comprising fluorescence, bioluminescence, or luminescence.

A redox-mediator can be any of the natural or synthetic mediators commonly used in biosensors known to date, and is preferably selected from the group consisting of cytochromes, quinones, aminophenols, electron-acceptor aromatic compounds (e.g., TTF=tetratiafulvalene and NMP=N-methylphenazine), electron-donor aromatic compounds (e.g., TCNQ=tetrakyano-p-quinodimethane), organic conductive salts (e.g., TTF.TCNQ=tetratiafulvalene-7,7,8,8-tetrakyano-p-quinodimethane and NMP.TCNQ=N-methylphenylene-7, 7,8,8-tetracyano-p-quinodimethane), organic dyes, metallocenes, organometallic complexes of osmium, ruthenium and duct, inorganic iron complexes. In some embodiments, redox mediators are ferricyanide ferrocene, 1,1-dimethyl-ferrocene, hexacyanoferrate or hexacyanoferrate, or platinum.

In some embodiments, the redox mediator is AUR as disclosed herein. Natural and artificial mediators are shown in Table 1.

TABLE 1

| Natural mediators | Artificial mediators |
|---|---|
| Cytochrome a3 | Ferricyanide (hexacyanoferrate III) |
| Cytochrome c3 | 2, 6-dichlorophenol |
| Cytochrome b | Indophenol |
| Ubiquitone | Ferrocene |
| Vitamin K2 | Phenazine |
| Rubredoxin | Methosulphate |
| Flavoproteins | Methylene blue |
| FAD-FADH$_2$ | Phtalocyannine |
| FMN-FNH$_2$ | Phenosafranine |
| NAD+-NADH | Benzyl violet |
| NADP+-NADPH | Methyl violet |
| PQQ-PQQH$_2$ | Ferredoxin |
| | Prussian Blue |
| | Nile blue |
| | Meldola's Blue |
| | NQSA |
| | Potassium hexacyanoferrate |
| | Potassium ferricyanide |
| | Potassium ferrocyanide |
| | PMS |
| | Dichlorophenolindophenol |
| | p-benzoquinone |
| | o-phenylenediamine |
| | 3,4-dihydroxybenzaldehyde |
| | Potassium hexacyanoferrate (II) |
| | Tetracyanoquinodimethane |
| | Cobalt (II) phtalocyanine |
| | Platinum |

In some embodiments, the redox-mediator is a ferricyanide compound (i.e., Prussian blue). Prussian blue is a dark blue pigment produced by oxidation of ferrous ferrocyanide salts. It has the chemical formula Fe$^{III}_4$[Fe$^{II}$(CN)$_6$]$_3$. The IUPAC name of Prussian Blue is iron(II,III) hexacyanoferrate(II,III), but it can also be referred to as Berlin blue, ferric ferrocyanide, ferric hexacyanoferrate, iron(III) ferrocyanide, iron(III) hexacyanoferrate(II), or Parisian blue. Prussian blue nanoparticles (PB NPs) exhibit an intrinsic peroxidase-like catalytic activity towards the hydrogen peroxide (H$_2$O$_2$)-mediated oxidation of classical peroxidase substrate 2,2'-azino-bis(3-ethylbenzothiazoline-6-sulfonic acid) diammonium salt to produce a colored product. See e.g., PCT publication WO 1990/012487A2, which is incorporated herein by reference in its entirety. In some embodiments, the electronically active mediator comprises a ferricyanide compound which is reducible in the presence of an electron from hydrogen peroxide (H$_2$O$_2$) to produce a ferrocyanide compound. In some embodiments, the electronically active mediator comprises iron(II,III) hexacyanoferrate(II,III) (Prussian blue).

BA. Optical or Fluorescence Detection of Hormone Using a Readout Enzyme

In some embodiments, the reaction between the hormone-catalyzing enzyme and hormone is coupled to one or more additional enzymes, herein referred to an intermediate redox enzyme (e.g., IRE) to form a multi-enzyme system for detection of the redox reaction between hormone and the hormone-catalyzing enzyme. In some embodiments of any of the aspects, the oxidase redox-enzyme of the amperometric biosensor, e.g., chronoamperometric biosensor described herein can be coupled to an intermediate redox-enzyme (IRE), for example, a peroxidase enzyme, as disclosed herein.

In some embodiments, the Med(red) can catalyze a redox reaction with a readout enzyme (ReadE) to convert a readout substrate (ReadS) into a readout product (ReadP), where the ReadP produces a detectable signal which can be measured optically, e.g., by fluorescence or other luminescence methods.

In some embodiments, a hormone biosensor described herein can also comprise an intermediate redox-enzyme. For example, the Med(ox) is reduced to Med(red) in the presence of hydrogen peroxide and a peroxidase enzyme, thereby avoiding issues of auto-oxidation of the Med(red) and increasing the accuracy of measurement of analyte concentration.

A general reaction scheme for detecting hormone using the KSDH1 biosensor comprising a readout enzyme (ReadE), such as a peroxidase can also be represented as shown in reaction scheme 8 as follows:

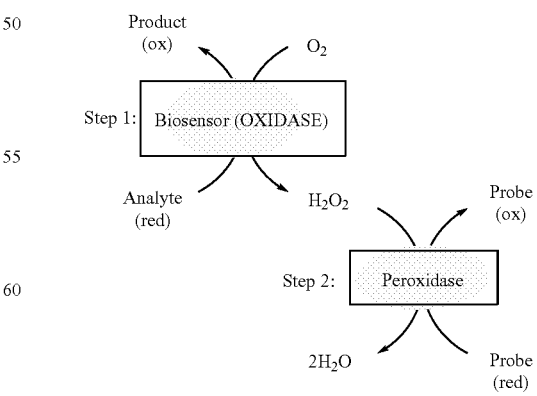

In some embodiments, the conversion of Med(red) back to Med(ox) can produce a signal which can be measured as a current or amperometrically, and the measurement can be correlated to the concentration of the analyte.

In some embodiments, the readout enzyme (ReadE) (also referred to as "intermediate redox-enzyme (TRE)") is a peroxidase enzyme, for example, but not limited to, APEX2 which, in the presence of hydrogen peroxidase, catalyzes the conversion of the readout substrate (ReadS) Amplex® UltraRed (AUR) to the readout product (ReadP) Resorufin, which produces a detectable signal. An exemplary reaction scheme for identification of an oxidase MRE using APEX2 as a peroxidase as a readout enzyme can be represented as shown in reaction scheme 5 as follows:

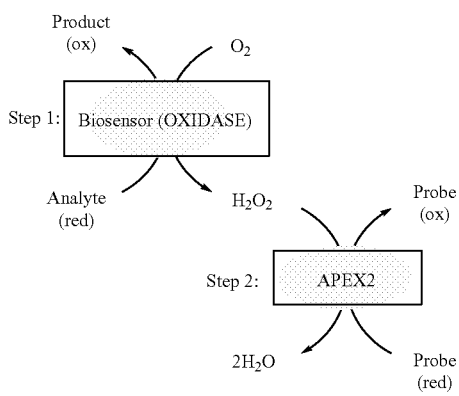

In some embodiments, a hormone can be identified through non-electrochemical methods using the NAD(P)-dependent dehydrogenase enzyme as shown in reaction scheme 6 as follows:

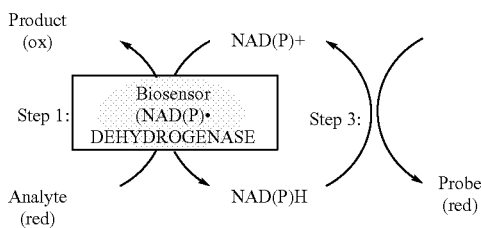

In the embodiments, a hormone can be identified through electrochemical methods ($2^{nd}$ generation) using a hormone FAD-dependent dehydrogenase enzyme, e.g. KSDH1.

In some embodiments, hormone can be identified through non-electrochemical methods using the NAD(P)-independent dehydrogenase enzyme as shown in reaction scheme 7 as follows:

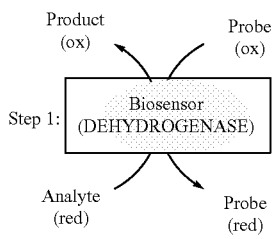

In the embodiments, a hormone can be identified through electrochemical methods ($2^{nd}$ generation) using a hormone FAD-dependent dehydrogenase enzyme, e.g. KSDH1.

In some embodiments, the intermediate redox enzyme (IRE) is a peroxidase enzyme, for example, but not limited to, APEX2, and the redox mediator (Med) is Amplex® UltraRed (AUR) that in the presence of hydrogen peroxidase and the peroxidase enzyme APEX2, is converted to Resorufin which produces a detectable signal.

In some embodiments, the technology encompasses alternative or modified Readout substrates (also referred to herein as intermediate redox enzymes (IREs)), for example, such as modifying the APEX2 enzyme to have improved enzyme kinetics or to use alternative peroxidase enzymes, or HRP derivatives. Additionally, in some embodiments, the redox-mediator, such as AUR, can be replaced with other $H_2O_2$ responsive probes known in the art, for example, but not limited to PY1, PO1, Amplex® Red, homovanillic acid (HVA), o-dianisidine, luminol, OPD, DCFH, ABST, K iodide, or ABTS. In some embodiments, other redox enzymes can be used, for example, the peroxidase IRE APEX2 can be substituted for another enzyme, or peroxidase enzyme which is sensitive to other enzyme products. In some embodiments, transcription factors (TFs) can be used to respond to the produced $H_2O_2$. In some embodiments, OxyR, a TF responsive to $H_2O_2$, can be used to regulate and induce GFP expression downstream of an OxyR binding site. In some embodiments, the redox-responsive probe (RRP) is catalyzed to produce a detectable signal that is fluorescence, or bioluminescence, luminescence or produce an optical readout or detectable signal.

By way of an illustrative example only, in some embodiments, the intermediate redox enzyme (IRE) is a peroxidase enzyme, such as, but not limited to, ascorbate peroxidase (APEX2), and the redox-mediator (Med) is, but not limited to, Amplex® UltraRed (AUR), which produces a fluorescent product only in the presence of hydrogen peroxide ($H_2O_2$) and the peroxidase enzyme as the IRE. In this illustrative example, the hormone biosensor comprising a hormone-catalyzing enzyme which degrades a hormone will produce a fluorescent signal, because the enzyme will produce $H_2O_2$, which is used as a substrate, along with AUR, for the peroxidase enzyme, APEX2 to produce a fluorescent product.

APEX2 is an engineered ascorbate peroxidase enzyme that functions both as an electron microscopy tag, and as a promiscuous labeling enzyme for live-cell proteomics. In some embodiments, APEX2 can be used as an IRE to catalyze the generation of a fluorescent product from Amplex® UltraRed (AUR) only in the presence of hydrogen peroxide ($H_2O_2$). In some embodiments, the assay, methods and composition as disclosed herein can also use modified version of the APEX2 enzyme, e.g., a modified APEX2 enzyme with improved enzyme kinetics or catalyzes a different HRP derivative (e.g., catalyzes a different substrate to AUR).

In some embodiments, the technology encompasses alternative or modified intermediate redox enzymes (IREs), for example, such as modifying the APEX2 enzyme to have improved enzyme kinetics or to use alternative peroxidase enzymes, or HRP derivatives. Additionally, in some embodiments, the redox-mediator, such as AUR, can be replaced with other $H_2O_2$ responsive probes known in the art, for example, but not limited to PY1, PO1, Amplex® Red, homovanillic acid (HVA), luminol, OPD, DCFH, ABST, K iodide, or ABTS. In some embodiments, other redox enzymes can be used, for example, the peroxidase IRE APEX2 can be substituted for another enzyme, or peroxidase enzyme which is sensitive to other enzyme products. In some embodiments, transcription factors (TFs) can be used to respond to the produced H$_2$O$_2$. In some embodiments, OxyR, a TF responsive to H$_2$O$_2$, can be used to regulate and induce GFP expression downstream of an OxyR binding site. In some embodiments, the redox-responsive probe (RRP) is catalyzed to produce a detectable signal that is fluorescence, or bioluminescence, luminescence or produce an optical readout or detectable signal.

In some embodiments of any of the aspects, the one or more fluorescence probes to detect H$_2$O$_2$ is 10-Acetyl-3,7-dihydroxyphenoxazine (N-Acetyl-3,7-dihydroxyphenoxazine or ADHP) (Amplex® Red). 10-Acetyl-3,7-dihydroxyphenoxazine is highly specific and stable. The substrate itself is nearly colorless and nonfluorescent until it is oxidized by H$_2$O$_2$ (reacting in a 1:1 stoichiometry) in the presence of horseradish peroxidase (HRP) to become the highly red fluorescent resorufin.

The structure of 10-Acetyl-3,7-dihydroxyphenoxazine (N-Acetyl-3,7-dihydroxyphenoxazine is as follows:

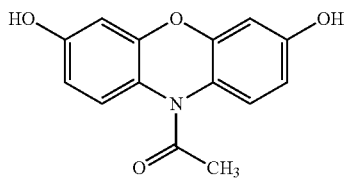

Additionally, in some embodiments, the redox-mediator, such as AUR, can be replaced with other H$_2$O$_2$ responsive probes known in the art, for example, but not limited to PY1, PO1, Amplex® Red, homovanillic acid (HVA), o-dianisidine, luminol, OPD, DCFH, ABST, K iodide, or ABTS.

In some embodiments, other redox enzymes can be used as intermediate redox enzymes, for example, the peroxidase IRE APEX2 can be substituted for another enzyme, or peroxidase enzyme that is sensitive to other enzyme products.

Other intermediate redox enzymes (IRE) are encompassed for use in this assay system can be selected from a nicotinamide adenine dinucleotide (NAD)-dependent dehydrogenase, a flavin adenine dinucleotide (FAD)-dependent oxidase, or a flavin mononucleotide (FMN)-dependent oxidase. For example, in some embodiments, the IRE of this system is selected from 11β-hydroxysteroid dehydrogenase type 2 (11β-HSD-2), glucose oxidase, NAD-glucose dehydrogenase, FAD-glucose dehydrogenase, lactate oxidase, NAD-lactate dehydrogenase, NAD-alcohol dehydrogenase, pyruvate oxidase, NAD-glutamate dehydrogenase, and xanthine oxidase.

C. Electrode(s)

In some embodiments of any of the aspects, the amperometric biosensor, e.g., chronoamperometric biosensor as described comprises at least one electrode. In some embodiments, the hormone biosensor comprises two electrodes. In some embodiments, the hormone biosensor consists of, or consists essentially of two electrodes, a working electrode and a reference electrode, where the working electrode has a redox enzyme deposited on it. In some embodiments, the hormone biosensor does not comprise a third electrode. In some embodiments, the hormone biosensor disclosed herein does not comprise a counter electrode. In some embodiments of any of the aspects, the working electrode comprises a surface, for example to which KSDH1 and optionally, a Readout enzyme can be immobilized as described herein.

In some embodiments of any of the aspects, the electrode is metallic. In some embodiments of any of the aspects, the metallic electrode is gold, silver, platinum, titanium, or palladium. In some embodiments of any of the aspects, the electrode is non-metallic. In some embodiments of any of the aspects, the non-metallic electrode comprises carbon (e.g., glassy carbon).

In some embodiments of any of the aspects, the amperometric biosensor, e.g., chronoamperometric biosensor comprises one electrode referred to herein as a "working electrode." The working electrode is the electrode in an electrochemical system on which the reaction of interest is occurring. Accordingly, herein the hormone biosensor disclosed herein comprises a working electrode comprising KSDH1 enzyme deposited on the working electrode. Typically, the working electrode is often used in conjunction with a counter electrode and a reference electrode in a three electrode system. However, in specific embodiments of the hormone biosensor disclosed herein, the working electrode is used in conjunction with a reference electrode but not the counter electrode. In some embodiments of any of the aspects, the working electrode is coated with the redox mediator (e.g., Prussian blue). In some embodiments of any of the aspects, the redox enzyme (e.g., the hormone degrading enzyme or KSDH1)) is immobilized to the surface of the working electrode with a polymer.

In some embodiments of any of the aspects, the amperometric hormone biosensor, e.g., chronoamperometric biosensor disclosed herein further comprises an auxiliary electrode. As used herein, the term "counter electrode" (also referred to as the "auxiliary electrode") is an electrode used in an electrode electrochemical cell for voltammetric analysis or other reactions in which an electric current is expected to flow.

In some embodiments of any of the aspects, the amperometric hormone biosensor, e.g., chronoamperometric hormone biosensor can optionally comprise a reference electrode. As used herein, the term "reference electrode" is an electrode which has a stable and well-known electrode potential. The high stability of the electrode potential is usually reached by employing a redox system with constant (buffered or saturated) concentrations of each participant of the redox reaction. The counter (or auxiliary) electrode is distinct from the reference electrode, which establishes the electrical potential against which other potentials may be measured, and the working electrode, at which the analyte detection (e.g, hormone detection) by KSDH1 enzyme takes place.

In some embodiments, the hormone biosensor disclosed herein is a two-electrode system (e.g., working and reference electrodes), where either a known current or potential is applied between the working and reference electrodes and the other variable may be measured. The counter electrode functions as a cathode whenever the working electrode is operating as an anode and vice versa. In some embodiments, the counter electrode often has a surface area much larger than that of the working electrode to ensure that the half-reaction occurring at the counter electrode can occur fast enough so as not to limit the process at the working electrode.

As detailed in the Examples, the size of the working electrode may influence the current produced from the hormone biosensor. Accordingly, in some embodiments, the working electrode has an area of >4π mm$^2$. In some embodiments, the size of the working electrode is in the range of 5-8π mm$^2$, or 8-10π mm$^2$, or 10-12π mm$^2$, or 12-15π mm$^2$, or greater than 15π mm$^2$.

In some embodiments, the shape of the working electrode is circular, and in some embodiments the shape is oval. In some embodiments, the reference electrode is a geometric shape which wraps or circles around the working electrode as in the interdigitated electrode (IDE) design.

When a three electrode cell (e.g., working, counter, and reference electrodes) is used to perform electroanalytical chemistry, the auxiliary electrode, along with the working electrode, provides a circuit over which current is either applied or measured. Here, the potential of the counter electrode is usually not measured and is adjusted so as to balance the reaction occurring at the working electrode. This configuration allows the potential of the working electrode to be measured against a known reference electrode without compromising the stability of that reference electrode by passing current over it.

In some embodiments of any of the aspects, the amperometric hormone biosensor, e.g., chronoamperometric biosensor comprises, or consist essentially of, a working electrode and a reference electrode. In some embodiments of any of the aspects, the biosensor can comprise a multi-electrode configuration including a working electrode, a counter electrode, and a reference electrode. In one example, the hormone-catalyzing enzyme (e.g., KSDH1) and optionally, readout enzyme or redox mediator are immobilized on the working electrode. The working electrode can be, for example, carbon, glassy carbon, metal, metal oxides or a mixture of carbon and metal or metal oxides. In one example, the working electrode is a glassy carbon electrode. The reference electrode can be, for example, a saturated calomel reference electrode (SCE), Ag/AgCl, Ag/Ag, or saturated $Hg_2Cl_2$. In some embodiments, the counter or reference electrode can be, for example, a metal such as gold, silver, platinum, titanium, or stainless steel, such as a metal wire counter or reference electrode. In some embodiments, the working and/or the reference electrodes, and optionally the counter electrode are screen printed electrodes (SPE).

The biosensor electrodes, such as active electrodes, can be formed by coating a fine metal wire with a formulation (e.g., comprising the hormone-catalyzing enzyme, e.g., KSDH1 enzyme, redox mediator, and polymer such as chitosan) and drying the coating in place on the wire. For example, a fine platinum wire can be coated with the enzyme-formulation and the coating dried in place. The coated wire can be arranged in a syringe or other suitable flow cell or channel device that can be placed, for example, in-line or into the flow of an analyte stream to be monitored for hormone concentration.

Platinum, silver, carbon, gold, titanium, and Ag/AgCl ink also can be used in screen-printing methods, or photolithographically patterned metal vapor deposition methods, to form film sensors for the fabrication of miniaturized, planar, solid state electrodes. These electrodes can be used in electrode strips, biochips, and other miniaturized sensor configurations. The biosensor can be, for example, a screen-printed (e.g., a screen printed electrode (or SPE)) or photolithographically patterned three-electrode transducer with a carbon or platinum working electrode. In some embodiments, the biosensor can be screen-printed or ink-jet printed as disclosed in WO2019/224628, which is incorporated herein in its entirety by reference. As a non-limiting example, in some embodiments of any of the aspects, the working electrode comprises a Prussian blue screen-printed electrode. See e.g., US patent publication 2008/0160625, PCT publications WO2017210465, WO2018202793A2 Chinese patent publications CN110573868, CN102053161, CN105136885; the contents of each of which are incorporated herein by reference in their entireties. Other transducer configurations also can be used.

Figure 7:
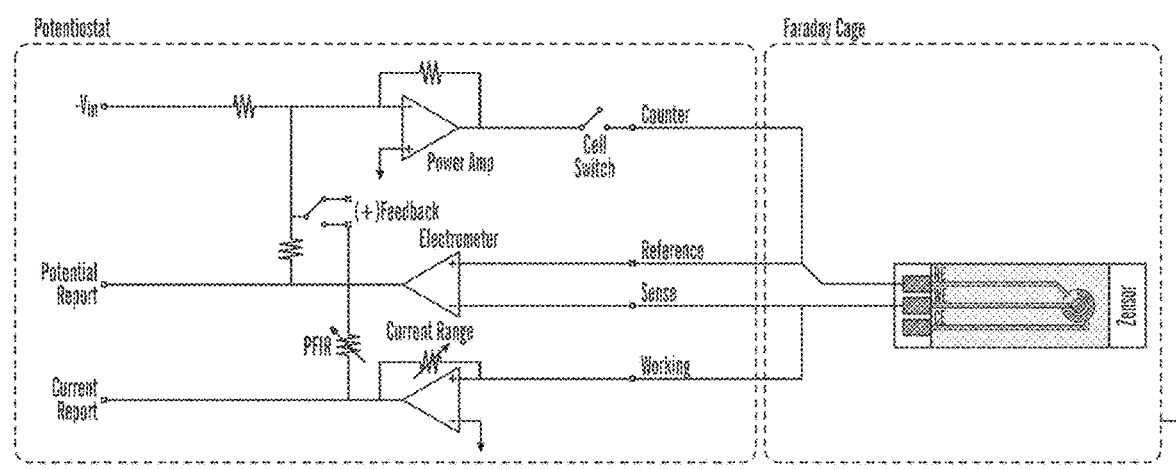
FIG. 7 shows a simplified representation of potentiostat circuitry which allows for the accurate measurement of a current response resulting from analyte addition to the electrochemical biosensor.
Figure 8A:
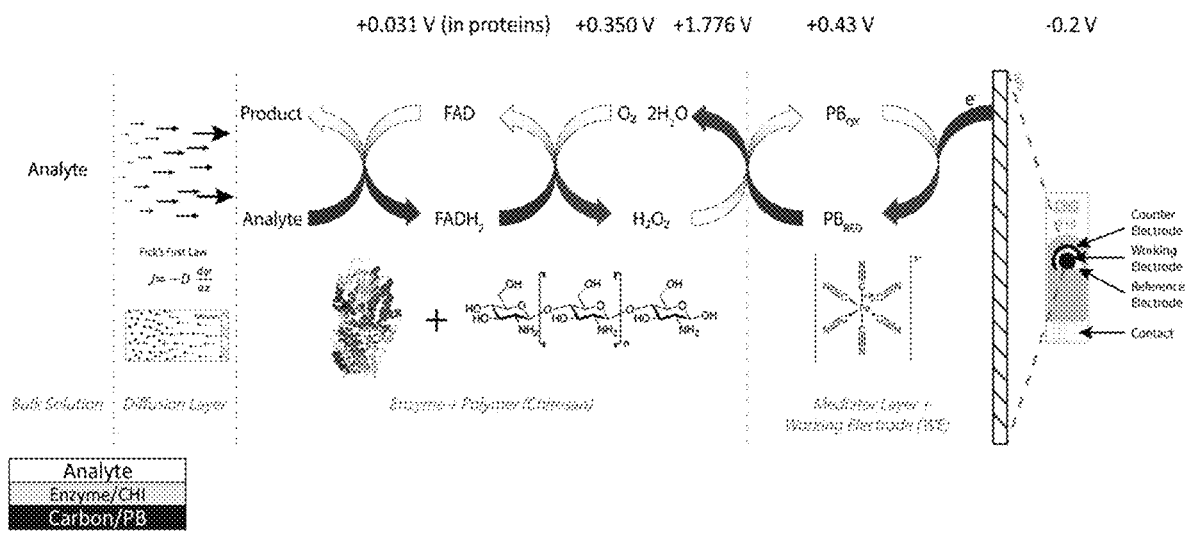
FIGS. 8A-8B show development of an oxidase-based hormone biosensor and limited signal for KSDH1.
Figure 8B:
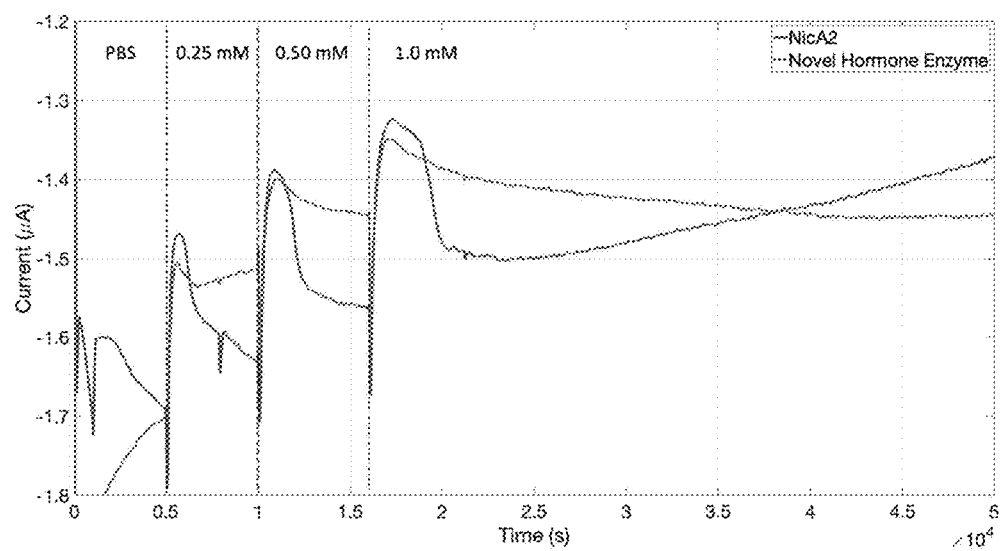

Referring to FIG. 7, in one example, an amperometric hormone biosensor for use herein has the configuration of an electrode test strip having an electrode support layer, a redox-enzyme and redox-mediator coated-working electrode disposed on the support layer, a counter electrode and reference electrode spaced from the working electrode and disposed on the support. A covering layer defines an aperture that opens into a recessed space or well having walls defined by layer and a bottom defined by layer. As shown, the electrodes are situated in the well. The electrodes are left exposed in well, such that sample fluid can be received in well to contact the electrodes. The working electrode comprises a coating of the redox-enzyme and redox-mediator composition immobilized to a conductive electrode material, such as referenced herein. The counter electrode is a conductive electrode material without the coating of the redox-enzyme and redox-mediator composition. The electrode support, typically an elongated strip of electrical insulating polymeric material, e.g., PVC, polycarbonate or polyester, supports two or more printed tracks of electrically conducting carbon ink. These printed tracks define the positions of the working, counter, and reference electrodes, and of the electrical contacts that are operable to be inserted into an appropriate measurement device (not shown; e.g., a potentiostat).

The covering layer also can be an electrical insulating polymeric material. The insulating layers and can be, for example, hydrophobic insulating polymeric material. The electrodes as positioned in the well can be contacted and covered by fluid sample during measurements. In addition to the arrangement shown, the working, counter, and reference electrodes can be arranged in other configurations relative to each other within recess well. The working, reference and counter electrodes can be spaced, for example, from about 0.25 mm to about 0.5 mm, and the working, counter, and reference electrodes can have a width, for example, of about 0.5 mm to 1.5 mm, and a length, for example, of from about 1.5 mm to about 2.5 mm, or other dimensions.

In some embodiments of any of the aspects, the amperometric hormone biosensor, e.g., chronoamperometric biosensor comprises an electrochemical sensor strip. In some embodiments of any of the aspects, the electrochemical sensor strip comprises: an insulation substrate; a first conduction film mounted on the insulation substrate and having a first and a second ends; and an insulation layer mounted on the first conduction film to cover the first end, wherein the second end serves as a signal output terminal, the first end has a first conduction section exposed between the insulation layer and the insulation substrate, and the first conduction section serves as a working surface of an electrode (i.e., working electrode) of the electrochemical sensor strip. See e.g., European patent publication 1845371, the content of which is incorporated herein by reference in its entirety.

In still another aspect of the present invention, the biosensor electrode is contained within a miniaturized device to further facilitate sample quantification. This amperometric microbiosensor comprises several components. First, a metal wire with a working end to be further electroplated with a noble metal serves as the working electrode. This biosensing electrode forms the working electrode about which an encasement is then drawn. The working electrode within the encasement is further drawn to a tip of about 1-20 m in diameter. A Ag/AgCl wire is then inserted into the encasement wherein the Ag/AgCl wire serves both as a reference and counter electrode. Finally, an electrolyte filler is inserted into the encasement to complete the microbiosensor.

D. Detection of Signals

The disclosed technology relates to a biosensor useful for the accurate, reliable and sensitive measurement of hormone in any setting, e.g., a clinical setting.

The redox-enzyme biosensor generates an electrochemically or non-electrochemically detectable product or by-product directly, or alternatively, the enzyme system can also include at least one further component, such as an intermediate redox enzyme (IRE) as disclosed herein. In some embodiments, the further component may be: one or more additional enzyme(s) forming an enzymatic pathway utilizing the product or by-product of the initial redox-enzyme reaction to thereby generate a photometrically or electrochemically detectable product or by-product; or at least one signal mediator; or both the additional enzyme(s) and the signal mediator(s). The signal mediator(s) may be selected from, for example: indicators, such as a pH-change indicators; electron transfer mediators; photometric mediators, and other components.

In some embodiments in an electrochemical embodiment of the assay, the redox-enzyme system utilizes an electrochemically detectable cofactor, such as NADH or FAD, or generates a by-product, such as $H_2O_2$ or electrons directly, during the course of the enzymatic reaction with hormone.

For illustrative purposes only, the oxidase or dehydrogenase enzyme can be conjugated to an electroactive molecule and the analyte probe is attached or on the surface of a conducting surface of a semiconductor device, such that when the oxidase or dehydrogenase enzyme is bound to hormone, the electroconductive molecule conjugated to the oxidase or dehydrogenase enzyme and hormone are in close proximity to allow electron transfer, and the flow of electrons to the semiconductor device which is detected by an increase in current on the surface.

In another embodiment, electrochemical impedance spectroscopy can be used to measure the resistance of the system by using redox markers.

Other methods to modify the oxidase or dehydrogenase enzyme and analyte probes for electrochemical detection of the analyte and generating electroconductive biosensors for use herein are described in Electrochemical methods—Fundamentals and applications, 2Ed., Allen Bard and Larry Faulkner, and Electrochemistry for biomedical researchers, Richie L C Chen, World Scientific Press, each of which are incorporated herein in their entirety by reference.

In some embodiments of any of the aspects, detection of hormone is not limited to electrochemical means, and the redox-enzyme system disclosed herein may employ different detection methods, e.g., UV, fluorescence, or other suitable methods of detecting the target analyte and redox-enzyme interactions.

Non-electrochemical detection of redox-mediators (Med) involves, for example, any calorimetric or photometric detection mode known in the art (for example, any colorimetric, spectrometric, spectrophotometric, luminescence-based, chemiluminescence-based, or fluorescence-based detection method.)

A fluorescence detection device has the following minimum requirements: it must be light-tight to eliminate stray light from its surroundings, its fluorophores must be stored in the dark to prevent photobleaching (that is increase shelf life), and its optics must be at a 900 angle. A diode emitting the desired excitation wavelength can function as the light source, and a PMT can function as the detector. These need not be elaborate since both the excitation and emission λmax of the fluor are known, and these are the only wavelengths required. The same redox-enzyme and redox-mediator used in an enzyme electrochemical device can be used in a fluorescence device. A portable fluorescence detector for aflatoxin has been described in the literature (M A Carlson et al., An automated handheld biosensor for aflatoxin, Biosens. Bioelectr. 14:841 (2000)), so a precedent for a portable fluorescence detector exists.

Both direct and indirect fluorescence allows the detection of hormone and redox-enzyme interactions, via the redox-mediator. The $H_2O_2$-generating systems can use $H_2O_2$ and an additional fluorophore. In these systems, $H_2O_2$ production causes an increase in fluorescence intensity that is proportional to the hormone concentration.

Indirect fluorescence of NADH can be detected using the dye rhodamine 123. In some embodiments, non-radiative energy transfer (also called fluorescence resonance energy transfer, FRET) occurs between the excited states of NADH and rhodamine 123. FRET is a well-known technique for determining the proximity of two species, i.e. FRET is utilized as a "molecular yardstick" both in vitro and in vivo. In this context of the target analyte and redox-enzyme interactions, a donor fluorophore, e.g., NADH, transfers its excited state energies to the acceptor fluorophore, rhodamine 123. (R P Haugland, Handbook of Fluorescent Probes and Research Products, 2002 (9th ed.; Molecular Probes, Inc.; Eugene, Oreg.); K Van Dyke et al., eds. Luminescence Biotechnology. Instruments and Applications, 2002 (CRC Press; Boca Raton, Fla.) and references contained therein). The NADH-rhodamine 123 FRET method has been successfully employed in other enzymatic assays (M H Gschwend et al., Optical detection of mitochondria) NADH content in intact human myotubes, Cell. Mol. Biol. 47:OL95 (2001); H. Schneckenberger et al., Time-gated microscopic imaging and spectroscopy in medical diagnosis and photobiology, Opt. Eng. 33:2600 (1994)). Bioluminescence resonance energy transfer, or BRET, may also be used in conjunction with a hormone-specific enzyme system according to the present invention. In BRET, the donor fluorophore is replaced by a luciferase. Bioluminescence from luciferase in the presence of a substrate excites the acceptor fluorophore. BRET has also been applied in vitro and in vivo (K Van Dyke et al., 2002).

ATP can be derivatized with a fluorophore for indirect fluorescence. Several commercially available dyes include BODIPY ATP and trinitrophenyl ATP (Haugland, 2002). These analogs change their fluorescence intensity or become fluorescent when bound to an enzyme's ATP binding site.

Indirect fluorescence detection of $H_2O_2$ has also been reported (Carr & Bowers, 1980). These methods utilize dyes that reduce the peroxide to $H_2O$ and are themselves oxidized. Homovanillic acid (4-hydroxy-3-phenylacetic acid) and p-hydroxyphenylacetic acid are among the most commonly used in clinical chemistry (Can and Bowers, 1980). A commercially available kit uses the dye Amplex® Red for fluorescence detection of $H_2O_2$(Haugland, 2002).

Any fluorescent dyes and fluorescence-detectable enzyme substrate or cofactor analogs can be used in a fluorescence device to detect hormone and redox-enzyme interactions.

In one embodiment, fluorescent molecule detection can be achieved using a number of detection systems. The choice of a proper detection system for a particular application is well within the abilities of one skilled in the art. Exemplary optical detection system capable of detecting the fluorescence means include, but are not limited to, detection by unaided eye, Fluorescence activated cell sorting (FACS), light microscopy using the eye or an optical sensor as the detector, confocal microscopy, laser scanning confocal microscopy, imaging using quantum dot color, fluorescence spectrum or other quantum dot property and wide-field imaging with a 2 D CCD camera and a high numerical aperture microscope objective. An exemplary laser based microscope system capable of detecting and spectrally resolving the fluorescence from single semiconductor nanocrystals is known in the art.

In some embodiments, the optical detection system may or may not comprise at least one source of excitatory light, such as at least one laser. A source of excitatory light is not needed to detect objects which luminesce independently of light absorption, such as can be generated via bioluminescence or chemiluminescence, for example. In some embodiments, an optical detection system useful herein to measure fluorescence may comprise a light detector detecting light emitted from the object. The light detector is capable of at least partially absorbing light incident thereon and generating output signals in response to the light. The light detector may comprise a control circuit for controlling the operation of the light detector. The control circuit may comprise a circuit of signal amplifier, A/D convertor, integrator, comparator, logic circuit, readout circuit, memory, microprocessor, clock, and/or address.

In some embodiments, the detecting apparatus may comprise a computer for processing output signals from the light detector and generating a determination result. The detecting apparatus may further comprise a blind sheet with a pinhole. The apparatus may further comprise an excitation light source. The object may absorb light emitted from the excitation light source and then emit another light to be detected by the detecting apparatus. The light emitted from the object may have different wavelength than the light emitted from the excitation light source.

In some embodiments, the detection device, e.g., optical sensor or semiconductive device allows point of care testing (POCT), that is, the subject can perform all the relevant step in analyte (e.g., hormone) detection, including obtaining the sample, applying the sample to the biosensor, placement in the reader device (e.g., optical sensor or semiconductive device), which will transmit the results to a mobile device (e.g., a mobile phone or smartphone, ipad, tablet, smartwatch), or other interface, e.g., cloud to be accessed by the subjects clinical practitioner.

Chemiluminescence (CL) and electrogenerated chemiluminescence (ECL) (collectively referred to herein as "(E) CL") are widely used in medical diagnostics and analytical chemistry (C Dodeigne et al., Chemiluminescence as a diagnostic tool: A review, Talanta 2000, 51:415; K A Fahnrich et al., Recent applications of electrogenerated chemiluminescence in chemical analysis, Talanta 2001, 54:531). Enzyme-based (E)CL systems are sensitive and specific, and many CL systems are used with enzyme cycling to detect $H_2O_2$(Dodeigne et al., 2000). (E)CL can detect picomolar (pM; 10-12M) concentrations of analyte over a wide linear range (Dodeigne et al., 2000; Fahnrich et al., 2001). An (E)CL device can be constructed in accordance with the following principles. Since the reaction itself emits light, an (E)CL device does not need a light source. A photomultiplier tube (PMT) can function as the detector; (E)CL is visible to the unaided, dark-adapted eye. A battery can be the power source for ECL. ECL requires electrodes and a source of applied potential. Like a fluorescence detection device, (E)CL devices need to be light tight and their reagents need to be protected from light until use. Also like fluorescence, (E)CL requires derivatized reagents or additional enzymes and reagents to detect hormone. (E)CL devices can be used with disposable strips (B D Leca et al., Screen-printed electrodes as disposable or reusable optical devices for luminol electrochemiluminescence, Sens. Actuat. B. 2001, 74: 190) and can be miniaturized (Y Lv et al., Chemiluminescence biosensor chip based on a microreactor using carrier airflow for determination of uric acid in human serum, Analyst 2002, 127:1176).

An optical electrode (or optrode) can be fabricated using for detection of the target analyte and redox-enzyme interactions according to the present invention. For example, an optrode such as that used in a glucose optrode that uses ECL, may be employed (see C H Wang et al., Co-immobilization of polymeric luminol, iron(II) tris(5-aminophenanthroline) and glucose oxidase at an electrode surface, and its application as a glucose optrode, Analyst 2002, 127:1507)).

The most common CL systems involve the detection of $H_2O_2$ or another reactive oxygen species (Carr & Bowers, 1980; Haugland, 2002; Dodeigne et al., 2000; K Van Dyke et al., 2002) and references contained therein). The classic system is luminol-peroxidase. In basic solution, $H_2O_2$ oxidizes luminol to an excited amino-phthalate ion; the excited amino-phthalate ion emits a 425-nm photon to return to its ground state. When used in medical diagnostics, this reaction is catalyzed with horseradish peroxidase (HRP) (Carr & Bowers, 1980; Dodeigne et al., 2000). Thus any enzyme system that produces $H_2O_2$ or requires a cofactor that can react with additional reagents to form $H_2O_2$ can be used in a CL device. The $H_2O_2$-generating systems described herein can use luminol-HRP directly for hormone detection. These enzyme cycling schemes increase the light emission over time because the substrates are continuously recycled (Dodeigne et al., 2000). While luminol itself is frequently used in CL, its improved analogs can also be used in a CL-based detector according to the present invention, in place of luminol, in order to increase the sensitivity. Examples of such analogs are those described in Carr & Bowers, 1980; and Dodeigne et al., 2000.

NADH detection using CL is a common technique (Dodeigne et al., 2000). For example, in the presence of 1-methoxy-5-methylphenazinium methylsulfate, NADH reduces 02 to $H_2O_2$ which generates light using the luminol-peroxidase system (Dodeigne et al., 2000). For a hormone monitor, the 02 in ambient air is sufficient to detect hormone using this system. NADH also reacts with oxidized methylene blue to form $H_2O_2$ that reacts with luminol (Carr and Bowers, 1980). NADH can also act as a CL quencher. The fluorescence intensity of the substrate ALPDO is decreased in the presence of NADH and HRP (Van Dyke et al., 2002). NADH also can be used with Ru(bpy)3 2+ for ECL (E S Jin et al., An electrogenerated chemiluminescence imaging fiber electrode chemical. sensor for NADH, Electroanal. 2001, 13(15):1287). Rhodamine B isothiocyanate can also be used for ECL detection of $H_2O_2$(Fahnrich et al., 2001). ECL also offers another advantage in that, by use of a properly poised electrode, the electroactive species can be regenerated at the electrode surface. Regeneration both conserves reagents and allows durable and/or "reagentless" sensors. All these systems can be used in a (E)CL device interfaced to a hormone-specific enzyme system according to the present invention.

CL is widely used to quantitate ATP simply and sensitively (Carr & Bowers, 1980). The enzyme luciferase catalyzes the reaction of ATP and luciferin to produce excited-state oxyluciferin, which returns to its ground state with the emission of a 562-nm photon (Carr & Bowers, 1980; Haugland, 2002). The quantum yield for this reaction is very high; 10-14 mol ATP can be detected. A kit for this reaction is commercially available (Haugland, 2002). Because luciferase is the enzyme that causes fireflies to "glow," this reaction is referred to as bioluminescence. Both native and recombinant luciferase are commercially available, and several groups have reported using bioluminescence ATP assays to quantify biological analytes (P Willemsen et al., Use of specific bioluminescence cell lines for the detection of steroid hormone [ant]agonists in meat producing animals, Anal. Chim. Acta 2002, 473:119; S J Dexter et al., Development of a bioluminescent ATP assay to quantify mammalian and bacterial cell number from a mixed population, Biomat. 2003, 24:nb27). In addition to the luminol-HRP system, $H_2O_2$ can also be detected using peroxyoxalic acid derivatives (Dodeigne et al., 2000). $H_2O_2$ can also be detected with CL non-enzymatically with ferricyanide as the catalyst (Dodeigne et al., 2000). In these (E)CL systems, detection of the target analyte and redox-enzyme interactions as described herein either produce $H_2O_2$ or require cofactors that can be utilized to form $H_2O_2$.

Optical biosensors use photometric detection (that is, absorbance, fluorescence) of substrates consumed or products formed by the reaction catalyzed by the enzyme system incorporated into the sensor. The target analyte and redox-enzyme reactions as described may be monitored by several photometric methods-namely by measuring NAD(P)H absorbance at 340 nm for the pyridine nucleotide-dependent enzymes or absorbance of the quinoneimine dye for the $H_2O_2$ forming enzyme systems. For the later, addition of a peroxidase allows detection of $H_2O_2$ by catalyzing the reduction of $H_2O_2$ with concomitant oxidation of a dye compound that upon oxidation absorbs at a specified wavelength. Peroxidase enzymes (for example, commercially available horseradish peroxidase) typically have broad substrate specificities so several different electron donor compounds may be used. NAD(P)H consumption may also be measured by fluorescence detection (excitation at 350 nm and emission at 450 nm).

Calorimetry may be employed as a detection means to detect the target analyte and redox-enzyme interactions according to the present invention. Chemical reactions are typically either exo- or endothermic; that is, they release or absorb heat as they occur. Calorimeters detect and measure this heat by measuring a change in the temperature of the reaction medium (K Ramanathan & B Danielsson, Principles and applications of thermal biosensors, Biosens Bioelectr. 16:417 (2001); B Danielsson, Enzyme Thermistor Devices. In Biosensor Principles and Applications. Vol. 15, pp. 83-105 (L J Blum & P R Coulet, eds.; Bioprocess Technology Series, volume 15; Marcel Dekker, Inc: New York, 1991, pp. 83-105, and references contained therein). Thus, the action of the target analyte (e.g., hormone) and redox-enzyme interactions may be monitored calorimetrically. Calorimeters have been designed that are sensitive enough to detect protein conformational changes, and calorimetry has been used to study many enzymatic reactions in detail (M. J. Todd & J Gomez, Enzyme kinetics determined using calorimetry: a general assay for enzyme activity? Anal. Biochem. 2001, 296:179 (2001)).

The major advantage of calorimetry is the lack of derivatization required for analysis (Danielsson, 1991). Since most reactions involve heat exchange, and this heat is detected, no chromophores, fluorophores, luminophores, "mediators," or other modifications of the analyte are required. Reagents and analytes can be used "as is." This allows the analysis of both reactions that lack a chromophore or fluorophore and/or would be difficult or impossible to derivatize or couple to the generation of an electroactive species.

Miniaturized or chip-based thermosensors have been reported in the literature (Ramanathan & Danielsson, 200:1; B Xie & B Danielsson, Development of a thermal microbiosensor fabricated on a silicon chip. Sens. Actuat. B 6:127 (1992); P Bataillard et al., An integrated silicon thermopile as biosensor for the thermal monitoring of glucose, urea, and penicillin. Biosen. Bioelect. 8:89 (1993)). These devices range from radically arranged thermopiles on freestanding membranes to groups of thermopiles constructed on silicon/glass microchannels. These devices have been used to detect specific, single enzymatic reactions (Danielsson, 1991; Xie & Danielsson, 1992; Bataillard et al., 1993). Moreover, two groups have reported thermosensors for glucose (B Xie et al., Fast determination of whole blood glucose with a calorimetric micro-biosensor, Sens. Actuat. B 15-16:141 (1993); M J Muehlbauer et al., Model for a thermoelectric enzyme glucose sensor, Anal. Chem. 61:77 (1989); B C Towe & E J Guilbeau, Designing Medical Devices, 1998.

II. Hormone Biosensor Devices

In one aspect, described herein is a system comprising a hormone amperometric biosensor, e.g., in some instances, a chronoamperometric hormone biosensor as described herein and a potentiostat. A potentiostat is the electronic hardware required to control a three electrode cell and run most electroanalytical experiments. The system functions by maintaining the potential of the working electrode at a constant level with respect to the reference electrode by adjusting the current at an auxiliary electrode. A potentiostat is a control and measuring device; as such it can be referred to as a power supply unit, a processing unit, and/or a display unit. A potentiostat comprises an electric circuit which controls the potential across the cell by sensing changes in its resistance, varying accordingly the current supplied to the system: a higher resistance will result in a decreased current, while a lower resistance will result in an increased current.

In some embodiments of any of the aspects, the potentiostat allows for chronoamperometry, an electrochemical technique in which the potential of the working electrode is stepped and the resulting current from faradaic processes occurring at the electrode (caused by the potential step) is monitored as a function of time. In some embodiments of any of the aspects, the potentiostat measures the current of the chronoamperometric biosensor. In some embodiments of any of the aspects, the current readings are output onto a display (e.g., a display unit of the potentiostat or a separate display module).

Figure 5A:
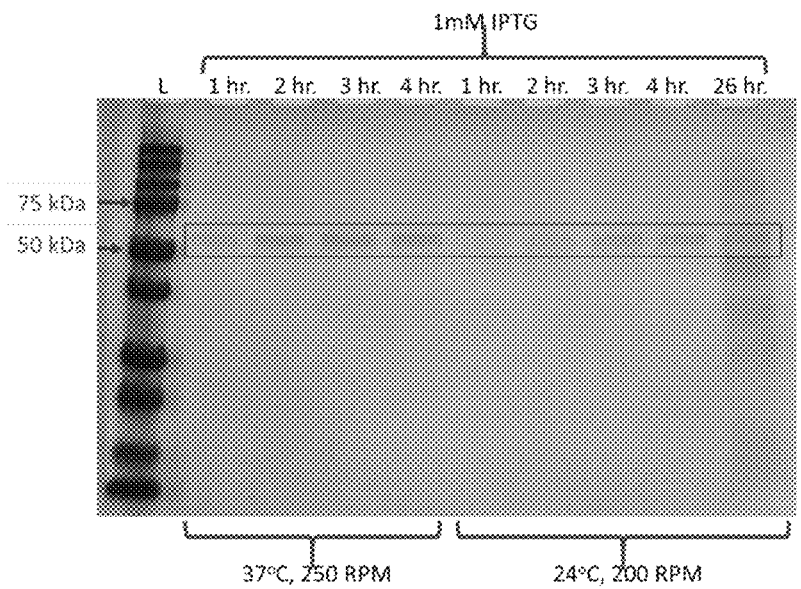
FIGS. 5A-5C illustrate strong protein expression for KSDH1-6×His. KSDH1-6×His (55.30 kDa) has high protein expression at 37° C. for 4 hours; 250 RPM, 37 C until OD 0.6-0.8, then induce to final concentration of 1 mM IPTG; 25 mL volume in 50 mL conical tubes (FIG. 5A). Purification of KSDH1-6×His (55.30 kDa, 250 RPM, 37 C until OD 0.6-0.8, then induce to final concentration of 1 mM IPTG, 500 mL volume in 1 L flask, induction for 4 hours.
Figure 5B:
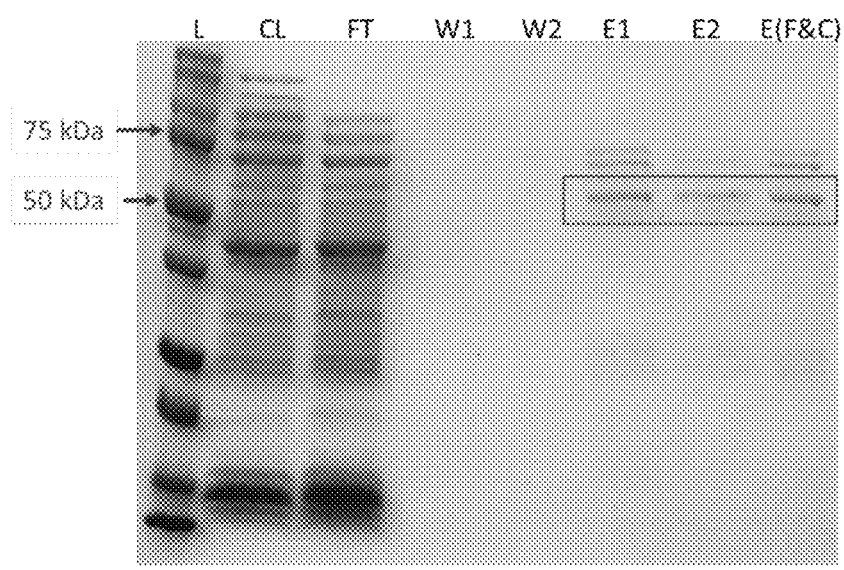
Figure 5C:
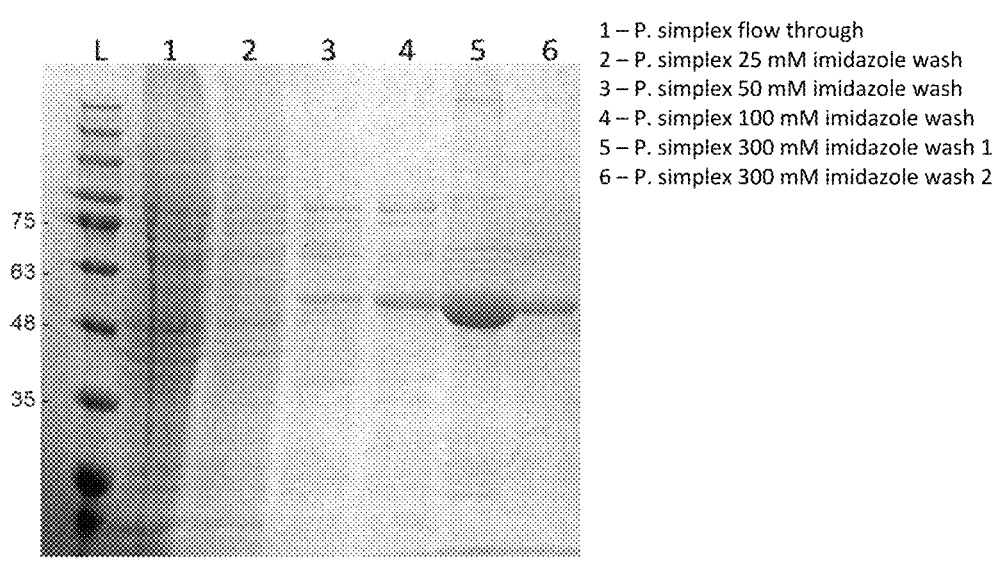

FIG. 5 shows an exemplary system comprising amperometric biosensor, e.g., a chronoamperometric biosensor that is electrically coupled to a potentiostat, for example through electrical leads to at least one electrode of the biosensor. In some embodiments of any of the aspects, the potentiostat is electrically coupled to the working electrode of the biosensor. In some embodiments of any of the aspects, the potentiostat is electrically coupled to the reference electrode of the biosensor. In some embodiments of any of the aspects, the potentiostat is electrically coupled to the counter electrode of the biosensor. In some embodiments of any of the aspects, the potentiostat is electrically coupled to the working electrode and the reference electrode of the biosensor. In some embodiments of any of the aspects, the potentiostat is electrically coupled to the working electrode, reference electrode, and counter electrode of the biosensor.

In some embodiments of any of the aspects, the amperometric biosensor, e.g., chronoamperometric biosensor is contained in a Faraday cage. A Faraday case is a grounded metal screen surrounding a piece of equipment to exclude electrostatic and electromagnetic influences.

In some embodiments of any of the aspects, the system comprises a portable device; as a non-limiting example, the biosensor and/or the potentiostat can be portable. In some embodiments of any of the aspects, the system comprises a wearable device; as a non-limiting example, the biosensor and/or the potentiostat can be wearable. See e.g., US patent publication 2015/0260674, Shiwaku et al., Scientific Report (2018) 8:6368; Steinberg et al., Talanta. 2015 Oct. 1; 143: 178-183; the contents of each of which are incorporated by reference herein in their entireties.

In some embodiments, a hormone biosensor as disclosed herein can be fabricated by using screen-printing technology, or inkjet- or other 3D printing technology to print components of the biosensor, where the biosensor comprises a substrate, e.g., a backing layer, and at least one set of three electrodes. In some embodiments, the electrodes are printed from a conducting polymer onto the backing layer. An exemplary hormone biosensor device useful herein includes a three-electrode geometry which include a reference electrode, a working electrode, which preferably includes a biofunctional polymeric coating, and a counter electrode. Typically, each electrode includes an active area, an electrical interconnect, and a contact area.

The electrodes may have a length between about 2 mm and about 20 mm, a width between about 0.1 mm and about 2 mm, and a height between about 0.1 mm and about 2 mm. The sensors may include an array of sets of three electrodes. The sensor may be connected to a data acquisition system, a display system, or both an acquisition and a display system, forming a sensor system.

In some embodiments, the working electrode includes a coating positioned over its active, and hormone-catalyzing enzyme in or on the coating. The sensor typically includes a sensing area. The sensing area is usually formed of at least a portion of the active areas of the reference electrode, the working electrode, and the counter electrode. In some embodiments, the sensing areas is formed of all of the active area of the reference electrode, all of the active areas of the working electrode and all of the active areas of the counter electrode. In some embodiments, the sensing area may include a protective coating. The contact areas of the reference electrode, the working electrode, and the counter electrode connect the sensor to a data acquisition system, a display system, or both an acquisition and a display system, forming a sensor system. The electrical interconnects that connect the sensing area and the contact areas of the electrodes may include an insulation coating.

The electrodes of the biosensor may be printed from a conducting polymer. Suitable conducting polymers include poly(4,4-dioctylcyclopentadithiophene), poly(isothianapthene), poly (3,4-ethylenedioxythiophene), polyacetylene (PAC), polyaniline (PANI), polypyrrole (PPY) or polythiophenes (PT), poly(p-phenylene sulfide) (PPS), and poly (3,4 ethylenedioxythiophene) polystyrene sulfonate (PEDOT:PSS). The sensing area may include a protective coating. Typically, the protective coating is a polymer that reduces or prevents the non-specific interaction or interference of different molecules in the biological sample with the biofunctional coating of the sensor. The protective coating can be a cation exchange membrane containing a polymer that prevent negatively charged interferences from reaching the sensor surface. Exemplary polymers that may be used as or in a protective coating include polystyrene sulfonate, perfluorinated sulfonated ionomer such as Nafion® (E. I. Du Pont De Nemours And Company Corporation, Wilmington, Del.), AQUIVION® (Solvay SA Corporation, Brussels, Belgium), or a combination thereof.

Typically, the coating includes a mediator, such as a multivalent metal ion or an organometallic compound, and/or a polymer matrix formed of a positively charged polymer such as alginate amine, chitosan, glutaraldehyde, dextran amine, heparin amine, and any combination thereof. The coating also includes a hormone-catalyzing enzyme as described herein, which is capable of oxidizing hormone in a test sample. The coating may also comprise other redox mediators (Med) as described herein, as well as intermediate redox enzymes as described herein having the capability of acting as both electron donors and electron acceptors. Additionally, the coating may also comprise multivalent metal ions such as copper, iron, magnesium, manganese, molybdenum, nickel and zinc, and cofactors such as nicotinamide adenine dinucleotide (NAD+), nicotinamide adenine dinucleotide phosphate (NADP+), ascorbic acid, flavin mononucleotide (FMN), flavin adenine dinucleotide (FAD), coenzyme F420, coenzyme B, Coenzyme Q, glutathione, heme, lipoamide, and pyrroloquinoline quinone. In some embodiments, the sensors may include either electrodes for amperometric tests or cyclovoltammetry.

Generally, the sensor is small enough to be applied onto a medical device or onto a subject. The surface of the biosensor, e.g., the substrate (e.g., backing layer) may be a planar surface, such as a paper, a tattoo, a tape, a textile, a wound dressing or bandage, a medical implant, a contact lens, or a pad. The sensor may be part of a catheter, a contact lens, or a medical implant. The sensor may be worn by a subject on a patch or a bandage, or may be provided in a kit, ready to be used as needed. In some embodiments, the sensor may be inserted in whole or in part into a biological sample such as blood, plasma, serum, urine, saliva, fecal matter, or cervicovaginal mucosa. In some embodiments, the sensor may be connected to a data or signal acquisition system, such as a potentiostat, and, optionally, to a display system. The display system may be a portable display system with a screen to display sensor reading. Portable display systems include smartphones, tablets, laptops, desktop, pagers, watches, and glasses.

Typically, the sensor permits non-invasive detection of a presence, absence, or a concentration of, hormone in a biological sample. Exemplary biological samples include bodily fluids or mucus, such as saliva, sputum, tear, sweat, interstitial fluid, urine, exudate, blood, plasma, or vaginal discharge.

A hormone biosensor comprising a hormone-catalyzing enzyme can be configured according to a biosensor described in WO2019/224628, which is incorporated herein in its entirety by reference.

Printed hormone-catalyzing enzymatic sensors and sensor systems as disclosed herein are capable of detecting hormone concentrations in the relevant range from biological samples obtained non-invasively show long term stability use with accurate and reproducible measurement of hormone levels.

The hormone biosensor device system typically includes a sensor (also referred to as a biosensor), which may be attached to a reader containing an acquisition and/or a display component. The biosensor system is portable, and the acquisition and/or one or more display components may be attached or disconnected from the sensor as needed.

A. Hormone Biosensor

The hormone sensors typically include at least one backing layer, and at least one set of three electrodes printed from a conducting material onto the backing layer. Typically, the electrodes include an active area, an electrical interconnect, and a contact area. The electrodes can be formed from the same conducting material or different conducting materials. Typically, all electrodes are formed from the same conducting material, i.e. a conducting polymer. In some instances, all electrodes can be printed from the same conducting polymer on the backing layer in one step. The combination of the active areas of the reference electrode, the working electrode, and the counter electrode forms the sensing area. Each printed electrode may include 1, 2, 3, 4, 5, 6, 7, 8, 9, or 10 layers of a conducting polymer, for example, but not limited to, poly(3,4-ethylenedioxythiophene) doped with poly(styrene sulfonate) anions (PEDOT PSS), which is widely used in various organic optoelectronic devices. PEDOT: PSS is a blend of cationic polythiopene derivative, doped with a poly anion. In some embodiments, the working electrode with all layers (electrode, dielectric, hormone catalyzing enzyme and redox mediator, and protective coating) can be printed successively.

An exemplary set includes a three electrode geometry with a reference electrode, a working electrode with a biofunctional coating, and a counter electrode. Typically, the electrodes have a length between about 2 mm and about 20 mm, a width between about 0.1 mm and about 2 mm, and a height between about 0.1 mm and about 2 mm.

The sensors may include an array of sets of three electrodes. The sensor may be connected to an acquisition system, a display system, or both an acquisition and a display system. The contact areas of the reference electrode, the working electrode, and the counter electrode may connect the sensor to a data acquisition system, a display system, or both an acquisition and a display system, forming a sensor system.

Generally, the sensors include a coating positioned over a surface of the working electrode, i.e. the active area of the working electrode, and an electron-generating hormone-catalyzing enzyme in the biofunctional coating. The coating may further include a redox mediator and/or a polymer matrix. The sensor may include a sensing area, which is formed of active areas of the reference electrode, the working electrode, and the counter electrode. The sensing area typically includes a protective coating. Typically, the protective coating is a polymer that reduces or prevents the non-specific interaction or interference of different molecules in the biological sample with the biofunctional coating of the sensor. The protective coating may also stabilize the hormone-catalyzing enzyme and/or the redox mediators in the coating. The protective coating can be a cation exchange membrane containing a polymer that prevent negatively charged interferences from reaching the sensor surface. The electrical interconnects that connect the sensing area and the contact areas of the electrodes may include an insulation coating, such as a dielectric coating. The dielectric coating can separate or insulate the sensing area from the contact areas. The sensor system can include a printed metabolite sensor on a backing layer, which can be as simple as a commercial disposable paper. The fabrication of a hormone biosensor as described herein using ink-jet technology or other 3D printing technology enables the production of a highly sensitive, selective, portable, inexpensive, stable, and user-friendly hormone sensing device. The printed hormone biosensor can be tested over a period of one month and its long-term stability confirmed. This demonstrated that the hormone biosensor may be used in real world applications with bodily fluids enabling non-invasive monitoring. In some embodiments, the hormone biosensor as described herein can be configured as an all-polymer "smart e-paper hormone biosensor" providing the next generation of disposable low cost and eco-friendly high-performance hormone biosensor devices.

1. Reference Electrode

The reference electrode is an electrode having a maintained potential, used as a reference for measurement of other electrodes. Exemplary reference electrodes are, but not limited to, silver, silver chloride, silver/silver chloride, gold, copper, carbon, and conducting polymer. The reference electrode may be screen-printed or inkjet-printed from the above-mentioned materials. Typically, the reference electrode is inkjet-printed from a conducting polymer. In some embodiments, the hormone biosensor disclosed herein does not comprise a reference electrode.

2. Working Electrode

The working electrode typically includes a biofunctional coating. The biofunctional coating may contain the hormone-catalyzing enzyme. The biofunctional coating may further include a redox mediator, and optionally an intermediate redox enzyme (IRE) and/or a polymer matrix.

The mechanism of the detection of hormone is based on the specific hormone-catalyzing enzyme and the cycle of electrochemical reactions, which alternatively oxidize/reduce the compounds immobilized at the surface of the sensor, i.e. at the surface of the working electrode. Typically, the electrons are transferred from hormone (the analyte) to the conducting polymer through the cycle of electrochemical reactions, generating a current between the working and counter electrodes detected by the acquisition system. An exemplary cycle of reactions is depicted herein, where upon reacting with hormone, the hormone-catalyzing enzyme, i.e. NE gets reduced, and the reduced hormone-catalyzing enzyme cycles back via the redox mediator, which mediated electron transfer from the hormone-catalyzing enzyme to the conducting polymer, i.e. PEDOT:PSS.

As disclosed herein in the Examples, the inventors that the size of the working electrode influence the current produced from the NicA2 biosensor. Accordingly, in some embodiments, the working electrode has an area of $>4\pi$ mm$^2$. In some embodiments, the size of the working electrode is in the range of 5-8$\pi$ mm$^2$, or 8-10$\pi$ mm$^2$, or 10-12$\pi$ mm$^2$, or 12-15$\pi$ mm$^2$, or greater than 15$\pi$ mm$^2$. In some embodiments, the shape of the working electrode is circular, and in some embodiments the shape is oval. In some embodiments, the counter electrode is a geometric shape which wraps or circles around the working electrode.

In some embodiments, the working electrode comprises NicA2 enzyme in a low- or medium molecular weight (MW) 1% chitosan in 0.5% acetic acid layer. In some embodiments, the working electrode does not comprise Nafion.

Typically, a redox mediator is a small molecule compound participating in an electron donor/acceptance. Exemplary mediators include compounds containing multivalent metal ions such as copper, iron, magnesium, manganese, molybdenum, nickel and zinc, organometallic compounds, phenazine methosulfate, dichlorophenol indophenol, short chain ubiquinones, ferrocene complex, and cofactors such as nicotinamide adenine dinucleotide (NAD+), nicotinamide adenine dinucleotide phosphate (NADP+), ascorbic acid, flavin mononucleotide (FMN), flavin adenine dinucleotide (FAD), coenzyme F420, coenzyme B, Coenzyme Q, glutathione, heme, lipoamide, and pyrroloquinoline quinone. In some instances, the mediator is a ferrocene complex. In some embodiments, a FAD redox mediator is not used.

3. Counter Electrode

The counter electrode, often also called the auxiliary electrode, is an electrode used in a three electrode electrochemical cell for voltammetric analysis or other reactions in which an electric current is expected to flow. Exemplary counter electrodes are, but not limited to, gold, copper, carbon, platinum, titanium, silver, and conducting polymer. The counter electrode may be screen-printed or inkjet-printed from the above-mentioned materials. Typically, the counter electrode is inkjet-printed from a conducting polymer.

4. Materials Forming the Electrodes

Generally, the sensor includes at least one set of three electrodes. Each electrode in the sensor may include one or more coatings. The electrode and the coatings can be inkjet-printed, in sequential manner, to obtain the arrangement described in section Sensors.

Materials forming the electrodes and its coatings include conductive polymers, dielectric inks, charged biocompatible polymers, and synthetic ionic polymers. Typically, the reference electrode, the working electrode, and the counter electrode are formed of conductive polymers. The reference electrode, the working electrode, and the counter electrode may also include a dielectric coating formed of dielectric ink. The working electrode typically includes a biofunctional coating containing a bifunctional molecule, a mediator, and polymer matrix formed of a charged biocompatible polymer. At least a portion, i.e., the active area of the reference electrode, the working electrode, and the counter electrode may be coated with a protective coating containing a synthetic ionic polymer.

a. Conducting Polymer

Conducting polymers which can be used to form the reference electrode, the working electrode, and the counter electrode. Exemplary conducting polymers include poly(3,4-ethylenedioxythiphene) (PEDOT), poly(hydrooxymethyl 3,4-ethylenedioxythiphene) (PEDOT-OH), polystyrene-sulfonate (PSS), F8BT, F8T2, J51, MDMO-PPV, MEH-PPV, PBDB-T, PBDTBO-TPD, PBDT(EH)-TPD, PBDTTT-C-T, PBDTTT-CF, PBTTPD, PBTTT-C14, PCDTBT, PCPDTBT, PDTSTPD, PffBT4T-20D, PffBT4T-C9Cl3, PFO-DBT, Poly([2,6'-4,8-di(5-ethylhexylthienyl)benzo[1,2-b;3,3-b]dithiophene] {3-fluoro-2[(2-ethylhexyl)carbonyl] thieno[3,4-b]thiophenediyl}), Poly(3-dodecylthiophene-2,5-diyl), Poly (3-hexyl thiophene-2, 5-diyl), Poly(3-octylthiophene-2, 5-diyl), PSiF-DBT, poly(triaryl amine) (PTAA), PTB7, TQ1, N2300, P(NDI-T2), poly(diketopyrrolopyrrole) (DPP) poly(benzimidazobenzophenanthroline), poly(2, 5-di (3,7-dimethyloctyloxy)cyanoterephthalylidene), poly(2,5-di (hexyloxy)cyanoterephthalylidene), poly(5-(3,7-dimethyloctyloxy)-2-methoxy-cyanoterephthalylidene), poly(2,5-di (octyloxy)cyanoterephthalylidene), poly(5-(2-ethylhexyloxy)-2-methoxy-cyanoterephthalylidene), poly (4,4-dioctylcyclopentadithiophene), poly(isothianapthene), poly(3,4-ethylenedioxy thiophene), poly acetylene (PAC), polyaniline (PANI), polypyrrole (PPY) or polythiophenes (PT), and poly(p-phenylene sulfide) (PPS). In some instances, the conductive polymer is a combination of two or more conductive polymers described above. For example, the conductive polymer can be poly(3,4 ethylenedioxythiophene):polystyrene sulfonate (PEDOT:PSS).

b. Dielectric Coating

The dielectric coating may be a dielectric/insulator ink layer. The dielectric ink layer may be a dielectric polymer, copolymer, block polymer, or polymer-inorganic composite. The dielectric polymer may be polyimide, polyurethane, polysiloxane, polyacrylate, plyethylene, polystyrene, polyepoxide, polytetrafluoroethylene, polyarelene ether, methylsilsesquioxone, fluorinated polyimide, or a combination thereof. Dielectric polymer-inorganic composite may include a polymer and an inorganic compound such as $BaTi(¾)$, $TiCb$, $Al2O3$, $Zr(¾)$. Exemplary dielectric polymer-inorganic composite may be polyimide-$BaTiO3$.

Commercially available dielectric/insulator inks or pastes may be EMD 6200 (Sun Chemical Corporation, Parsippany, N.J.), KA 701 (DuPont), 125-17, 116-20, 113-48, 111-27, 118-02, 122-01, 119-07, 118-08, 118-12 (CREATIVE MATERIALS®), D2070423P5, D2071120P1, D2140114D5, D2020823P2, D50706P3, D2030210D1, D2070412P3, D2081009D6, D50706D2, D2130510D2 (Sun Chemical Corporation, Parsippany, N.J.), LOCTITE® EDAG 1020A E&C, LOCTITE® EDAG 452SS E&C, LOCTITE® EDAG PD 038 E&C, LOCTITE® EDAG PF 021 E&C, LOCTITE® EDAG PF 455B E&C, or LOCTITE® M 7000 A BLU E&C (Henkel Corporation).

c. Polymer Matrices Immobilizing Hormone-Catalyzing Enzyme

In some instances, the biofunctional coating of the working electrode includes a redox mediator, a hormone-catalyzing enzyme, and a polymer matrix for immobilizing the redox mediator and the hormone-catalyzing enzyme. The polymer matrix can entrap the redox mediator and the hormone-catalyzing enzyme within its matrix to prevent leaking and to improve the processability of the hormone-catalyzing enzyme. The polymer matrix can be biocompatible.

The polymer matrices for immobilizing the mediator and the hormone-catalyzing enzyme may be formed of positively charged polymers, such as alginate amine, chitosan, dextran amine, heparin amine, and any combination thereof.

d. Protective Coating

The protective coating is typically placed on top, e.g., inkjet-printed over, the electrodes, over a portion of the electrodes, and may be the outermost-layer of on the electrodes. The protective coating may be formed of synthetic ionic polymer, such as polystyrene sulfonate and perfluorinated sulfonated ionomers, such as NAFION®, AQUIVION® (Solvay Sa Corporation, Brussels Belgium), or a combination thereof. In some embodiments, NAFION® is not present.

5. Sensing Area

Figure 6A:
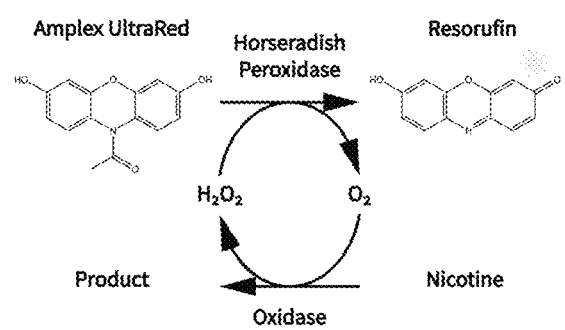
FIGS. 6A-6B are schematics and graphs detailing the Amplex® UltraRed Reagent assay in which fluorescence is analyte limited, not enzyme limited.
Figure 6B:
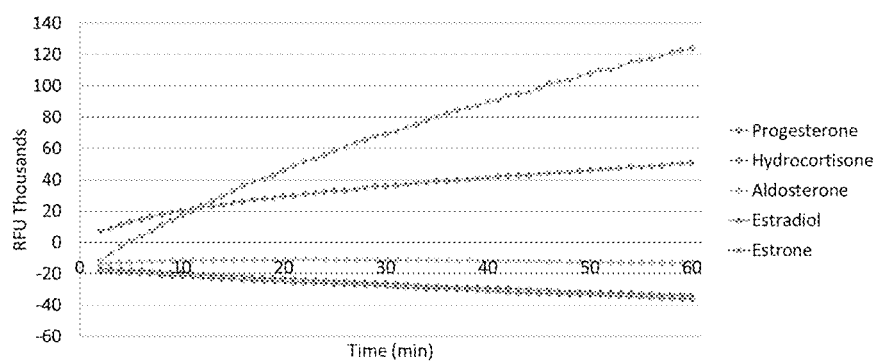

The sensing area of the hormone biosensor as disclosed herein typically includes a portion of the working, counter and reference electrodes, i.e. the active areas of the working, counter, and reference electrodes (FIG. 6B). Typically, the active area of the working electrode containing at least a portion of the biofunctional coating. The sensing area may include a polymer coating. The polymer coating typically reduces or prevents the non-specific interaction or interference of different molecules in the biological sample with the hormone-catalyzing enzyme on the sensor. The polymer coating reduces or prevents any interaction or interference with the electron transport in the sensor from the different molecules in the biological sample.

6. Backing Layer or Substrate

In some embodiments, the surface of the biosensor is a substrate. In some embodiments, the surface of the sensor is a backing layer, and may be a planar surface such as paper, a tattoo, a tape, a textile, a wound dressing or bandage, a medical implant such as catheter, a contact lens, a patch, a pad, glass, or plastics. Typically, the backing layer is a paper. The paper may be disposable after one use or multiple uses, i.e. four times.

7. Wearable Hormone Biosensor

Another aspect of the technology described herein is a wearable hormone biosensor device, for example, an exemplary wearable KSDH1 biosensor device is shown in FIGS.

35A-35B. In some embodiments, a wearable KSDH1 device comprises two parts, an electroconductive part comprising a housing with a removable lid, and within the housing an electric control circuit to control the screen printed electrode (SPE), a battery, and PDMS layer housing a paper channel to wick sweat or interstitial fluid from the skin a subject into the SPE. Magnets or other means can be used to attach the removable lid to the housing. The housing is positioned above or adjacent to a two electrode-screen printed electrode (SPE), where at least one electrode has a KSDH1 enzyme deposited on, where the KSDH1 serves as the hormone biorecognition element, and where the SPE is in fluid communication via the paper channel to a wicking apparatus, where the wicking apparatus contacts the skin of the wearer (i.e., the subject) and wicks sweat or interstitial fluid from the surface of skin of a subject. In particular, the SPE is in fluid communication via a paper channel with a wicking paper, where the wicking paper wicks sweat or interstitial fluid from the skin surface of a subject, and 1) the sweat or interstitial fluid is wicked onto the SPE by the paper channel, and then, 2) sweat or interstitial fluid is drawn towards the sink by capillary action and passed onto of the 2-electrode sensor comprising the KSDH1 biorecognition element, and 3) sweat or interstitial fluid is collected at the sink after measurement. The wearable KSDH1 biosensor has high sensitivity and can repeatedly measure hormone in numerous samples.

In some embodiments, the wearable hormone biosensor can be adapted by one of ordinary skill in the art, including using an adhesive sheet to attach the wicking apparatus to the surface of the wearer's skin, as disclosed in U.S. Pat. No. 9,820,692, or use of sweat collection pads as disclosed in U.S. Pat. Nos. 10,182,795 and 10,646,142, each of which are incorporated herein their entirety by reference.

In some embodiments, a wearable hormone biosensor disclosed herein will not necessarily include all obvious features needed for operation, examples being a battery or power source which is required to power electronics, or for example, a wax paper backing that is removed prior to applying an adhesive patch, or for example, a particular antenna design, that allows wireless communication with a particular external computing and information display device. Several specific, but non-limiting, examples can be provided as follows. In a particular embodiment, a wearable hormone biosensor as disclosed herein is a type of sweat or interstitial fluid sensor device. In some embodiments, the wearable hormone biosensor can take on forms including patches, bands, straps, portions of clothing, wearables, or any mechanism suitable to affordably, conveniently, effectively, intelligently, or reliably bring sweat or interstitial fluid stimulating, sweat or interstitial fluid collecting, and/or sweat or interstitial fluid sensing technology into intimate proximity with sweat or interstitial fluid as it is generated. In some embodiments of the wearable hormone biosensor disclosed herein will require adhesives to the skin, but devices could also be held by other mechanisms that hold the device secure against the skin such as strap or embedding in a helmet. The wearable hormone biosensor disclosed herein may benefit from chemicals, materials, sensors, electronics, microfluidics, algorithms, computing, software, systems, and other features or designs, as commonly known to those skilled in the art of electronics, biosensors, patches, diagnostics, clinical tools, wearable sensors, computing, and product design.

The wearable hormone biosensor disclosed herein may include all known variations of the hormone biosensors disclosed herein, and the description herein shows sensors as simple individual elements. It is understood that many sensors require two or more electrodes, reference electrodes, or additional supporting technology or features which are not captured in the description herein. The wearable hormone biosensor disclosed herein are preferably electrical in nature such as ion-selective, potentiometric, amperometric, and impedance (faradaic and non-faradaic), but may also include optical, chemical, mechanical, or other known biosensing mechanisms. Sensors can allow for continuous monitoring of hormone in the sweat or interstitial fluid of a subject. In some embodiments, a wearable hormone biosensor disclosed herein can be in duplicate, triplicate, or more, to provide improved data and readings. Many of these auxiliary features of the device may, or may not, also require aspects of the present invention.

B. Reader

The biosensors as disclosed herein may be connected to a system, optionally including a display.

a. Acquisition System

In some embodiments, an acquisition system may be a potentiostat, a biosensor, or a galvanostat. In some embodiments, a potentiostat that has a current resolution of as low as 1 pA (100 nA range) is used, for example, a DropSens potentiostat. Typically, the acquisition system is connected to software that converts data into a graph, chart or table, for a compound or molecule such as a metabolite.

b. Display System

The display system may be a portable display system with a screen to display sensor reading. Portable display systems include smartphones, tablets, laptops, and monitors.

c. Packaging

The hormone sensor as disclosed herein may be packaged to protect the electrodes prior to use. Examples of packaging are known in the art and include molded or sealed pouches with temperature and/or humidity control. The pouches may be foil pouches, paper pouches, cardboard boxes, polymeric pouches, or a combination thereof. In some embodiments, the hormone biosensor as disclosed herein, and sensor systems may be packaged as one unit.

Alternatively, in some embodiments, the hormone biosensors may be packaged separately, and used as needed with an acquisition and/or display system provided by the end user.

In some embodiments of the disclosed technology, the system further comprises a computing device, a server, a network, a database and/or a server. As a non-limiting example, data output from the biosensor and potentiostat as described herein can be displayed on a computing device and/or input into a program that may be stored in a database. In some embodiments, the data is wirelessly transmitted from the biosensor and potentiostat to a computing device, such as but not limited to a mobile phone; see e.g., Ainla et al., April 2018 Analytical Chemistry 90(10). The computing device and server may be connected by a network and the network may be connected to various other devices, servers, or network equipment for implementing the present disclosure. A computing device may be connected to a display. Computing device may be any suitable computing device, including a desktop computer, server (including remote servers), mobile device, or other suitable computing device. In some examples, algorithm(s) as described herein and other software may be stored in database and run on server. Additionally, data and data processed or produced by said algorithms or programs may be stored in a database.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present technology as disclosed herein, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Aspects of the assay describe herein rely on catalyzing an electrochemical reaction (redox) of the redox-enzyme biosensor in the presence of hormone. In use, hormone is catalyzed, changing electron flow through the biosensor. In one non-limiting embodiment, the redox-enzyme (or a functional portion thereof) catalyzes a redox event in the presence of hormone. In some embodiments, the redox-enzyme is a hormone-catalyzing enzyme. The redox event can be coupled to a redox-mediator (referred to herein as a "Med") which acts as a conductor of electrons to permit detection of the redox event between hormone and the redox-enzyme biosensor, thereby detecting the presence of the redox-enzyme biosensor. In some embodiments, the redox event between hormone and redox-enzyme can be coupled to an intermediate redox enzyme (IRE), that acts as a conductor of electrons between the first redox event (between hormone and the redox-enzyme biosensor) and the redox-mediator (Med) to permit detection of the activity of the redox-enzyme biosensor reacting with hormone.

In some embodiments, the redox-mediator generates a signal detectable by optical methods, such as, without limitation, fluorescence, surface plasmon resonance, or piezoelectric methods.

Accordingly, described herein is a method of using a biosensor to measure a concentration of a hormone, which comprises providing the hormone biosensor described herein, providing a sample, such as a body fluid sample, and measuring a current produced by the oxidation of a hormone in the sample. In some embodiments, the ketosteroid dehydrogenase enzyme reduces an internal enzyme cofactor that releases electrons to produce an electrochemical signal. In some embodiments, the hormone is hydrocortisone or progesterone.

Embodiments include a method of using an amperometric biosensor, e.g., chronoamperometric biosensor to measure the concentration of hormone comprising: (a) assembling the amperometric biosensor, e.g., chronoamperometric biosensor (or system comprising said biosensor) as described herein; (b) providing a sample; and (c) measuring the current produced by the oxidation of any hormone present in the sample.

The biosensor can be assembled as described herein. As a non-limiting example, described herein is a method of preparing amperometric biosensor, e.g., a chronoamperometric biosensor capable of measuring the concentration of hormone comprising: (a) depositing an electronically active mediator on the electrode surface; (b) depositing a polymer on the electrode surface; and (c) depositing a hormone-catalyzing enzyme on the electrode surface. These steps can occur in any order. In some embodiments of any of the aspects, an electrode is used that already comprises an electronically active mediator on the electrode surface. Accordingly, in another aspect the method of assembling or preparing the biosensor can comprise (a) depositing a polymer (e.g., chitosan or glutaraldehyde) on the electrode surface and (b) depositing a hormone-catalyzing enzyme on the electrode surface. In some embodiments of any of the aspects, the step of assembling the system can comprise electrically coupling the biosensor to a potentiostat and/or other devices such as a portable cellular device.

Variations to the hormone biosensor described herein can include changes to the screen-printed electrodes (SPEs). Changes in size, shape, and material of the SPEs can be made to yield a similar result or improve the biosensor. Also, changes to the matrix which holds the hormone-catalyzing enzyme can be made. Using a two or three electrode circuit with the potentiostat can affect the current response. Furthermore, the choice of a potentiostat for sensitivity to current can improve the biosensor. Mediators on the SPE can be changed or optimized by changing the ions concentrations that constitutive it to yield a higher current response and thus increase sensitivity of the biosensor.

C. Methods of Making the Sensors and the Sensor Systems

In some embodiments, inkjet technology may be used in all the steps for the fabrication of a hormone biosensor as disclosed herein, according to the methods disclosed in international patent application WO2019/224628, which is disclosed herein in its entirety by reference. Other additive printing technologies, such as screen printing or inkjet printing can also be used and yields high performance hormone biosensor devices.

For the deposition of the electronic components as well as the biological layers (such as hormone-catalyzing enzyme for the detection of hormone), inkjet technology not only allows for the controlled deposition of a variety of different materials but also constitutes a low temperature process which is a critical factor when it comes to the integration of biological molecules such as enzymes. Ink jetting enables the patterning of customizable geometries and can easily be integrated in roll-to-roll processes.

A general method of making the sensors include using a conducting polymer ink dedicated for inkjetting and adjusting the ink formulation to meet the substrate requirements for the formation of a uniform and conducting layer. For example, a cross linker, i.e. 3-glycidoxypropyltrimethoxysilane (GOPS) and/or a surfactant, i.e. dodecyl benzene sulfonic acid (DBSA) may be added to the conducting polymer ink to prevent delamination of the conducting pattern from the backing layer and to improve the wettability of the ink and film formation during printing, respectively. The cross linker can be added at a concentration between about 0.01 wt % and about 5 wt %, between about 0.1 wt % and about 5 wt %, between about 0.5 wt % and about 5 wt %, between about 0.5 wt % and about 4 wt %, between about 0.5 wt % and about 2 wt %, between about 1 wt % and about 5 wt %, and between about 0.1 wt % and about 1 wt %. In some instances, the cross linker can be added at a concentration of about 1 wt %. In some instances, the cross linker is absent. The surfactant can be added at a concentration of between about 0.01% (v/v) and about 10% (v/v), between about 0.05% (v/v) and about 10% (v/v), between about 0.10% (v/v) and about 10% (v/v), between about 0.1% (v/v) and about 0.5% (v/v), between about 0.1% (v/v) and about 0.4% (v/v), and between about 0.2% (v/v) and about 0.5% (v/v). In some instances, the surfactant can be added at a concentration of about 0.4% (v/v). The ink may be printed on most planar surface, including paper, such as a commercial glossy paper. The ink is printed on the planar surface to form all three electrodes (e.g. reference, working and counter electrodes) in the set. All electrodes in the set may be formed of the same material or different materials. Typically, all the electrodes in the set are formed of the same conducting polymer. All electrodes can be printed in a single step.

To insulate/separate the sensing area from the contact areas, one, two, three, or more layers of dielectric ink may be printed on top of the electrodes. In some instances, the dielectric ink is printed over a surface of at least one of the electrodes in a set of electrodes. In some instance, the dielectric ink is printed over a surface of all three electrodes in a set of electrodes. In some instances, the dielectric ink is printed over the electrical interconnects of the working, reference, and counter electrodes. Typically, the dielectric ink is UV-curable.

For the biofunctionalization of the sensor, a biological ink containing a mediator (e.g. ferrocene), a polymer matrix, (e.g., chitosan, a polymer for forming a biocompatible matrix and entrapping the mediator in a polymeric biocompatible matrix) and the hormone-catalyzing enzyme, is printed on top of the working electrode to form a biofunctional coating. The hormone-catalyzing enzyme may be immobilized on or in the polymer matrix via non-covalent or covalent bonding, such as via chemical conjugation, e.g., EDC-NHS coupling reaction where carboxyl groups of the enzyme may be conjugated to the amine groups of the polymeric matrix. In some instances, both the redox mediator and the hormone-catalyzing enzyme are physically entrapped in the polymer matrix. In some instances, the hormone-catalyzing enzyme are covalently immobilized on or in the polymer matrix and the mediator is physically entrapped in the polymer matrix. This typically forms the biofunctional coating of the working electrode.

A protective coating may be applied onto the electrodes, including onto the biofunctional coating, by printing a coating polymer on top of the electrodes. The protective coating may be printed on the entire surface of the electrodes, including on the biofunctional coating of the working electrode, or on a portion of the electrodes and on a portion of the biofunctional coating of the working electrode. In some instances, the protective coating is printed on the active areas of the working, reference, and counter electrode. In some instances, the protective coating is printed on the active area of the working electrode. In some instances, the protective coating is printed on the biofunctional coating of the working electrode.

For example, the coating polymer or a polymer mixture, such as a mixture containing Nafion® may be printed on top of the sensing area (comprising the active areas of the working, counter and reference electrodes) to block the interferences present in biologic milieu/media such as saliva or sweat.

An acquisition system, such as a potentiostat, is commercially available. It may be attached to the sensor by connecting each electrode to a lead in the acquisition system. The acquisition system may then be connected to a display system, such as a device with a display screen. Exemplary display systems include smartphones, tablets, laptops, desktops, and smartwatches, are commercially available. The display systems typically include electronic conversion means, such as software, to convert the signals received from the acquisition system to a concentration value or a graph, which is then displayed on the screen. Such conversion means are known in the art.

III. Uses and Applications of the Hormone Biosensor devices

In some embodiments of any of the aspects, the sample analyzed by the hormone biosensor as described herein is preferably a fluid, which is contacted with the electrode surface. That is, a fluid sample contacts the KSDH1 present on the substrate, and if hormone is present in the fluid sample, it relays a redox event that is transmitted to the electrons as describe above. As a non-limiting example, a liquid sample can be applied to the area of the biosensor comprising at least one electrode. In some embodiments of any of the aspects, a non-liquid sample can be transformed into a liquid sample; as a non-limiting example a solid or gaseous sample can be dissolved in a liquid, such as an aqueous solvent that does not interfere with the redox reactions.

The term "sample" or "test sample" as used herein denotes a sample taken or isolated from a biological organism, e.g., a blood or plasma sample from a subject. In some embodiments of any of the aspects, the present invention encompasses several examples of a biological sample. In some embodiments of any of the aspects, the biological sample is cells, or tissue, or peripheral blood, or bodily fluid. Exemplary biological samples include, but are not limited to, a biopsy, biofluid sample; blood; serum; plasma; urine; sperm; mucus; tissue biopsy; organ biopsy; synovial fluid; bile fluid; cerebrospinal fluid; mucosal secretion; effusion; interstitial fluid; sweat; saliva; and/or tissue sample etc. The term also includes a mixture of the above-mentioned samples. The term "test sample" also includes untreated or pretreated (or pre-processed) biological samples. In some embodiments of any of the aspects, a test sample can comprise cells from a subject. In some embodiments of any of the aspects, the test sample can be sweat, interstitial fluid; urine, saliva, or blood (e.g., whole blood, plasma, or serum).

The test sample can be obtained by removing a sample from a subject, but can also be accomplished by using a previously isolated sample (e.g. isolated at a prior time point by the same or another person).

In some embodiments of any of the aspects, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments of any of the aspects, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments of any of the aspects, the test sample is a clarified test sample, for example, by centrifugation and collection of a supernatant comprising the clarified test sample. In some embodiments of any of the aspects, a test sample can be a pre-processed test sample, for example, supernatant or filtrate resulting from a treatment selected from the group consisting of centrifugation, homogenization, sonication, filtration, thawing, purification, and any combinations thereof. In some embodiments of any of the aspects, the test sample can be treated with a chemical and/or biological reagent. Chemical and/or biological reagents can be employed, for example, to protect and/or maintain the stability of the sample during processing. The skilled artisan is well aware of methods and processes appropriate for pre-processing of biological samples required for determination of the level of an analyte as described herein (e.g., hormone).

In some embodiments of any of the aspects, the methods described herein can further comprise a step of obtaining or having obtained a test sample from a subject. In some embodiments of any of the aspects, the subject can be a human subject. In some embodiments of any of the aspects, the subject can be a subject in need of hormone monitoring.

In some embodiments of any of the aspects, measuring the current produced by the oxidation of any hormone present in the sample allows for the determination of the concentration of hormone. In some embodiments of any of the aspects, a known concentration of hormone results in a predictable current, thus an unknown hormone concentration can be determined using a known current and a standard curve of currents at known hormone concentrations.

As described herein, the current of the amperometric biosensor, e.g., chronoamperometric biosensor is not altered in the presence of an interferent. Such interferents can include but are not limited to L-(+)-lactic acid, ascorbic acid, uric acid, dopamine, (−)-epinephrine, creatinine, S-(+)-glucose, sodium, calcium, magnesium, potassium, phosphate, albumin, and amino acids.

A. Methods of Using the Sensors

The hormone biosensor system described herein may be portable, wearable, or attachable to a subject. In some aspects, the sensor is small enough to be applied onto a medical device or onto a subject. In some embodiments, the hormone biosensor has a backing layer which may be a planar surface, such as a paper, a tape, a bandage, a catheter, a lens, a patch, an implant, or a pad. The hormone biosensor, therefore, may be part of a contact lens, or a medical implant or patch. In some embodiments, the hormone biosensor as disclosed herein may be worn by a subject as a patch or on a bandage, or may be provided in a kit, ready to be used as needed.

The sensor may be connected to an acquisition system, such as a potentiostat, and, optionally, to a display system. The display system may be a portable display system with a screen to display sensor reading. Portable display systems include smartphones, tablets, laptops, desktop, pagers, watches, and glasses.

An exemplary method of use includes applying a test sample, e.g., a fluid biological sample onto the sensing area of the sensor, and obtaining a reading indicating that hormone is detected. Optionally, a polymeric well is used on top of the sensing area of the hormone biosensor to confine the test sample. Alternatively, if an acquisition system and/or a portable system is used, the method may include also obtaining a concentration of hormone in the sample.

The information obtained from the sensors or sensor systems may be used to determine levels of hormone in a subject, or metabolism of hormone in a subject.

In some embodiments, the disclosed hormone biosensor is an implantable device. More particularly, the disclosed hormone biosensor is designed to provide, and in conjunction with a suitable signal processing unit, a current which is proportional to the concentration of the analyte of interest, e.g., hormone. In some embodiments, the disclosed hormone biosensor may be implanted in vivo, including intra-cerebral, sub-cutaneous, intra-muscular, inter-peritoneal oral, serum, and vascular implantation, for systemic monitoring and used to monitor hormone levels in the subject in real-time. In some embodiments, the disclosed hormone biosensor can be joined, or electronically coupled with one or more other biosensors, to allow for the simultaneous recording of hormone and one or more multiple analytes of interest. In addition to the in vivo applications, the disclosed hormone biosensor may also find use in medical monitoring.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val;

Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As used herein, the term "biological sample" refers to a sample obtained from a subject. The sample may be from a subject who has been treated with a drug, or may be from an untreated or drug naïve subject. Exemplary samples include, but are not limited to serum, plasma, cell lysate, milk, saliva, vitreous fluid, and other secretions, synovial fluid, peritoneal cavity fluid, lacrimal fluid, and tissue homogenate. In some embodiments, the sample is a bodily fluid, including interstitial fluid, sweat, blood, cerebrospinal fluid (CSF), plasma, whole blood, serum, semen, synovial fluid, saliva, vaginal lubrication, breast milk, amniotic fluid, urine, human feces, phlegm tears, saliva, lymph, peritoneal intracellular fluid, or an original tissue from fetuses, newborn babies, children, teenagers, adults or animals. Moreover, the sample can be in various forms including but not limited to a liquid, frozen, chilled, lyophilized sample. The sample may be subjected to additional purification or treatment steps prior to and/or following the affinity purification step herein.

As used herein, the term "analyte" refers to a substance which is catalyzed by the candidate redox-enzyme biosensor. In some embodiments, an analyte can be a "biological marker" or "biomarker", which is an analyte in a biological system and may be used as an indicator of the risk or progression of disease.

The term "redox" or "oxidation-reduction" or "oxidoreduction" reaction describes any reaction in which electrons are transferred from one molecule, compound, molecular group, etc. to another. The process of oxidation occurs in conjunction with (is coupled with) a reduction reaction, thus resulting in the transfer of electrons.

As used herein, a "redox enzyme" or "oxidoreductase" or "dehydrogenase" are used interchangeably herein and refer to an enzyme that catalyzes a reaction with one or more enzyme substrate(s), resulting in generation or utilization of electrons. The oxidoreductases or dehydrogenase (redox) enzyme reaction and the electrode coupling method has become attractive to develop biosensors. In particular, for a range of substrates, i.e., glucose (i.e., glucose oxidase and glucose dehydrogenase reaction, respectively), electrochemical detection reduced coenzyme nicotinamide adenine dinucleotide (NADH) or hydrogen peroxide has been used galvanometer biosensor. In some instances, redox enzymes employ no prosthetic group, such as those that use reversible formation of a disulfide bond between two cysteine residues, as in the case of thioredoxin. Other redox enzymes use prosthetic groups, such as flavins, NAD, transition metal ions or clusters of such metal ions, etc. The use of the transition metal ions in these enzymes is due to their ability to attain multiple oxidation and spin states.

As used herein, the term "oxidase" refers to an enzyme that catalyzes an oxidation-reduction reaction, especially one involving dioxygen ($O_2$) as the electron acceptor. In reactions involving donation of a hydrogen atom, oxygen is reduced to water ($H_2O$) or hydrogen peroxide ($H_2O_2$).

As used herein, the term "biosensor device" refers to an analytical device which integrates a biorecognition element (e.g., the hormone-catalyzing enzyme) with a physical transducer to generate a measurable signal proportional to the concentration of an analyte (e.g., hormone) recognized by the biorecognition element (e.g., the hormone-catalyzing enzyme). In some embodiments, the biosensor is also referred to as a "sensor" and can be described as device containing elements required for generating an electrical current when a biological sample is applied to the sensor. The sensor may include additional elements, such as an acquisition system and/or a display system, forming a sensor system.

As used herein, the terms "redox molecule", "redox mediator" and "electroactive molecule" are used interchangeably herein and relate to any molecule that is able to undergo an electrochemical reaction. Upon which one or more electrons are either added to or removed from the molecule, converting it into a different oxidative state. For example, 1,4-Benzoquinone is an electroactive molecule that can be converted to hydroquinone upon the reduction of the molecule with an addition of two electrons and two protons according to a specific embodiment.

As used herein, the term "metabolite" refers to a small molecule formed during or after a metabolic reaction, or a metabolic pathway.

As used herein, the term "detection" or "detecting" in the context of detecting hormone using a sensor, refers to an act of obtaining a value or a reading indicating the presence or absence of the hormone in a sample. The detection may require a comparison of the obtained value or reading for a hormone from a test sample to a value or reading obtained from a control sample for hormone and tested in the same way as the test sample.

As used herein, the term "redox mediator" as refers to a molecule capable of participating in an electron exchange between hormone, a hormone-catalyzing enzyme, and/or the conducting polymer. As used herein, the term "biofunctional" in the context of a molecule or a coating refers to a property of the molecule or the coating capable of electron exchange.

As used herein, the term "planar surface" refers to a surface with a region that is sufficiently planar, i.e., sufficiently flat, over a surface area sufficient to accommodate an electrode. For example, if a planar surface is a contact lens, the contact lens has a sufficiently planar region to accommodate an electrode having a length of about 2 mm, and a width of about 2 mm.

As used herein, the term "ink" refers to a solution or suspension of a material to be deposited using inkjet printing onto a surface, such as a conducting polymer or metal, or a polymeric coating As used herein, the term "open reading frame" refers to a reading frame that has the ability to be translated. An ORF is a continuous stretch of codons that begins with a start codon (usually AUG) and ends at a stop codon (usually UAA, UAG or UGA). An ATG codon (AUG in terms of RNA) within the ORF (not necessarily the first) may indicate where translation starts. The transcription termination site is located after the ORF, beyond the translation stop codon. If transcription were to cease before the stop codon, an incomplete protein would be made during translation. In eukaryotic genes with multiple exons, introns are removed and exons are then joined together after transcription to yield the final mRNA for protein translation. In the context of gene finding, the start-stop definition of an ORF therefore only applies to spliced mRNAs, not genomic DNA, since introns may contain stop codons and/or cause shifts between reading frames. An alternative definition says that an ORF is a sequence that has a length divisible by three and is bounded by stop codons.

In some embodiments, a polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to an assay known in the art or described below herein. A functional fragment can comprise conservative substitutions of the sequences disclosed herein.

In some embodiments, a polypeptide described herein can be a variant of a polypeptide or molecule as described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity of the non-variant polypeptide. A wide variety of PCR-based site-specific mutagenesis approaches are known in the art and can be applied by the ordinarily skilled artisan.

As used herein, the term "affinity" refers to the strength of the binding interaction between a single biomolecule (e.g. a redox-enzyme) to it substrate or analyte.

As used herein, a "nucleoside" is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

As used herein, the term "small molecule" refers to low molecular weight molecules (<900 Daltons) that include lipids, monosaccharides, second messengers, other natural products and metabolites, as well as drugs and other xenobiotics. They are distinct from macromolecules such as proteins. A small molecule is able to enter cells easily because it has a low molecular weight. Once inside the cells, it can affect other molecules, such as proteins. This is different from drugs that have a large molecular weight, such as monoclonal antibodies, which are not able to get inside cells very easily.

As used herein, the term "conjugate" or "conjugation" refers to the attachment of two or more entities to form one entity. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art.

As used herein, the term "ligand" refers to a substance that forms a complex with a biomolecule to serve a biological purpose. In protein-ligand binding, the ligand is usually a molecule, which produces a signal by binding to a site on a target protein. The binding typically results in a change of conformational isomerism (conformation) of the target protein. In DNA-ligand binding studies, the ligand can be a small molecule, ion, or protein, which binds to the DNA double helix. The relationship between ligand and binding partner is a function of charge, hydrophobicity, and molecular structure. The instance of binding occurs over an infinitesimal range of time and space, so the rate constant is usually a very small number.

As used herein, the term "binding" refers to an association between proteins or nucleotides that occurs through intermolecular forces, such as ionic bonds, hydrogen bonds and Van der Waals forces. The association of docking is actually reversible through dissociation. Measurably irreversible covalent bonding between a ligand and target molecule is atypical in biological systems. Ligand binding to a receptor protein or to an allosteric transcription factor can alter the conformation by affecting the three-dimensional shape orientation. The conformation of a receptor protein or allosteric transcription factor composes the functional state. Ligands include small molecules, hormones, inhibitors, activators, and neurotransmitters.

As used herein, the term "fluorescent molecule" refers to a fluorescent chemical compound that can reemit light upon light excitation. Fluorescent molecules typically contain several combined aromatic groups, or planar or cyclic molecules with several 71 bonds. Current fluorescence imaging probes typically consist of single conventional fluorophore (e.g., organic dyes, fluorescent proteins), fluorescent proteins (e.g., GFP) and semiconductor quantum dots (Q-dots). Single fluorophores are usually not stable and have limited brightness for imaging. Similar to dyes, the fluorescent proteins tend to exhibit excited state interactions which can lead to stochastic blinking, quenching and photobleaching. Fluorescent molecules are known in the art and include florescent proteins (e.g. CAP, WFP, BFP, and other GFP derivatives). Other suitable fluorescent molecules are known in the art and commercially available from, for example, Molecular Probes (Eugene, Oreg.). These include, e.g., donor/acceptor (i.e., first and second signaling moieties) molecules such as: fluorescein isothiocyanate (FITC)/tetramethylrhodamine isothiocyanate (TRITC), FITC/Texas Red™ Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X (ROX), FITC/tetramethylrhodamine (TAMRA), and others. In addition to the organic fluorophores already mentioned, various types of nonorganic fluorescent labels are known in the art and are commercially available from, for example, Quantum Dot Corporation, Inc. Hayward Calif.). These include, e.g., donor/acceptor (i.e., first and second signaling moieties) semiconductor nanocrystals (i.e., 'quantum dots') whose absorption and emission spectra can be precisely controlled through the selection of nanoparticle material, size, and composition.

As used herein, the term "device" refers to an electrically addressable unit that performs some task, such as switching, storing a single bit of information, or sensing a particular molecule or class of molecules according to an embodiment of the present invention. Depending upon the embodiment, other examples of definitions also exist.

As used herein, the term "circuit" refers to a group of devices, each of which are designed to carry out similar tasks according to a specific embodiment. For example, a transistor is a switching device. A multiplier is a logic circuit constructed from many transistors, which is a circuit. As another example, a nanowire is a chemical sensing device. An array of nanowires each coated with a different molecular probe, constitutes a sensor circuit designed to sense many different molecular targets according to a specific embodiment. Depending upon the embodiment, other examples of definitions also exist.

The term "percent (%) amino acid sequence identity" or "% sequence identity to amino acids" with respect to a particular SEQ ID NO is defined as the percentage of amino acid residues in a candidate sequence that are identical with the amino acid residues in the comparative sequence identified by the SEQ ID NO, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996); available on the world wide web at blast.wustUedu/blast/README.html). WU-BLAST-2 uses several search parameters, most of which are set to the default values. The adjustable parameters are set with the following values; overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "integrated circuit" refers to a group of circuits, each design to carry out different specific tasks, but operating together to perform some larger function. For example, a multiplier circuit can retrieve two numbers from a memory circuit, multiply them together, and store them back into the memory circuit. Depending upon the embodiment, other examples of definitions also exist.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A biosensor for the measurement of the concentration of hormone comprising:
   a. an electrode comprising a surface;
   b. optionally, an electronically active mediator (Med) deposited on the surface of the electrode; and
   c. a hormone-catalyzing enzyme deposited on the surface of the electrode, wherein the hormone-catalyzing enzyme catalyzes a hormone to produce electrochemical signal.
2. The biosensor of paragraph 1, wherein the hormone-catalyzing enzyme is recombinant KSDH1 or a functional variant or fragment thereof.
3. The biosensor of paragraph 2, wherein the hormone-catalyzing enzyme, e.g., KSDH1 is encoded by a nucleic acid comprising a sequence that is at least 90% identical to SEQ ID NO: 1.
4. The biosensor of any of paragraphs 1-3, wherein the hormone is progesterone or hydrocortisone.
5. The biosensor of paragraph 2, wherein the hormone-catalyzing enzyme, e.g., KSDH1, comprises an amino acid sequence that is at least 95% identical to SEQ ID NO: 2.
6. The biosensor of any of paragraphs 1-5, wherein the hormone-catalyzing enzyme KSDH1 is immobilized on the electrode with a polymer, and in some embodiments, the polymer contacts the surface of the working electrode, and in some embodiments, there is an optional top layer over (i.e., on top of) the polymer layer, where the top layer does not comprise Nafion, and in some embodiments, the top layer comprises Prussian-Blue (PB).
7. The biosensor of any of paragraphs 1-6, wherein the polymer comprises a low molecular weight (LMW) or medium molecular weight (MMW) 1% chitosan in 0.5% acetic acid, or LMW or MMW chitosan in acetic acid at concentration between 0.1%-05% or 0.5%-1.5%, and optionally, the polymer also comprises Prussian Blue (PB).
8. The biosensor of any of paragraphs 1-7, wherein in the presence of hormone, the KSDH1 enzyme releases electrons to produce an electrochemical signal, wherein the electrochemical signal is detected by current passed to the electrode.
9. The biosensor of any of paragraphs 1-8, wherein the electronically active mediator (Med) can be oxidized from a reduced form ($Med_{red}$) to an oxidized form ($Med_{ox}$), wherein the $Med_{ox}$ produces a detectable signal.
10. The biosensor of any of paragraphs 1-7, wherein the detectable signal is produced when a hormone is catalyzed by the hormone-catalyzing enzyme and transfers at least one electron from $Med_{red}$, resulting in its reduction to $Med_{ox}$.
11. The biosensor of any of paragraphs 1-8, wherein the electronically active mediator $Med_{ox}$ is reduced by the electrode, producing a detectable signal.
12. The biosensor of any of paragraphs 1-11, wherein the $Med_{ox}$ produces an electrochemical signal, wherein the electrochemical signal is detected by current passed to the electrode.
13. The biosensor of any of paragraphs 1-12, wherein the detectable signal is electrochemical and/or colorimetric.
14. The biosensor of any of paragraphs 1-13, wherein the biosensor is an amperometric biosensor and the detectable signal is electrochemical.
15. The biosensor of any of paragraphs 1-14, wherein the electrode is connected to a potentiostat having a current resolution to at least 1 pA (100 nA).
16. The biosensor of any of paragraphs 1-15, wherein the biosensor comprises a working electrode and a reference electrode.
17. The biosensor of any of paragraphs 1-16, wherein the biosensor does not comprise a counter electrode.
18. The biosensor of any of paragraphs 1-17, wherein the working electrode is $>10\pi$ mm$^2$.
19. The biosensor of any of paragraphs 1-18, wherein the electrode is either metallic or non-metallic.
20. The biosensor of any of paragraphs 1-19, wherein the metallic electrode is gold, silver, platinum, titanium, or palladium.
21. The biosensor of any of paragraphs 1-20, wherein the non-metallic electrode comprises carbon.
22. The biosensor of any of paragraphs 1-21, wherein the amperometric biosensor is a chronoamperometric biosensor.
23. The biosensor of any of paragraphs 1-14, wherein the polymer further comprising a readout enzyme (ReadE), wherein the ReadE reduces the $Med_{red}$ to $Med_{ox}$ to produce a detectable signal.
24. The biosensor of any of paragraphs 1-10, wherein the readout enzyme (ReadE) is a peroxidase enzyme.
25. The biosensor of any of paragraphs 1-14, wherein the biosensor is a colorimetric biosensor and the detectable signal is colorimetric.
26. The biosensor of any of paragraphs 1-25, wherein the electronically active mediator in the presence of an electron from the enzyme and internal cofactor produce a signal.
27. The biosensor of any of paragraphs 1-26, wherein the electronically active mediator comprises iron(II,III) hexacyanoferrate(II,III) (e.g., Prussian blue).
28. The biosensor of paragraph 24, wherein the readout enzyme (ReadE) converts a readout substrate (ReadS) to a readout product (ReadP) in the presence of hydrogen peroxide, wherein ReadP produces a detectable signal with is an optical signal.
29. The biosensor of paragraph 25, wherein the peroxidase is APEX2 or HRP.
30. The biosensor of any of paragraphs 1-22, wherein the optical signal is colorimetric, fluorescent, and/or bioluminescent.
31. The biosensor of any of paragraphs 24-30, wherein the Readout substrate (ReadS) is selected from any of: Amplex® UltraRed (AUR), PY1, PO1, o-dianisidine Amplex® Red, Hamovanillic Acid (HVA), luminol, OPD, DCFH, ABST, K iodine, or ABST.
32. The biosensor of paragraph 24, wherein the Readout substrate (ReadS) is Amplex® Ultrared (AUR).
33. The biosensor of any of paragraphs 21-28, wherein the Readout Enzyme (ReadE) is APEX2 or a functional variant thereof, and the readout substrate (ReadS) is Amplex® Ultrared (AUR).
34. A system comprising:
   a. an biosensor of any of one of paragraphs 1-33; and
   b. a potentiostat.
35. The system of paragraph 34, wherein the biosensor is an amperometric biosensor which is contained in a Faraday cage.
36. The system of paragraph 35, wherein the potentiostat is linked to at least one electrode of the amperometric biosensor.
37. The system of paragraph 35, wherein the potentiostat is linked to a working electrode and a reference electrode of the amperometric biosensor.
38. The system of paragraph 37, wherein the potentiostat measures the current of the amperometric biosensor.
39. A wearable hormone biosensor device, comprising the biosensor of any of paragraphs 1-24 electrically connected to a potentiostat, wherein the potentiostat is linked to at least the working electrode of the biosensor, and the working electrode is in fluid communication with a wicking paper that wicks sweat or interstitial fluid from the surface of skin of a subject.
40. The wearable hormone biosensor device of paragraph 39, wherein when attached to the skin of a subject, is operable to detect the amount of hormone in sweat or interstitial fluid of the subject, in a real time, quantitative and chronoamperometric manner.
41. A method of using an amperometric biosensor to measure the concentration of hormone comprising:
   a. assembling the biosensor of any one of paragraphs 1-34, wherein the biosensor is a amperometric biosensor;
   b. providing a sample; and
   c. measuring the current produced by the oxidation of any hormone present in the sample.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

Materials and Methods:

Strain Selection: *Pimelobacter simplex* was purchased from ATCC® (Manassas, Va.) and linked with a corresponding GenBank accession number (NZ_CP009896.1). The strain is aerobic and was propagated and grown in ATCC© Medium 18: Trypticase Soy Agar/Broth at 30° C. as recommended by ATCC®.

Strain Growth Curve: In order to determine the doubling time of the strain, growth curves were performed. All growth curves were done in 96 well flat clear bottom black polystyrene TC-treated microplates (Corning Inc.™, Corning, N.Y.). Measurements were taken with an Infinite M200 Pro™ (TECAN Group Ltd., Medford, Mass.) spectrophotometer at 30° C. Readings were performed over 96 cycles of 15 minutes each at 600 nm absorbance with 25 flashes in a 3×3 (XY-Line) type reads per well. In between reads there was orbital shaking at 150 rpm frequency for a total of 10 minutes. To first characterize the growth alone, a 12 serial dilution of 9 concentrations from 0.5-0.0020 $OD_{600}$ nm were prepared in M18 media. Then each concentration was measured as previously described by the TECAN microplate reader and normalized against a media background control in technical triplicate. Afterward, an appropriate starting concentration of cells was chosen which shows a substantially long lag-phase, linear log phase, and a plateau of stationary-phase.

Strain Solvent Growth Curve: Once an appropriate starting cell concentration was chosen, a secondary growth curve was performed to test the toxicity levels of the solvent used to dissolve hormone. *P. simplex* was incubated under microplate reader conditions previously mentioned at a starting OD determined by the first growth curve with $H_2O$ at ½ serial dilutions for a total of eight concentrations (50-0.39%) tested in technical triplicate. Two controls were included per solvent; a positive control without solvent and a media control which allowed for appropriate normalization. Solvent exposure growth curves allowed for choosing the maximum amount of solvent concentration that *P. simplex* would sustain while maintaining relative viability in order to determine a range of hormone concentrations which could be used.

Strain RNA Extraction: Cells were grown in 5 mL M18 at a starting $OD_{600}$ of 0.005 with 21.6 µM hormone in 14 mL polypropylene round-bottom tubes (Corning Inc.™, Corning, N.Y.) in singlet. The cells were incubated at 30° C. with continuous orbital shaking at 150 rpm until the end of lag-phase (3 hours) and mid-log phase (7.5 hours) from the start of inoculation. Controls were grown in the same conditions without hormone. Afterward, samples were removed and a 1:1 ratio of RNAprotect Bacteria Reagent™ (Qiagen Inc.™, Germantown, Md.) was added followed by spinning down at 4° C. for 10 minutes at 4000×g. Supernatant was removed and the pellet re-suspended in 300 µL of RNAprotect™ and transferred into 2.0 mL Safe-Lock Tubes™ (Eppendorf™, Hauppauge, N.Y.). The samples were then spun down at 4° C. for 10 minutes at 10000×g. RNA extraction was done by Qiacube™ (Qiagen Inc.™, Germantown, Md.) set to the RNeasy Protect Bacteria Mini Kit™ protocol of bacterial cell pellet with enzymatic lysis. Lysis buffer was prepared as described by the protocol with the exception of the addition of 150 mg/mL lysozyme (Sigma-Aldrich Corp.™, St. Louis, Mo.) and 20 mg/mL proteinase K (F. Hoffmann-La Roche Ltd™, Indianapolis, Ind.) all diluted in 1×TE buffer. RNA samples were subsequently quantified using Qubit RNA HS Assay Kit™ (Thermo Fisher Scientific Inc.™, Cambridge, Mass.) and analyzed using a RNA 6000 Pico Kit™ (Agilent Technologies Inc.™, Santa Clara, Calif.) in a 2100 Bioanalyzer™ (Agilent Technologies Inc.™, Santa Clara, Calif.). RNA samples were either immediately used for RNA-Seq library preparation or stored long-term at −80° C. after addition of 1 µL RNase Inhibitor, Murine (New England Biolabs™, MA).

RNA-Seq Library Preparation: After RNA samples have been quantified and analyzed they were DNase treated using TURBO™ DNase 2 U/µL (Thermo Fisher Scientific Inc™ Cambridge, Mass.) and cleaned using Agencourt RNA-Clean™ XP SPRI beads (Beckman Coulter, Inc.™, Brea, Calif.). RNA-Seq libraries were then produced from these samples using a modified ScriptSeq v2 RNA-Seq Library Preparation Kit™ (Illumina Inc.™, San Diego, Calif.) ensuring use of unique index primers through ScriptSeq™ Index PCR Primers (Sets 1-4) 48 rxns/set (Illumina Inc.™, San Diego, Calif.). Libraries were quantified by both a Qubit dsDNA HS Assay Kit™ (Thermo Fisher Scientific Inc.™, Cambridge, Mass.) and by Bioanalyzer™ with the High Sensitivity DNA Kit™ (Agilent Technologies Inc.™, Santa Clara, Calif.). The samples were then pooled to 2 nM and submitted to a sequencing core facility. Whole transcriptome RNA sequencing was performed by a NextSeq 500™ (Illumina Inc.™, San Diego, Calif.) at high output (400 M reads) with 75 bp paired end sequencing read length. The data was then analyzed in-house through a proprietary lab computational pipeline.

Enzyme Expression and Purification: KSDH1 was recombinantly expressed and purified with poly-histidine tags in *Escherichia coli*. Synthetic *E. coli* K12 codon optimized fragments of KSDH1 and KSDH2 were ordered through Twist Bioscience and introduced into the pET-52b(+) expression vector through Giboson Assembly cloning techniques. Plasmids were chemically transformed into *E. coli* BL21 (DE3) (New England Biolabs™, MA) with induction of lysogeny broth cultures at $OD_{600}$ 0.6 to 0.8 using 1 mL of 1M isopropyl b-D-1-thiogalactopyranoside (IPTG) before analysis by SDS-polysaccharide gel electrophoresis (SDS-PAGE). Confirmed expression prompted 1 L cultures for expression and protein purification through disruption of cells using lysozyme and by passing cell lysate over a HisPur™ Ni-NTA Resin-packed column (Fisher Scientific™, Pittsburgh, Pa.). Final protein products were quantified using the Pierce Micro BCA Protein Assay™ kit (Fisher Scientific™, Pittsburgh, Pa.).

In Vitro Enzyme Characterization: Amplex® UltraRed assays were performed per instruction of the manufacturer (Thermo Fisher Scientific, Cambridge, Mass.). Final concentrations of Amplex® UltraRed, 500 uM, and HRP, 1 U/mL, in a total volume of 20 µL were used. Hormone and KSDH1 and KSDH2 concentrations varied with experiment. All measurements of fluorescence were done in a 384 well flat bottom black polystyrene microplate (Corning Inc.™, Corning, N.Y.) and read in an Infinite M200 Pro™ (TECAN Group Ltd.™, Medford, Mass.) spectrophotometer at room temperature with the excitation set to 490 nm and emission at 585 nm. Readings were done over 1 hour with each well read every 30 seconds.

Sensor Preparation: Electrochemical experiments were performed with a DropSens µSTAT4000P (Metrohm USA™, Riverview, Fla.). Sensors were prepared with Screen-Printed Prussian Blue/Carbon Electrode (Metrohm USA™, Riverview, Fla.) or platinum Interdigitated Electrodes (Metrohm USA™, Riverview, Fla.). KSDH1 (400 or 1200 µM) was deposited onto SPEs or IDEs by drop-casting 10 µL of it onto the working electrode. The sensors were allowed to dry overnight at room temperature.

Sensor Characterization: In order to quantify the current response of the hormone biosensor, chronoamperometric experiments were performed where various hormones in PBS (0-1000 µM) were deposited onto SPEs or IDEs with 4 or 12 nmol KSDH1 or KSDH2.

Chronoamperometric responses with carbon or carbon/PB SPEs were recorded over time, with a potential −0.2 V (versus Ag/AgCl). If a liquid mediator was used, such as mPMS, RU, RF, or PB, were used then the appropriate potentials of +0.2 V, +0.2 V, +0.4 V, +0.6 V were applied. If platinum IDEs were used then a potential of +0.6 V was applied. At the beginning of the experiment, 40 µL 1×DPBS was added to the biosensor, followed by an addition of 10 µL hormone solution at various concentrations and boluses at predefined time points.

Biosensor Preparation

All electrochemical experiments were performed by using a DropSens µSTAT4000P (Metrohm USA™, Riverview, Fla.). SPEs such as DS710, DS110, DSF10 or IDEs were purchased (Metrohm USA™, Riverview, Fla.). KSDH1 (400 or 1200 µM) was then deposited onto the SPEs or IDEs by drop-casting 10 µL of it onto the working electrode. The sensors were allowed to dry overnight at room temperature.

In Vitro Biosensor Characterization

The electrochemical performance of the hormone biosensor was evaluated in vitro using 1× Dulbecco's Phosphate Buffered Saline (1×DPBS) (Life Technologies™, Grand Island, N.Y.). Chronoamperometric responses were recorded at −0.2 V, +0.2 V, +0.4 V, or +0.6 V vs. a Ag/AgCl reference electrode depending on the mediator and electrode metal used.

Example 1

Enzyme-Based Electrochemical Hormone Biosensor

Physiologically relevant wearable sensors are in increasingly high demand, yet existing sensors are severely limited in the number and type of analyte they can detect. The lack of molecular sensing parts specifically is prohibiting the development of the next generation of biosensors. To overcome this challenge, RNA-Seq was used to identify enzymatic sensor parts from microbes for a virtually unlimited number of analytes. Described herein is the first electrochemical redox enzyme-based biosensor for hormone.

Alternative terms for the hormone biosensor described herein include but are not limited to the following: enzyme-based electrochemical hormone biosensor monoamine oxidase biosensor for detection of hormone; monoamine oxidase biosensors for electrochemical detection of hormone; enzyme-based hormone sensor, derived from microbial screening; electrochemical-enzymatic detection of hormone; electrochemical hormone sensing with an enzyme derived from microbial screening towards tobacco smoking monitoring.

Figure 3:
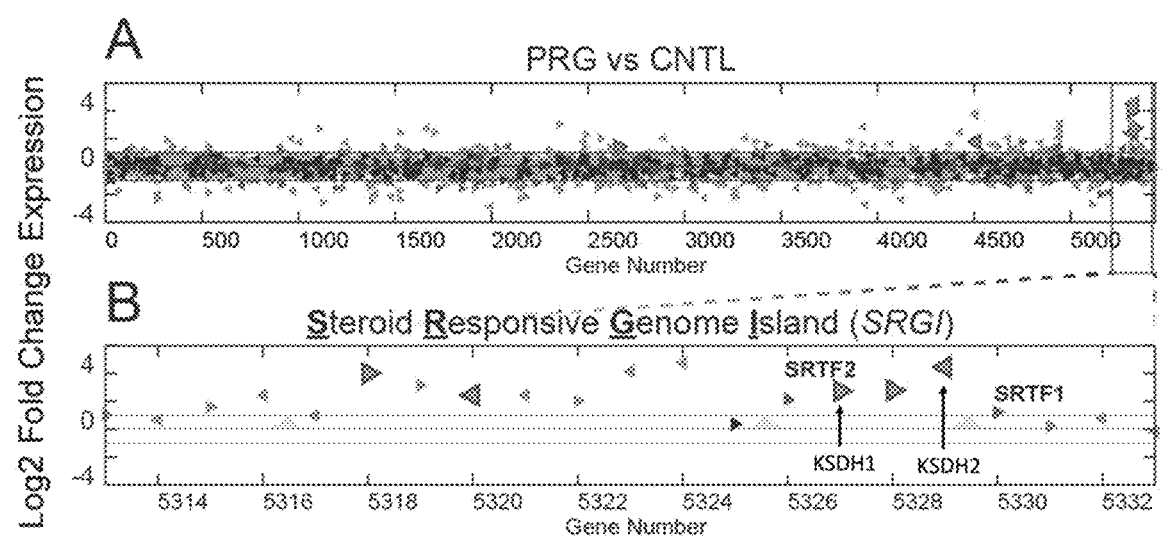
FIG. 3 is a series of graphs showing that RNA-Seq identified the steroid degrading genome cluster in *Pimelobacter simplex*. In the SRGI cluster, sterol responsive enzymes 3-ketosteroid-1-dehydrogenase 1 (KSDH1) and 3-ketosteroid-1-dehydrogenase 2 (KSDH2) are highly expressed in the presence of progesterone.
Figure 4A:
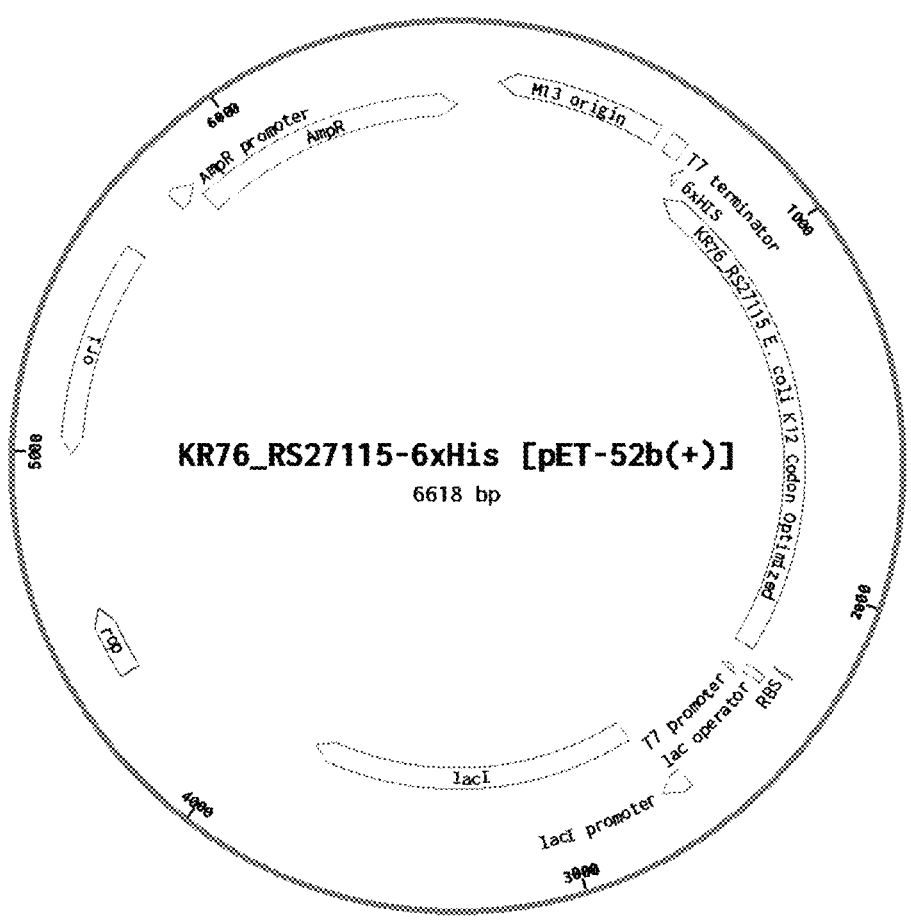
FIGS. 4A-4C illustrate two putative sterol responsive enzymes KR76 RS27115 (KSDH1) (FIG. 4A), and KR76 RS27125 (KSDH2) (FIG. 4B) from *P. simplex* cloned into expression vectors with purification tag 6×HIS. RT-qPCR results show the two sterol responsive enzymes have strong RNA expression levels for induced KR76 RS27115-6×His and KR76 RS27125-6×His under tight lacI control as compared to uninduced, with KR76 RS27115-6×His having significantly higher expression (FIG. 4C).
Figure 4B:
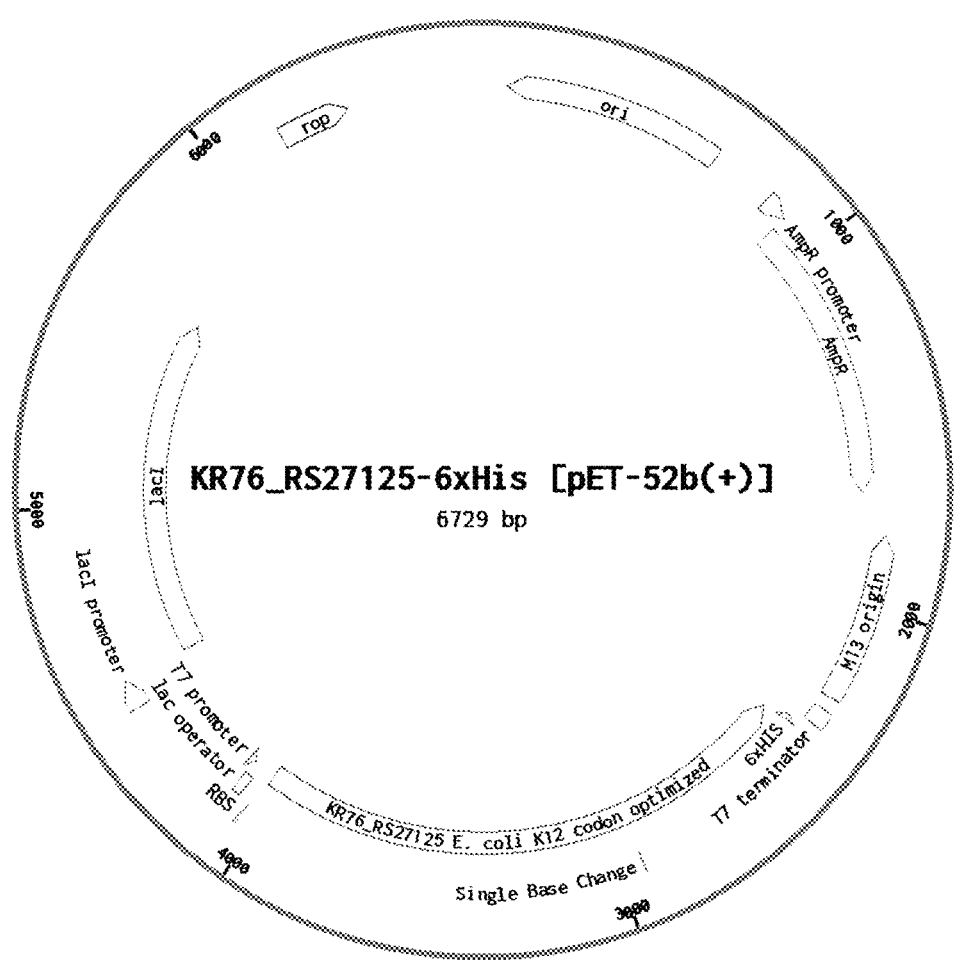
Figure 4C:
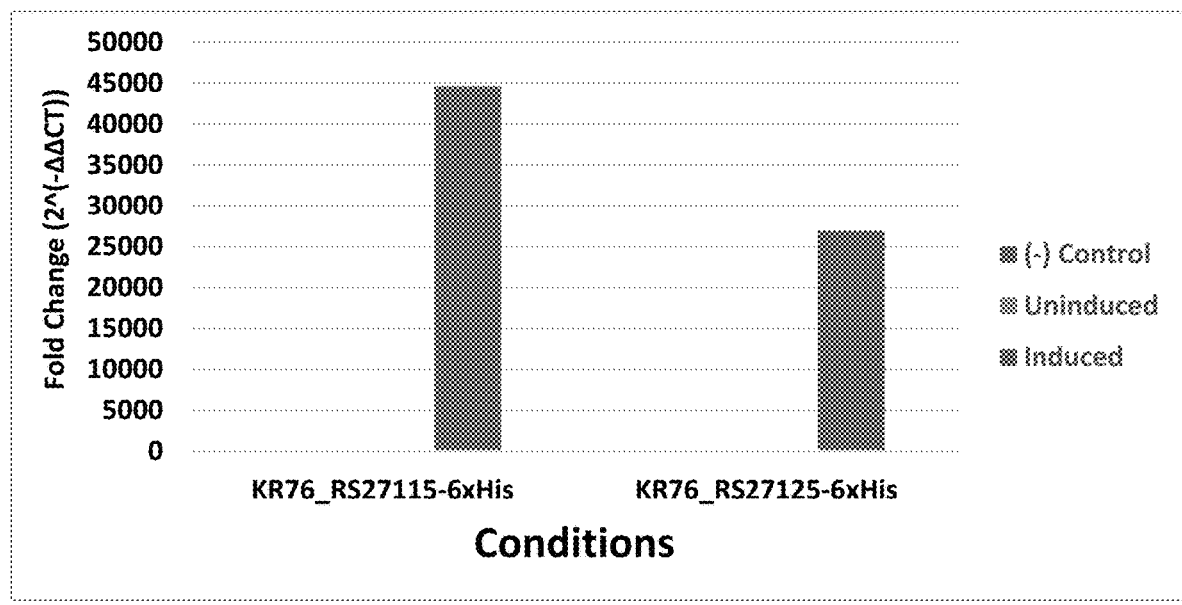

The optimal RNA-Seq experimental conditions were selected by varying the bacterial inoculation, solvent, and hormone concentrations used in the serial dilution growth assays so as to provide a distinct change in the transcriptome expression levels without drastically affecting bacterial physiological growth. Subsequent computational analyses revealed the key steroid responsive genomic island, SRTF2, and that the most highly differentially expressed enzyme encoding genes were 3-ketosteroid-Δ1-dehydrogenase (KSDH) KSDH1 and KSDH2, for the target sterol (see e.g., FIG. 3). The KSDH1 and KSDH2 genes were codon optimized, synthesized, and cloned into expression vectors with a histidine tag and expressed (~10 mg/mL). The protein was purified via FPLC and SEC.

Figure 9A:
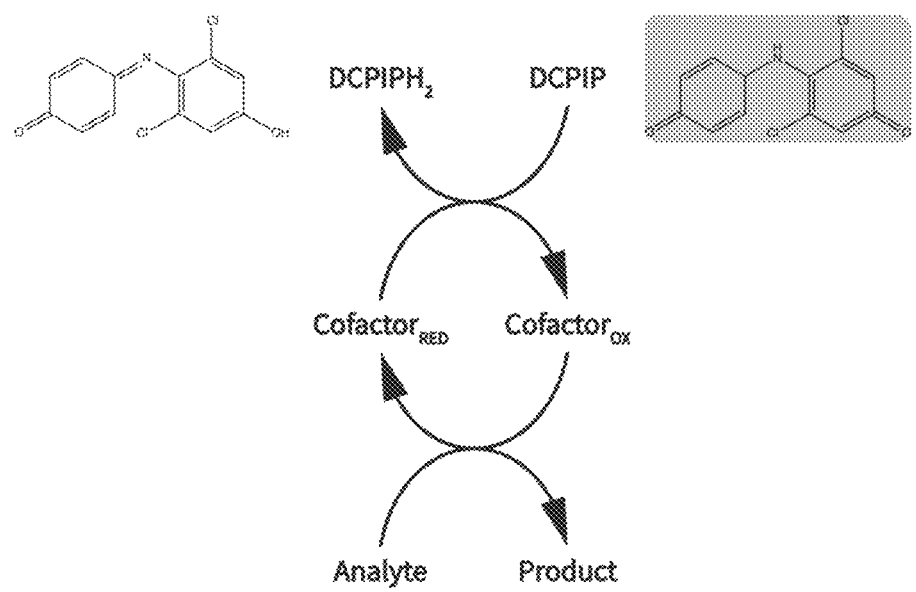
FIGS. 9A-9D demonstrate KSDH1 is a dehydrogenase enzyme, with a high affinity for progesterone and cortisol. A 2,6-Dichlorophenolindophenol functional assay was used to test whether KSDH1 is a dehydrogenase (FIG. 9A). A sterol screen showed KSDH1 has high sensitivity for hydrocortisone and progesterone (FIG. 9B). Binding affinity is strong for hydrocortisone (FIG. 9C), and progesterone (FIG. 9D) as shown per the kinetics derived from a velocity by hormone concentration experiment; turnover number=kcat=Vmax/[ET], [ET]=total enzyme concentration.
Figure 9B:
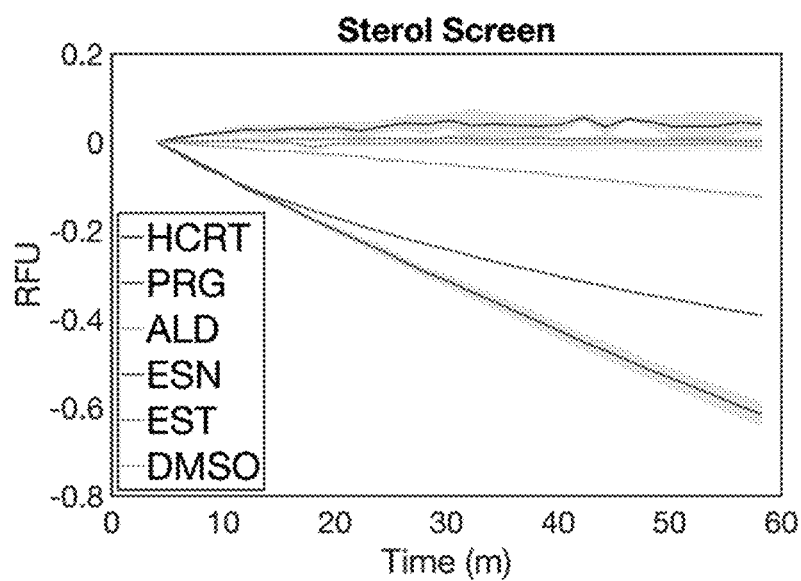
Figure 9C:
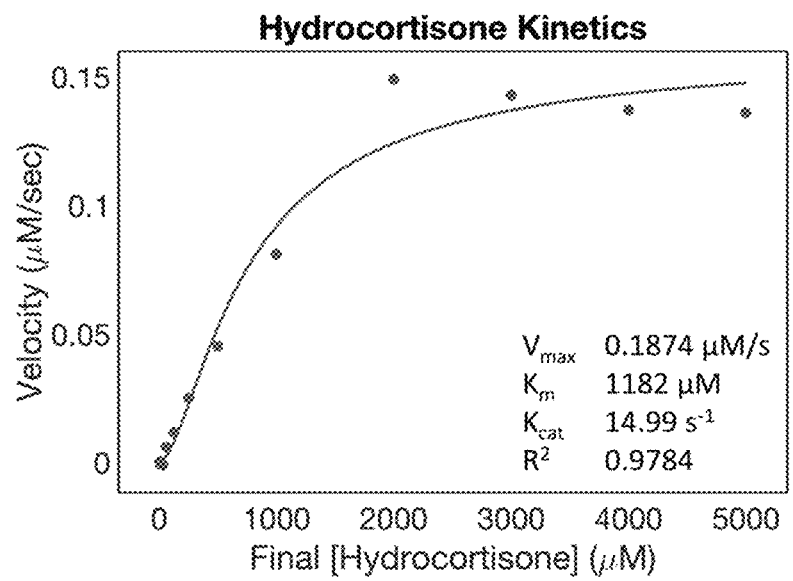
Figure 9D:
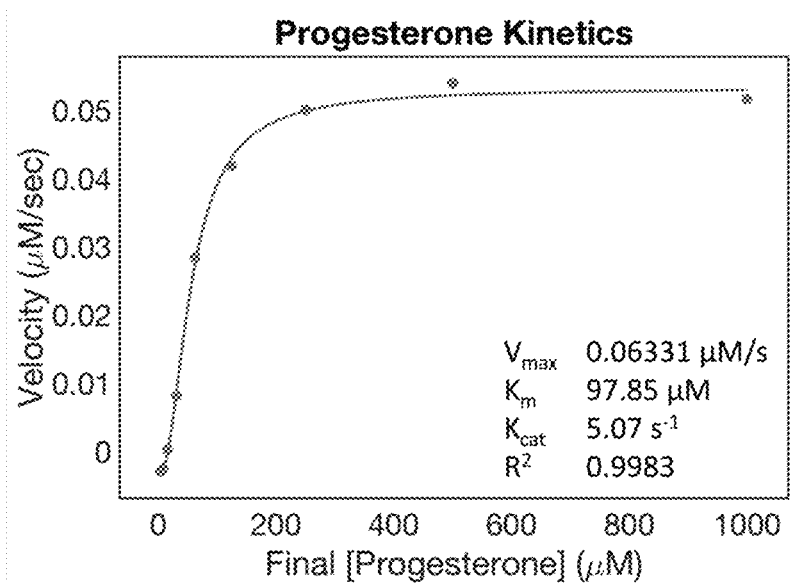
Figures 9E, 10:
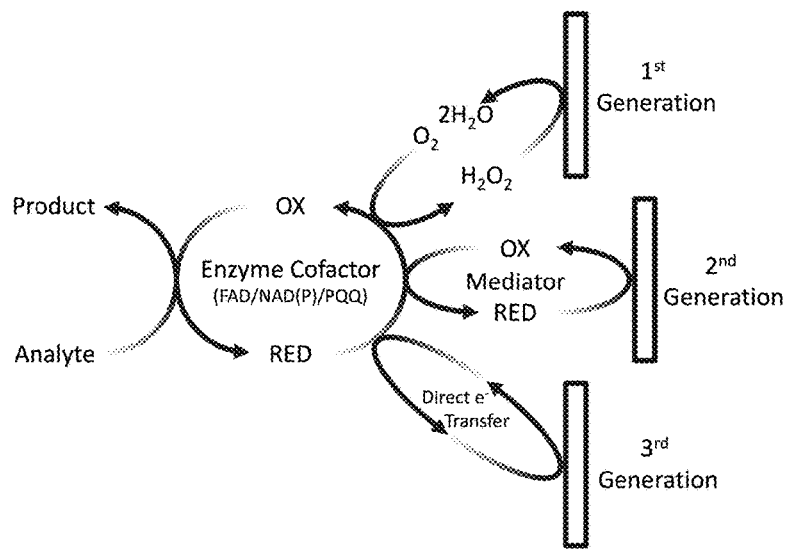
FIG. 9E is a table of the kinetic parameters ($K_M$, $K_{cat}$, $K_{cat}/K_M$ and $1/k_{cat}$) of KSDH1 versus known oxidases such as glucose oxidase, lactose oxidase, and nicotine oxidase used as biorecognition elements in biosensors. The $K_M$ is (substrate concentration at which 12 maximum enzymatic reaction rate is achieved by): (i) substrate's binding affinity, and (ii) rate of enzyme-substrate complex turned into product ($k_{cat}$).
FIG. 10 is a high level electron flow diagram for engineering electrochemical biosensors (modified from Ferri et al.).
Figure 11A:
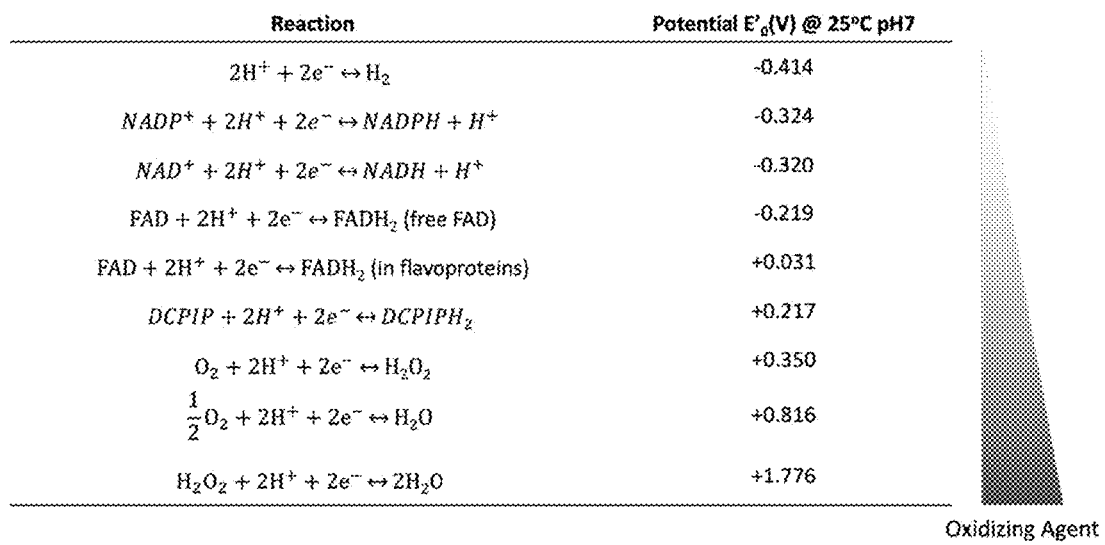
FIGS. 11A-11C illustrate relevant electrochemical redox potentials; strong reducing agents have high electron-transfer potential (give electrons); strong oxidizing agents have low electron-transfer potential (take electrons) (FIG. 11A), and common primary electron acceptors for enzymes, FAD, PQQ, and NAD(P)*.
Figure 11B:
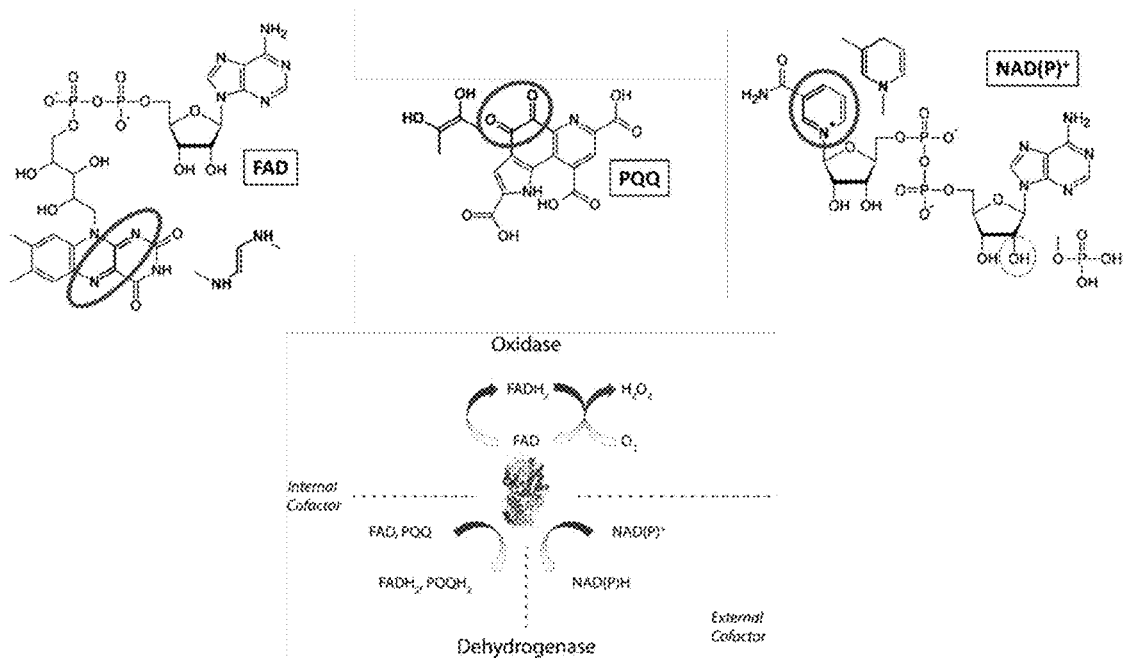
Figures 11C, 12:
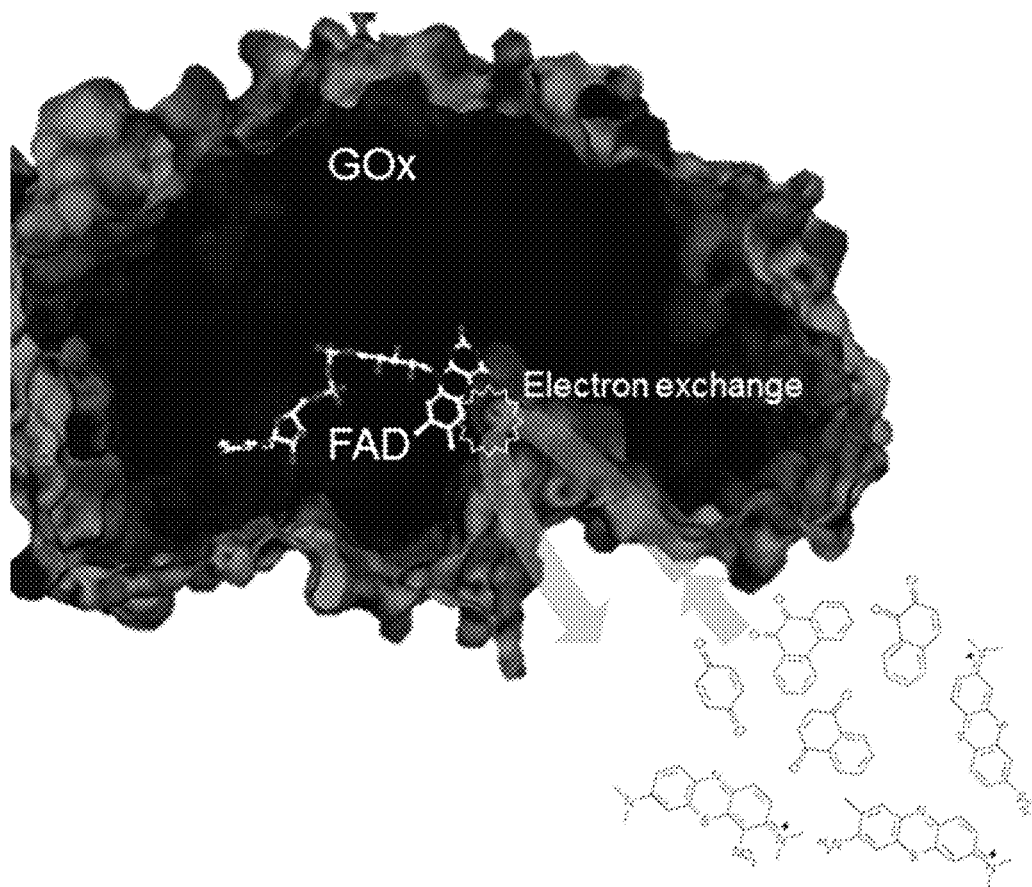
FIG. 12 illustrates that a soluble mediator can strip electrons from an internal enzyme cofactor depending on the location and openness of the catalytic core (Figure from Ferri et al.).
Figures 13A, 13B:
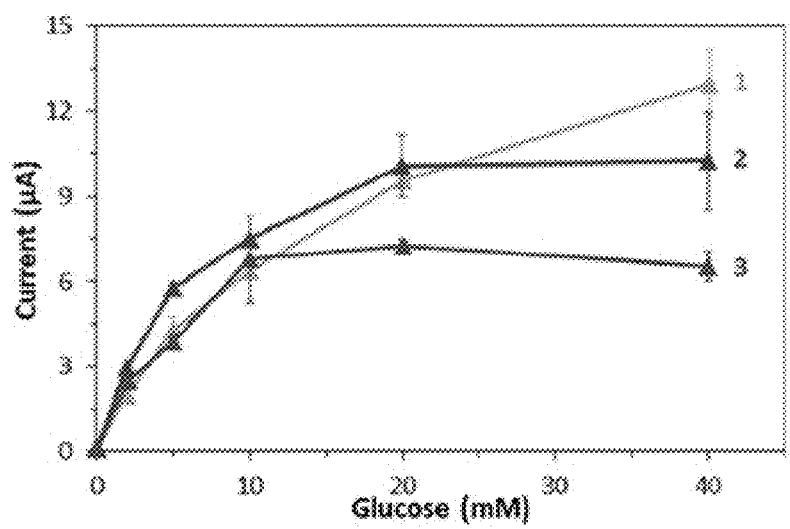
FIGS. 13A-C. Various soluble mediators may be used to engineer dehydrogenase biosensors (FIG. 13A, table from Loew et al.). Enzyme structure dictates mediator performance as seen by chronoamperometric responses in the presence of glucose with FADGDHγαβ(QY) (bacterial FADGDH) enzyme (FIG. 13B), and AfGDH (fungal FADGDH) enzyme (FIG. 13C). Recorded current output 5 seconds after application of potential in presence of glucose. Mediators: (1) 100 nM PMS, (2) 100 mM ferricyanide, and (3) 100 nM hexaammineruthenuim(III). Figures from Loew et al.
Figure 13C:
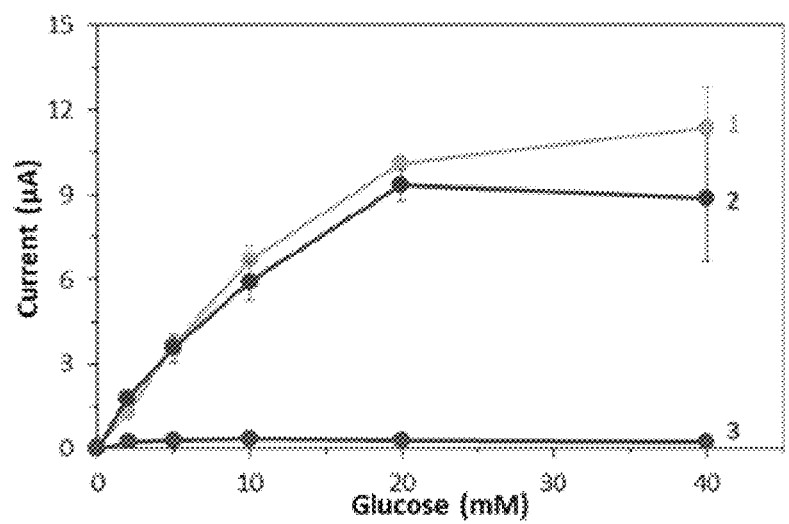
Figure 16A:
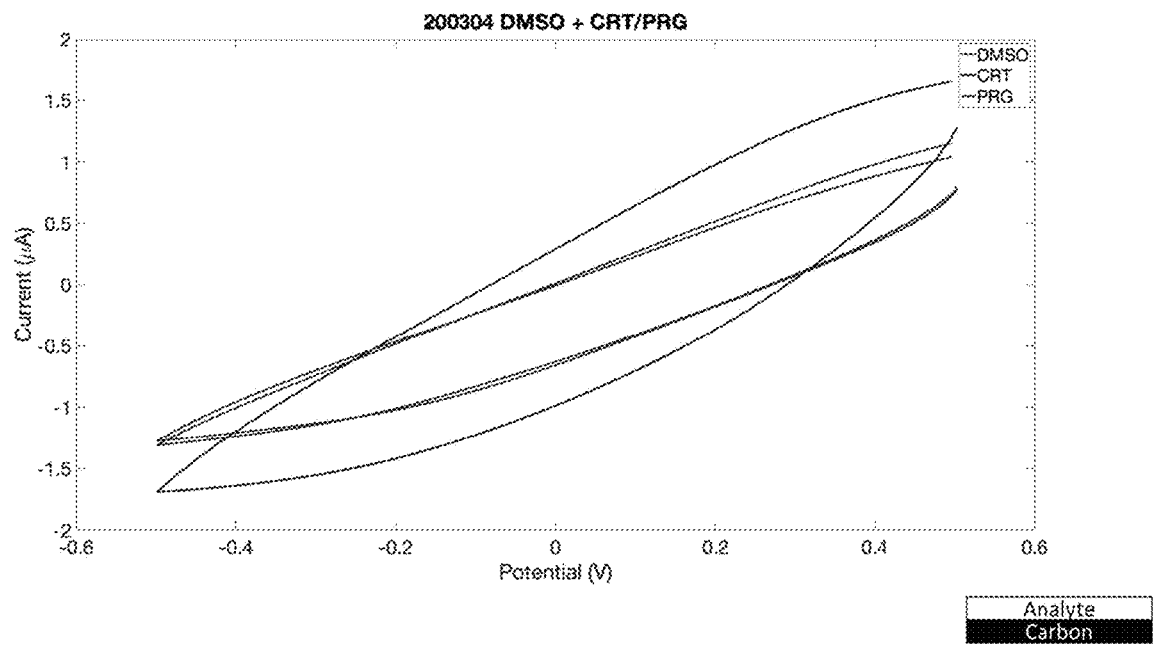
FIGS. 16A-J are cyclic voltammetry results representing electroactivity for various conditions: DMSO/CRT/PRG are not electroactive with a DS110 (FIG. 16A); EtOH/CRT/PRG are not electroactive with a DS110 (FIG. 16B); there is no clear redox of the internal FAD cofactor without mediator with a DS110 (FIG. 16C); there is no redox of the internal FAD cofactor in the presence of CRT with fixed PF using a DSF10 (FIG. 16D), or in the presence of PRG with fixed PF using a DSF10 (FIG. 16E); redox of the internal FAD cofactor is unclear in presence of CRT with fixed PB using a DS710 (FIG. 16F), or in presence of PRG with fixed PB using a DS710 (FIG. 16G), or in the presence of CRT with mPMS in solution using a DS110 (FIG. 16H), or in presence of CRT with RU in solution using a DS110 (FIG. 16I), or in presence of CRT with PF in solution using a DS110 (FIG. 16J).
Figure 16B:
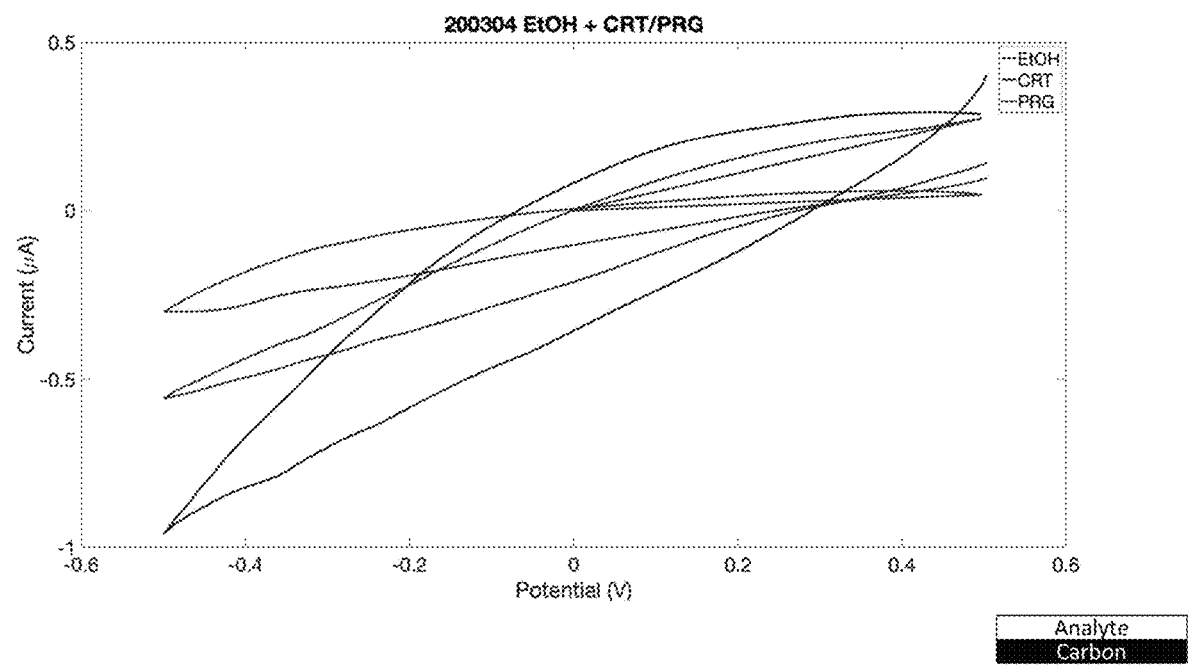
Figure 16C:
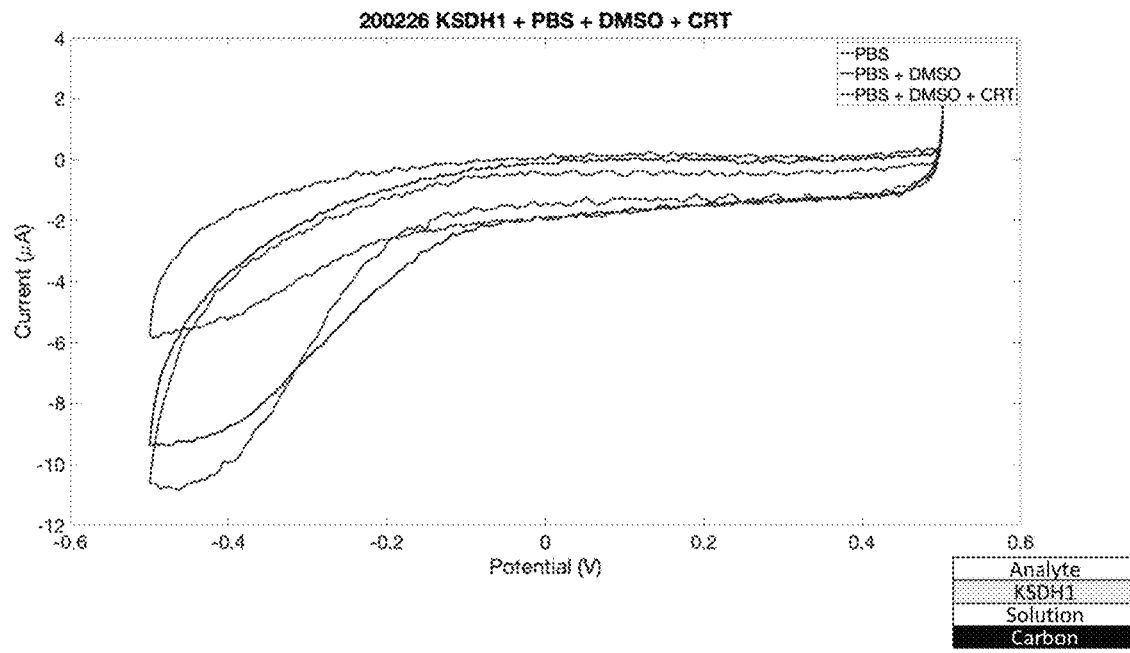
Figure 16D:
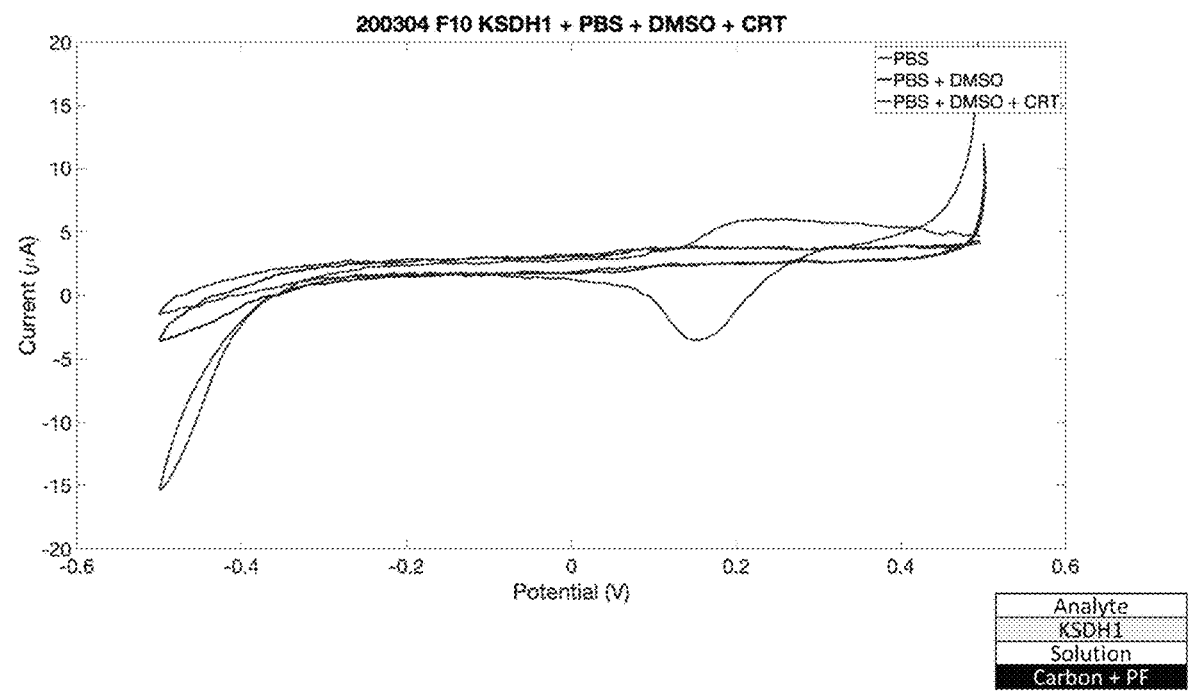
Figure 16E:
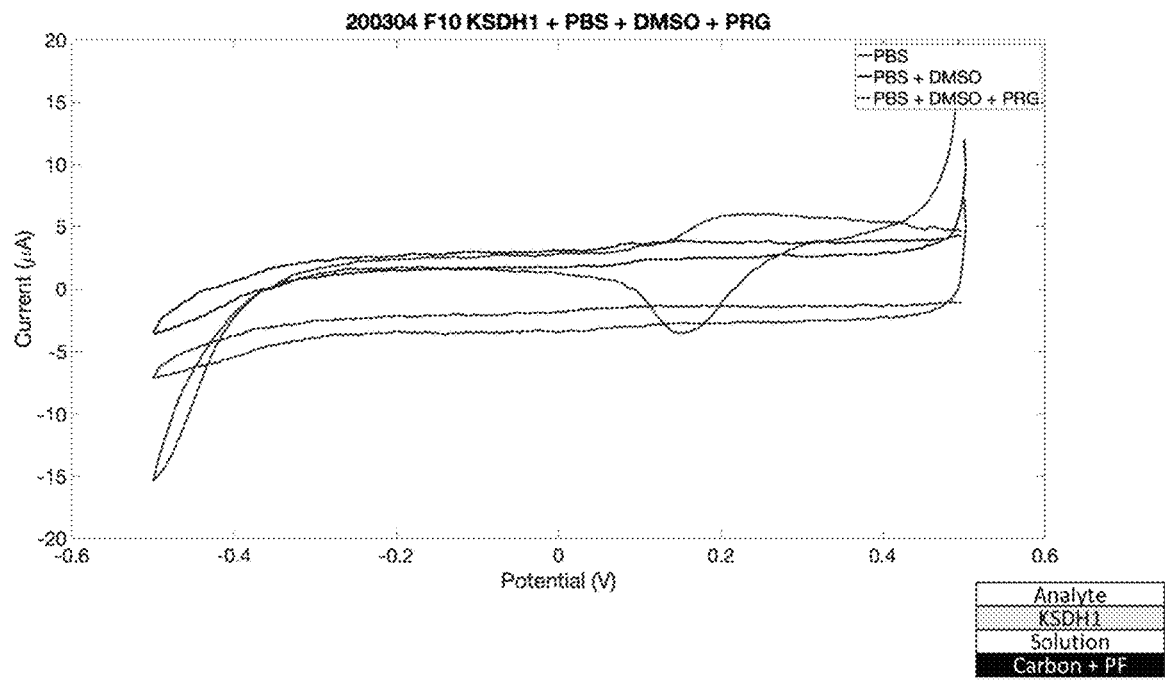
Figure 16F:
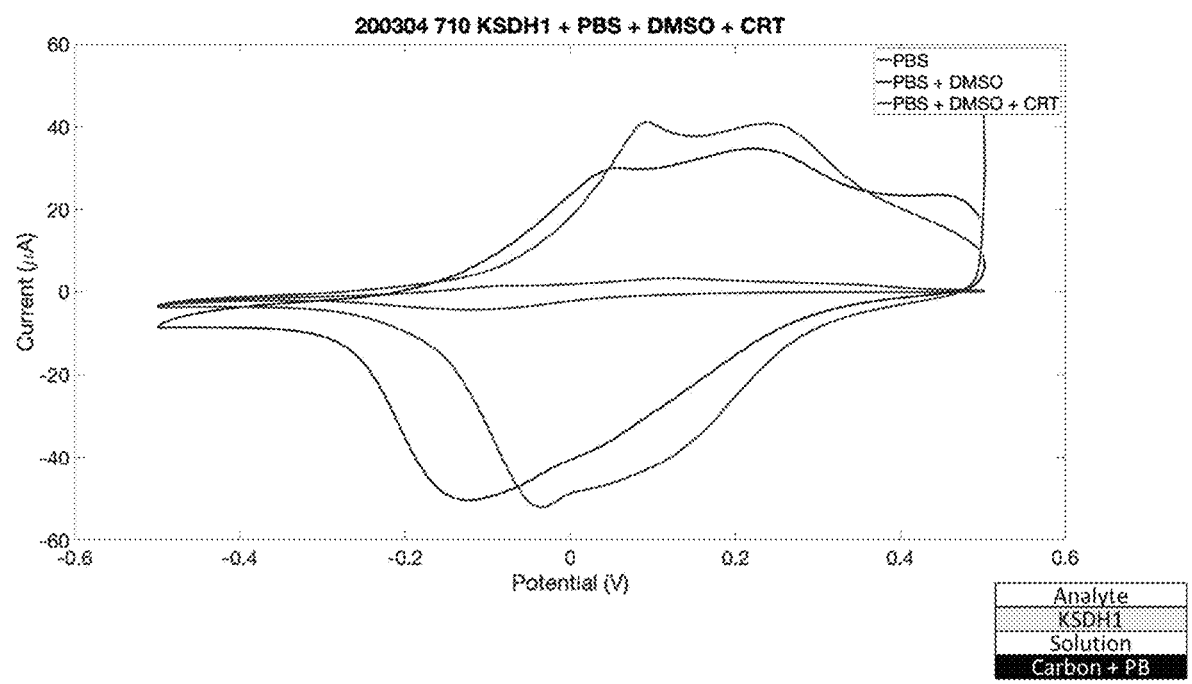
Figure 16G:
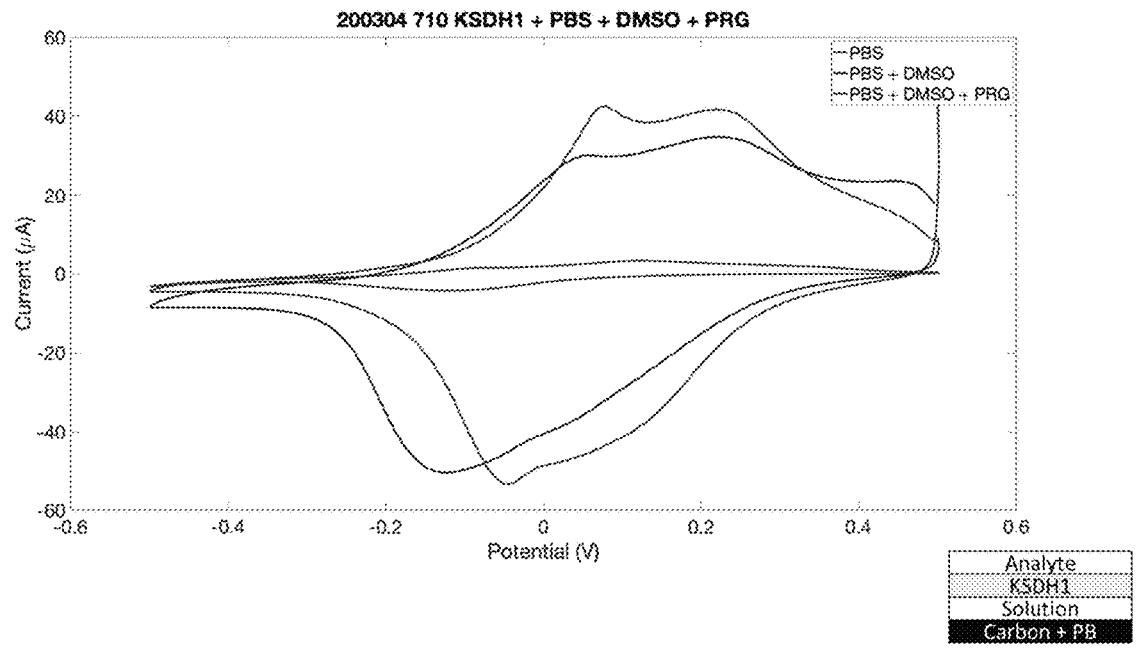
Figure 16H:
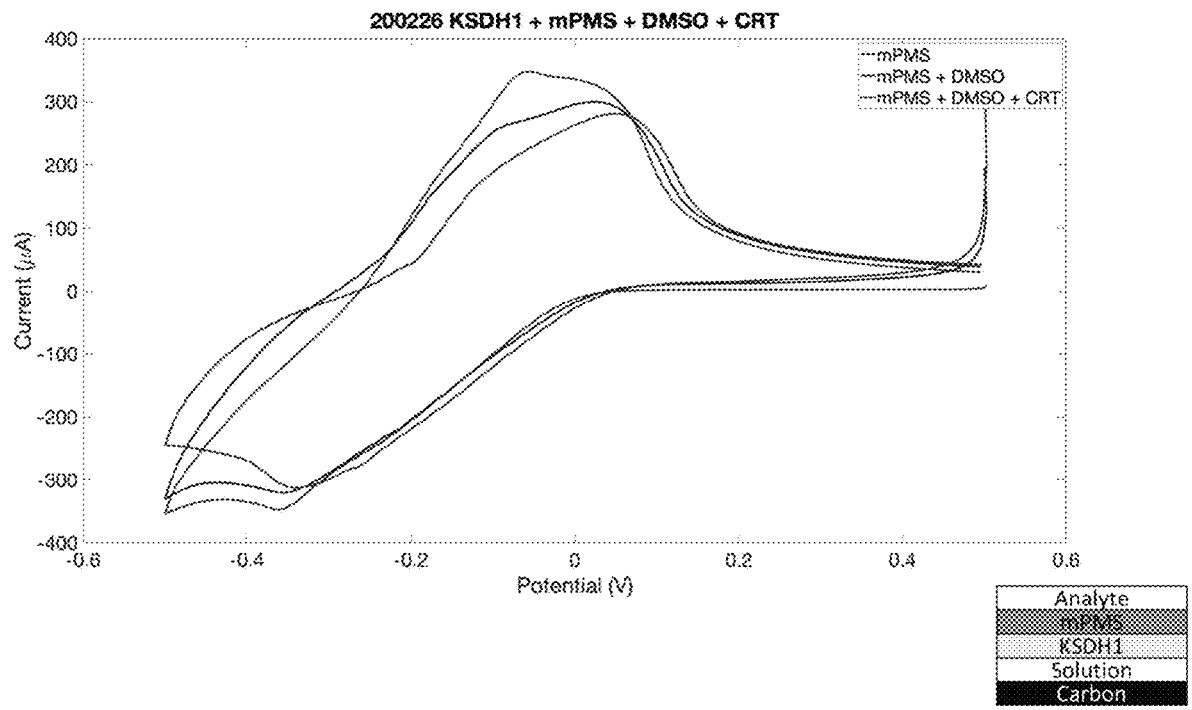
Figure 16I:
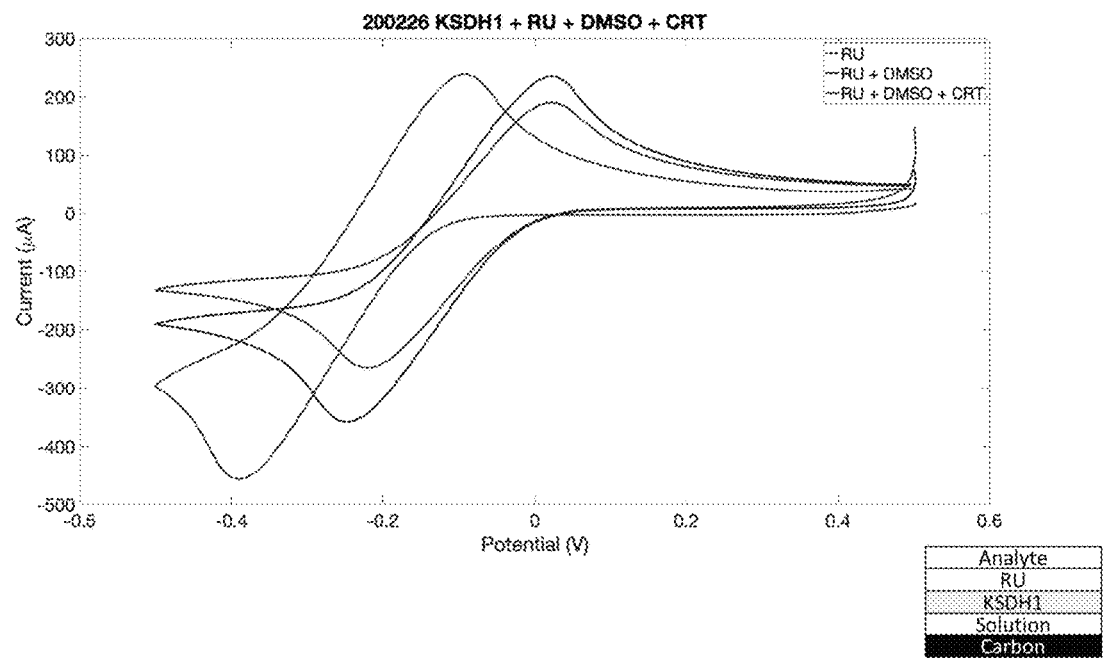
Figure 16J:
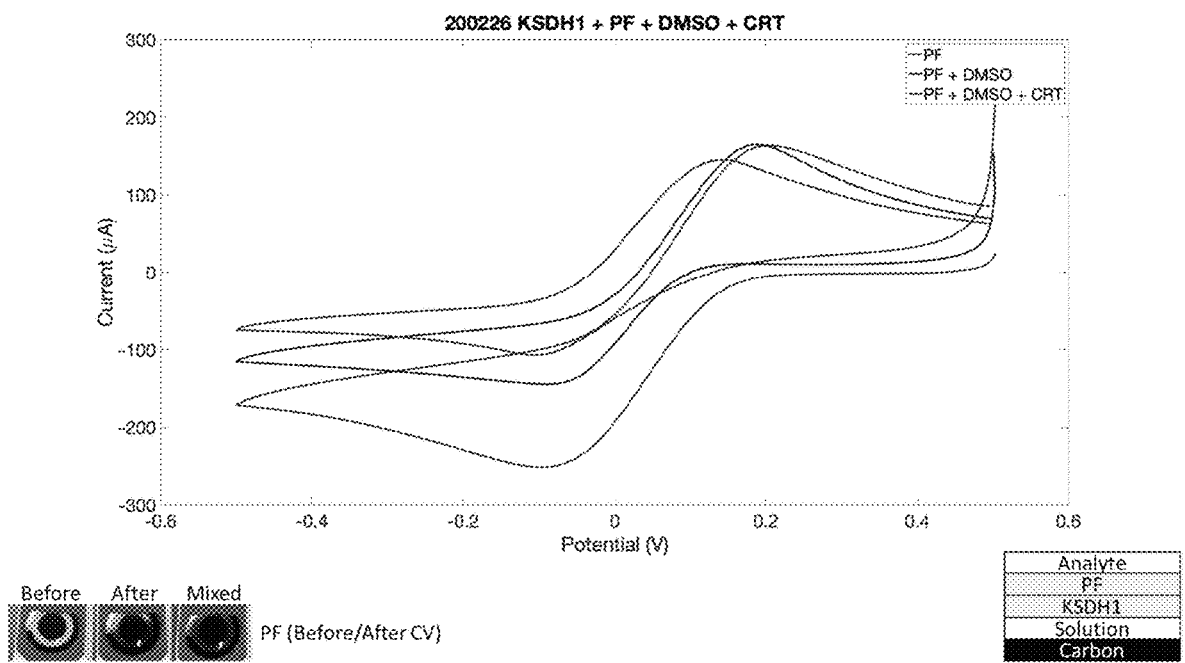
Figure 17A:
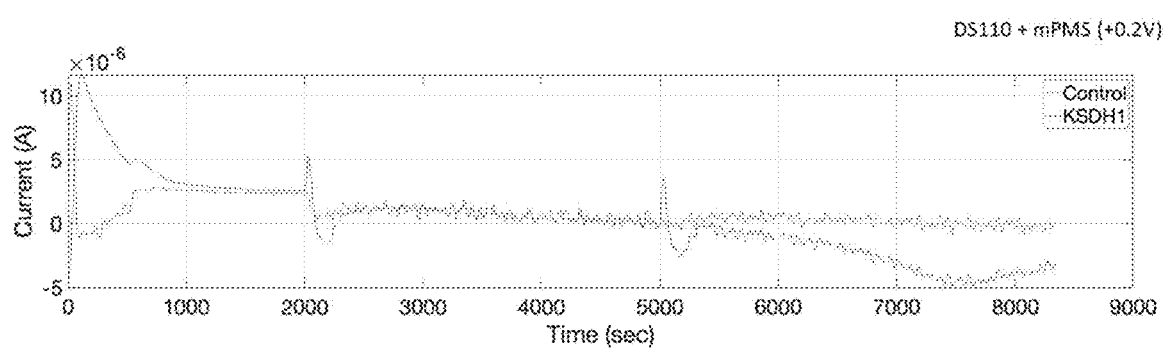
FIGS. 17A-B. DS110 had no chronoamperometric signal with soluble mediators mPMS (FIG. 17A) and RU (FIG. 17B), at +0.2 V. Filtered data with normalized $F_{cutoff}$=0.01 Hz.
Figure 17B:
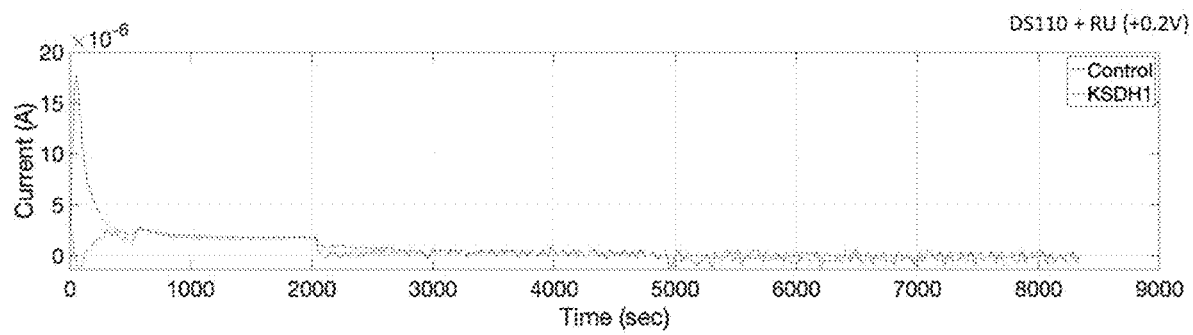
Figure 18A:
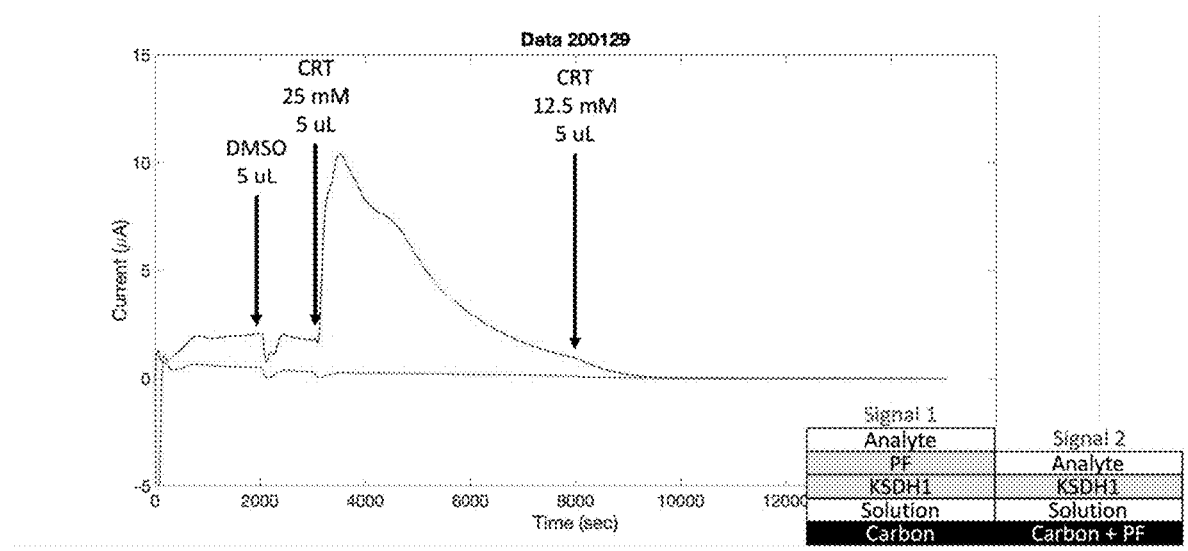
FIGS. 18A-B. Chronoamperometric response to cortisol with soluble PF (signal 1) or without PF (signal 2) with KSDH1 in solution (1 nmol enzyme) using a DS110 (FIG. 18A). KSDH1 charge generated is close to expected. 1 coulomb (C)=6.24 E+18 e⁻. Calculated cortisol added 1.23 E-07 mol; or 7.53 E+16 molecules; 1 coulomb (C)=6.24 E+18 (e⁻); expected charge 2.41 E-02 C; actual charge 2.20 E-02 C (FIG. 18B).
Figure 18B:
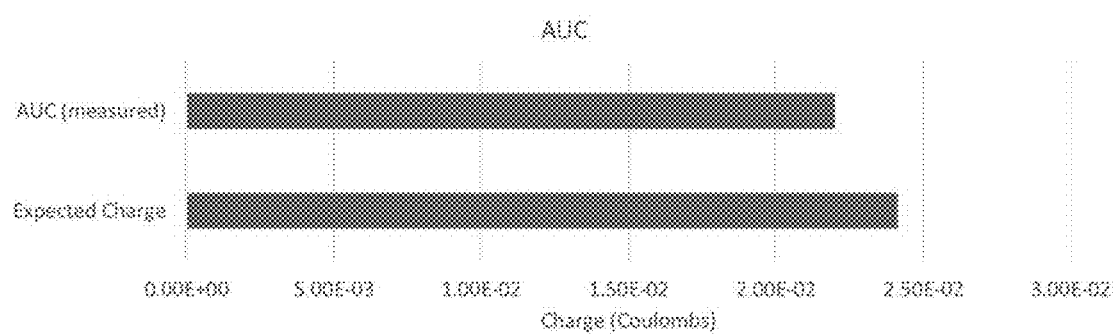
Figure 19A:
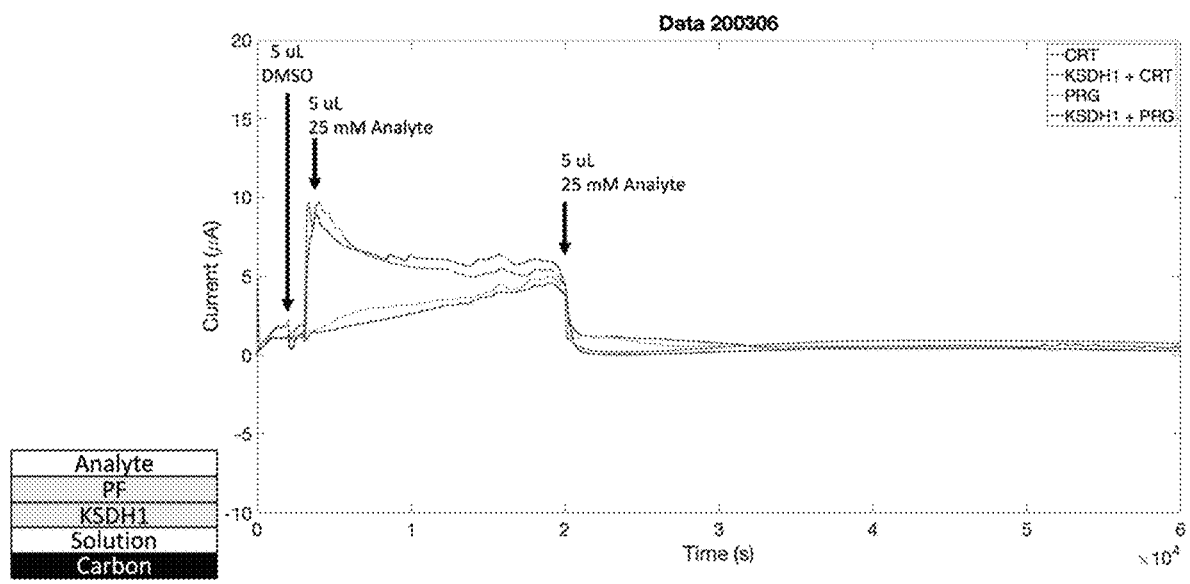
FIGS. 19A-B. Cortisol (CRT) and progesterone (PRG) have a similar signal with KSDH1. 25 mM cortisol or progesterone in 5 µl of 1 nmol KSDH1 using soluble PF as a mediator and a DS110 SPE (FIG. 19A). Area under the curve (AUC) is double expected charge (FIG. 19B).
Figure 19B:
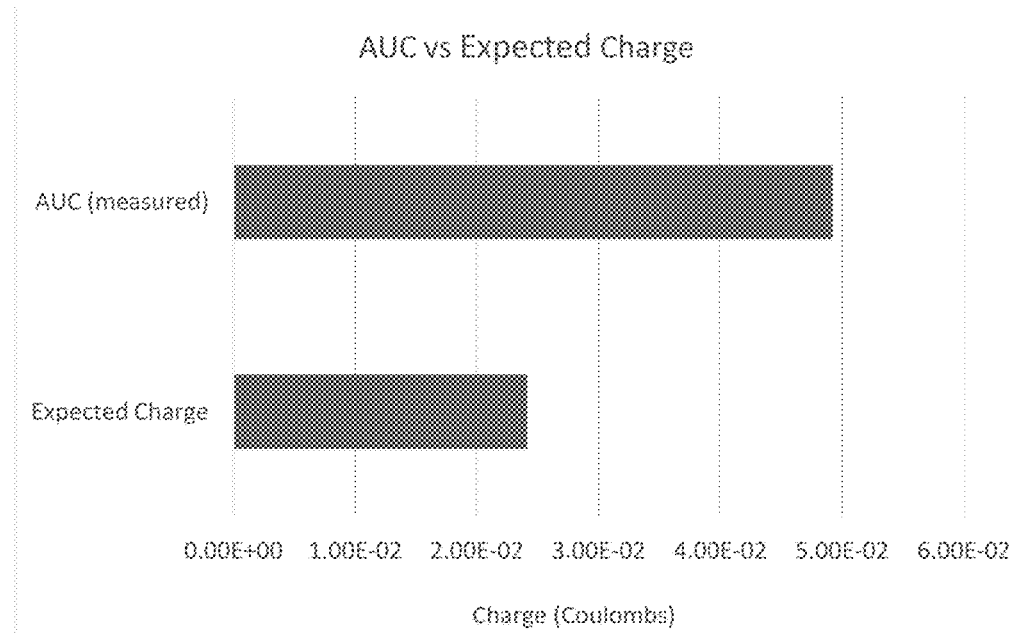
Figure 20A:
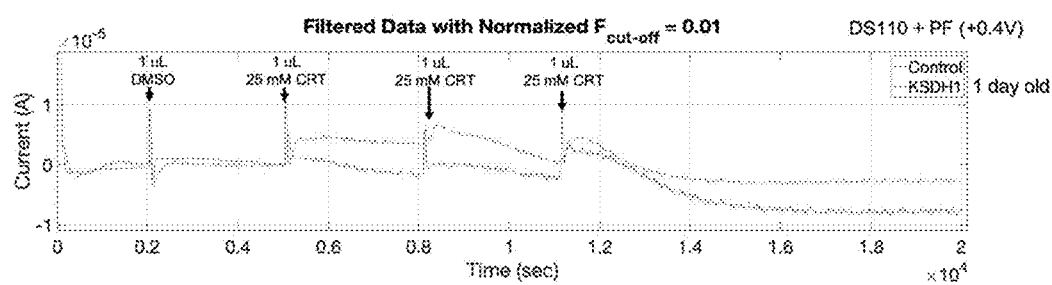
FIGS. 20A-B. Cortisol and progesterone with KSDH1 have signal loss after repeat additions after storage of KSDH1 in 4 C for one day (FIG. 20A), and after two days (FIG. 20B), 25 mM cortisol or progesterone in 5 µl of 1 nmol KSDH1. Control is DMSO; DS110 plus PF (0.4V).
Figure 20B:
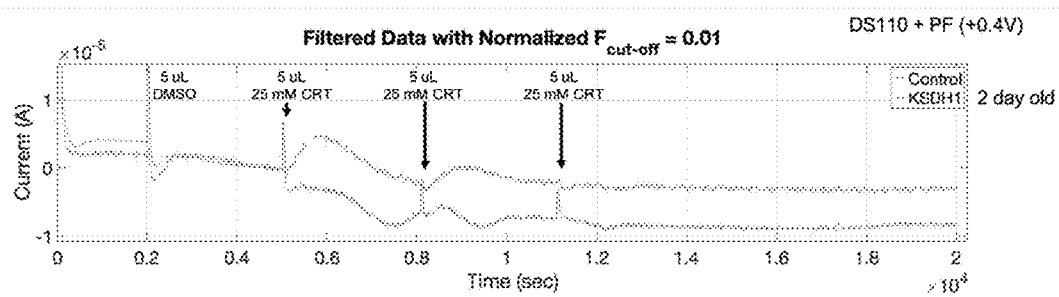
Figure 21A:
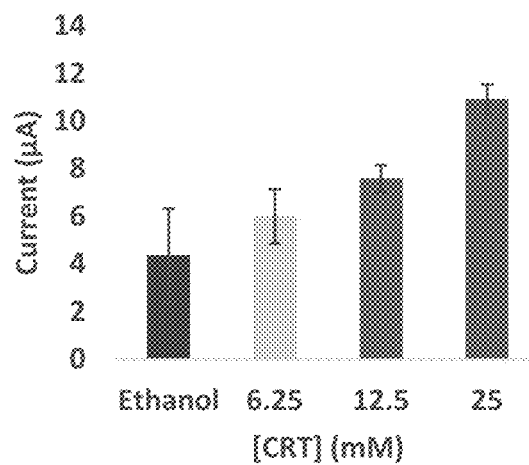
FIGS. 21A-B. Dose response of cortisol dissolved in ethanol followed by applied potential, chart (FIG. 21A), and graph (FIG. 21B); 1 nmol KSDH1, analyte added at t=0 s., +0.4V potential, filtered with a low-pass filter with a cutoff at 0.01 Hz using a DS110 and soluble PF.
Figure 21B:
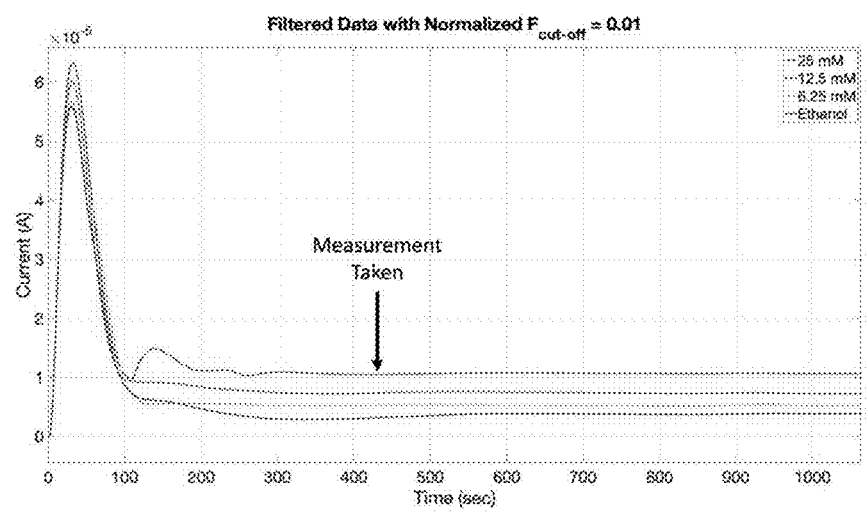
Figure 22:
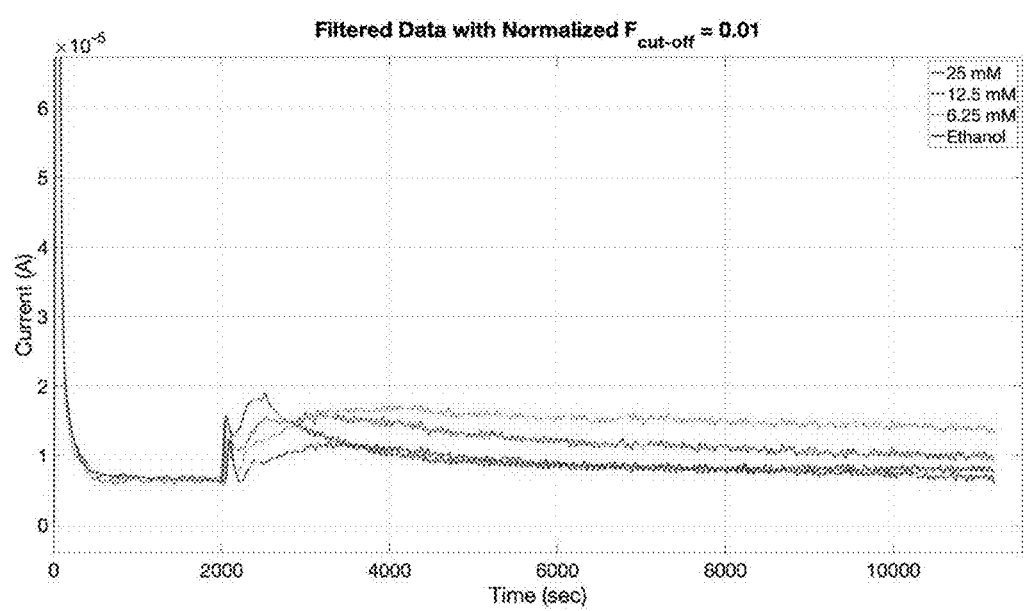
FIG. 22. Dose response of cortisol dissolved in ethanol followed by applied potential; 1 nmol KSDH1, analyte added at t=2000 s., +0.4V potential, filtered with a low-pass filter with a cutoff at 0.01 Hz using a DS110 and soluble PF. The signal drops soon after analyte addition showing this is not a viable electrochemical setup of measuring hormones in solution with this configuration.
Figure 23A:
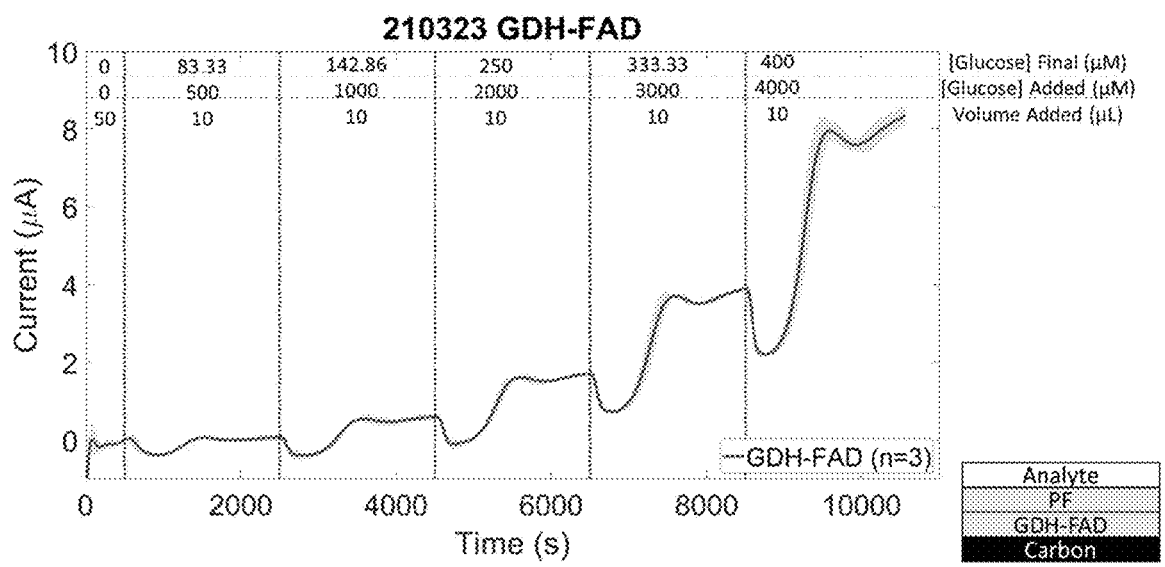
FIGS. 23A-C. Glucose dose response using a glucose dehydrogenase (GDH-FAD) electrochemical biosensor (FIG. 23A). Soluble mediator PF was used with a DS110 SPE and a potential of +0.2V. KSDH1 uses the same internal cofactor (FAD). Electrochemical biosensor produced with KSDH1 is illustrated by a current response to progesterone using the same configuration (FIG. 23B). Dose response for progesterone in response to KSDH1 under the same configuration (FIG. 23C). KsdD4 denotes the same enzyme as KSDH1.
Figure 23B:
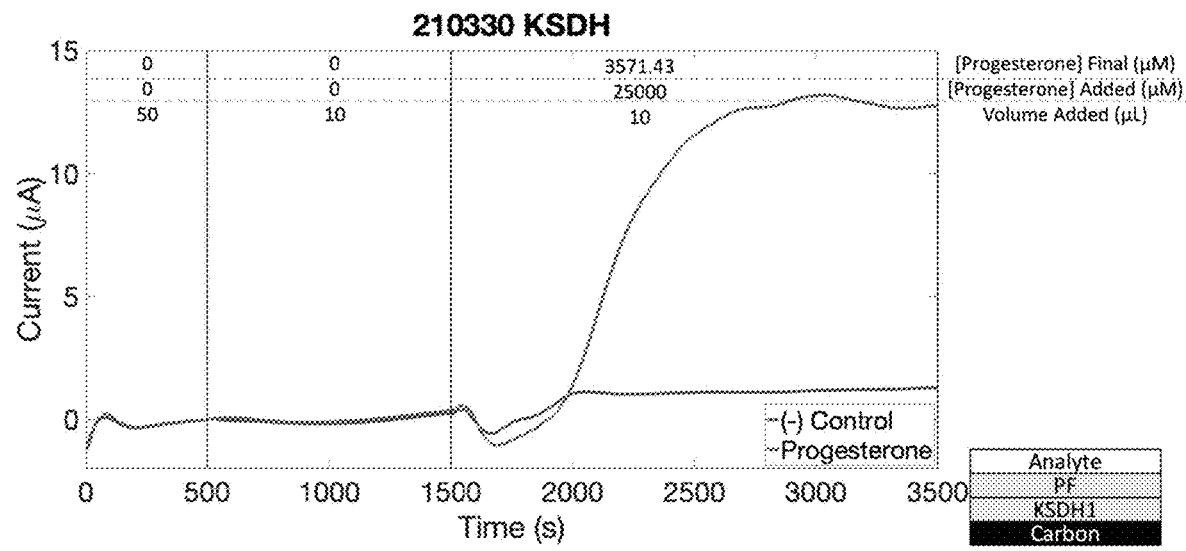
Figure 23C:
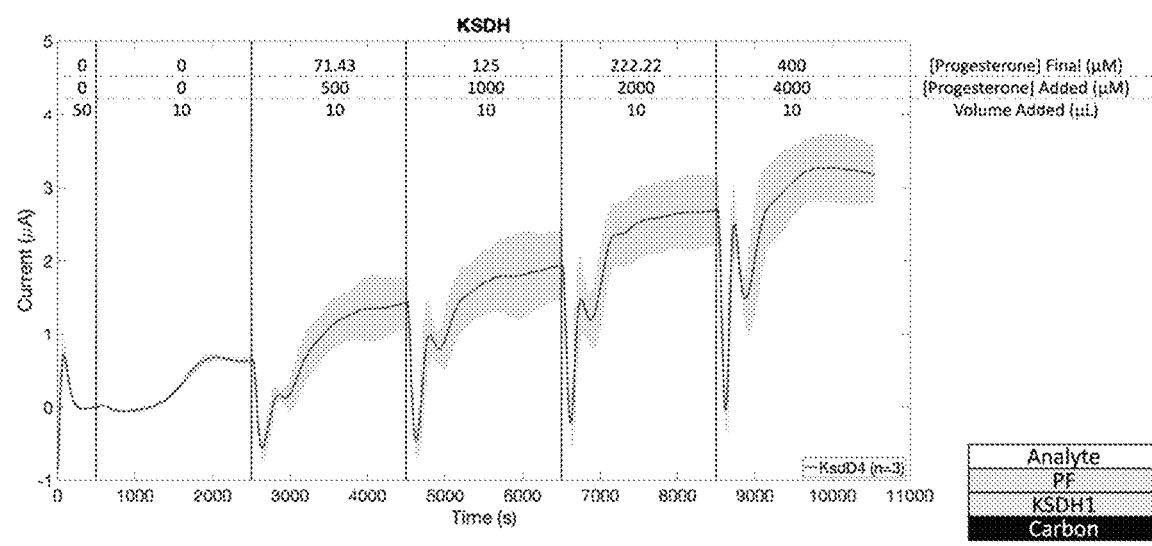
Figure 24A:
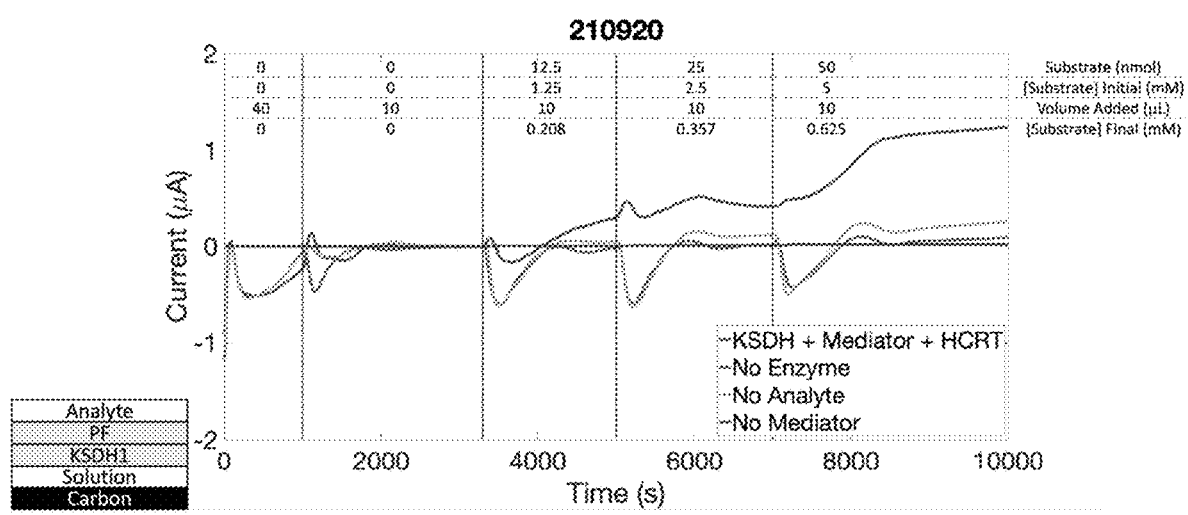
FIGS. 24A-B. A $2^{nd}$ generation cortisol biosensor with KSDH1 and PF in solution with enzyme, analyte, and mediator controls (FIG. 24A). There is some background signal without the presence of cortisol or enzyme. KSDH1 biosensor with no mediator showed a dose-responsive signal to cortisol (FIG. 24B). These data proved that a 3rd generation electrochemical biosensor can be engineered with KSDH1 and a carbon metal. These data suggested that the catalytic core of KSDH1 was close enough to the surface of enzyme where the electrode could pull electrons from the internal FAD cofactor of KSDH1 directly without the presence of a mediator with the application of the correct potential.
Figure 24B:
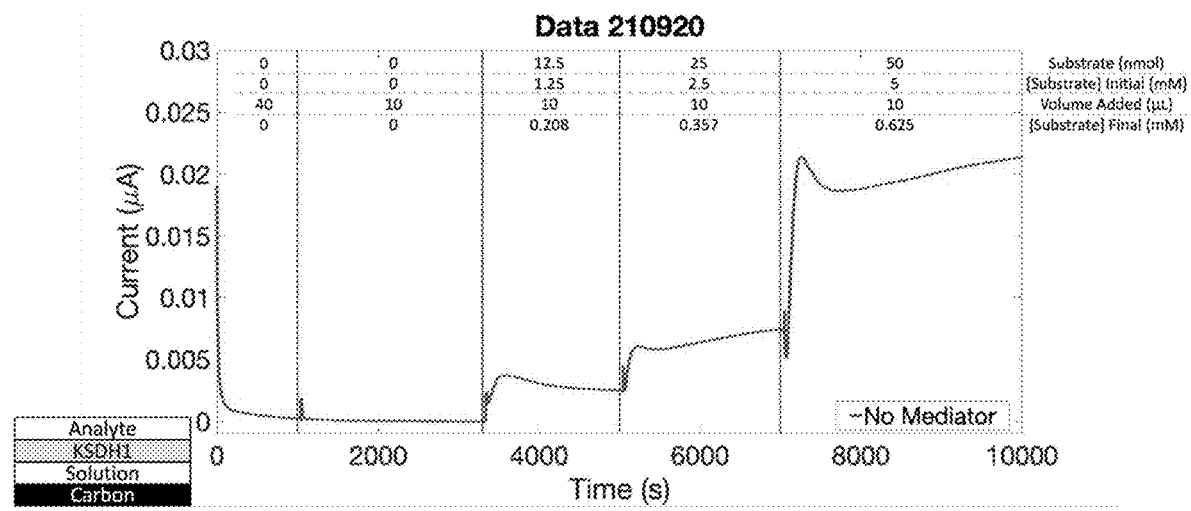
Figure 25A:
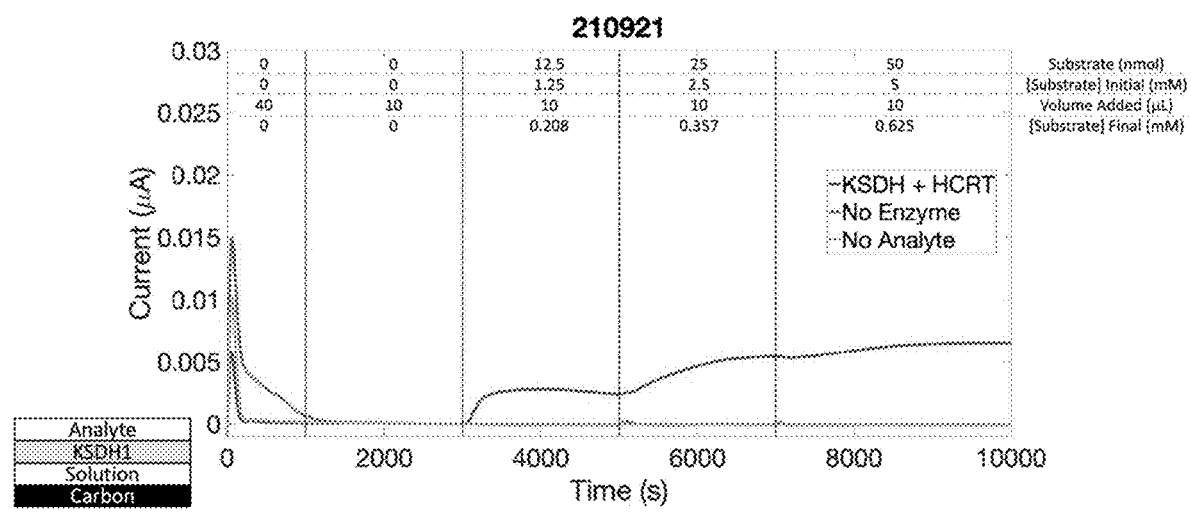
FIGS. 25A-B. $3^{rd}$ generation cortisol biosensor with KSDH1 in solution and controls (FIG. 25A). $3^{rd}$ generation glucose biosensor with GDH-FAD in solution and glucose (FIG. 25B).
Figure 25B:
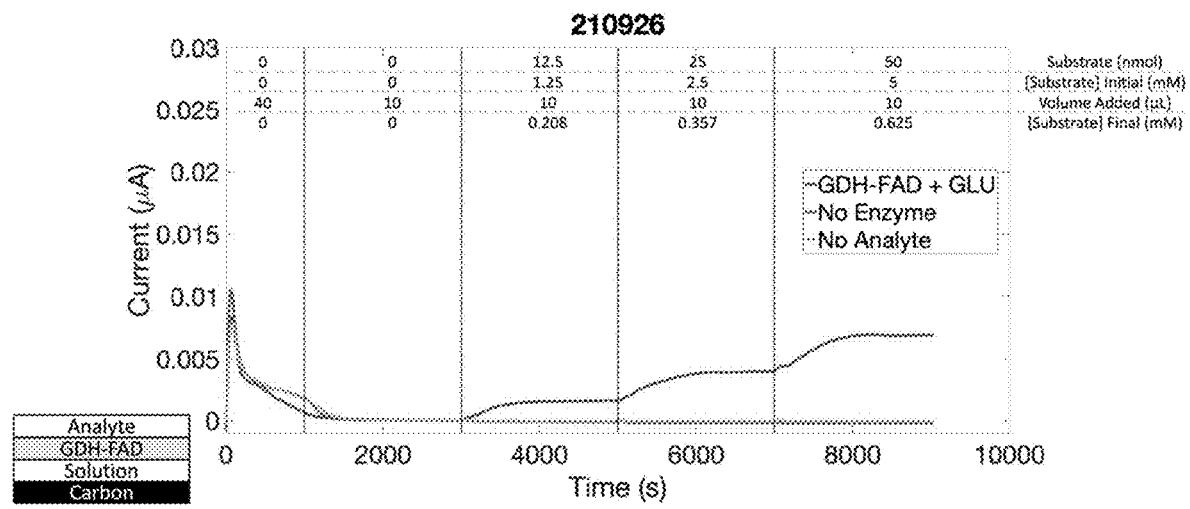
Figure 26A:
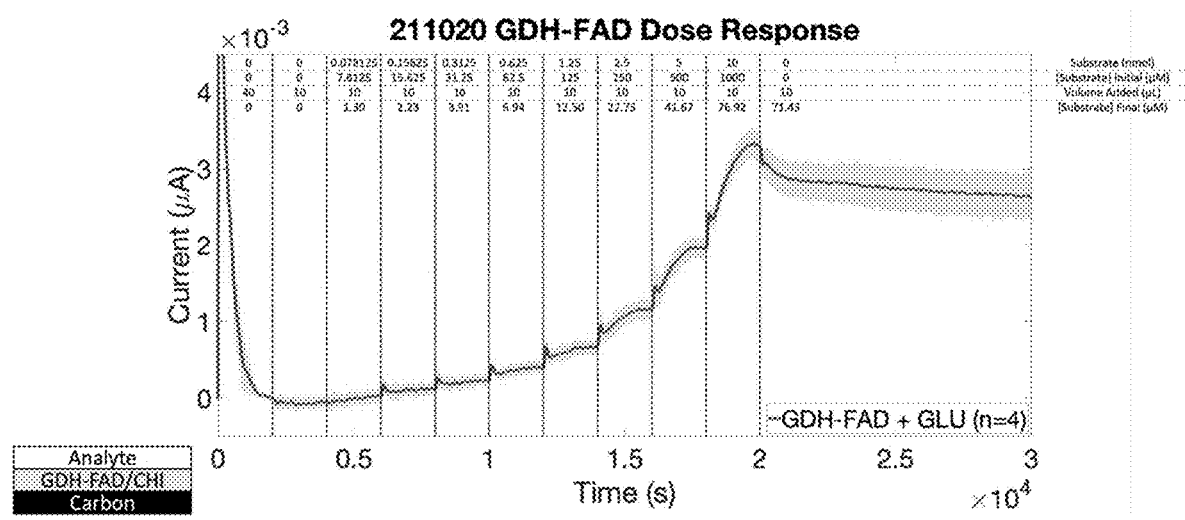
FIGS. 26A-C. $3^{rd}$ generation glucose biosensor glucose dose response using GDH-FAD deposited on a DS110 with chitosan and dried (FIG. 26A). Most of the signal is in low frequency domain (FIG. 26B). A lowpass filter removes noise in the signal (FIG. 26C).
Figure 26B:
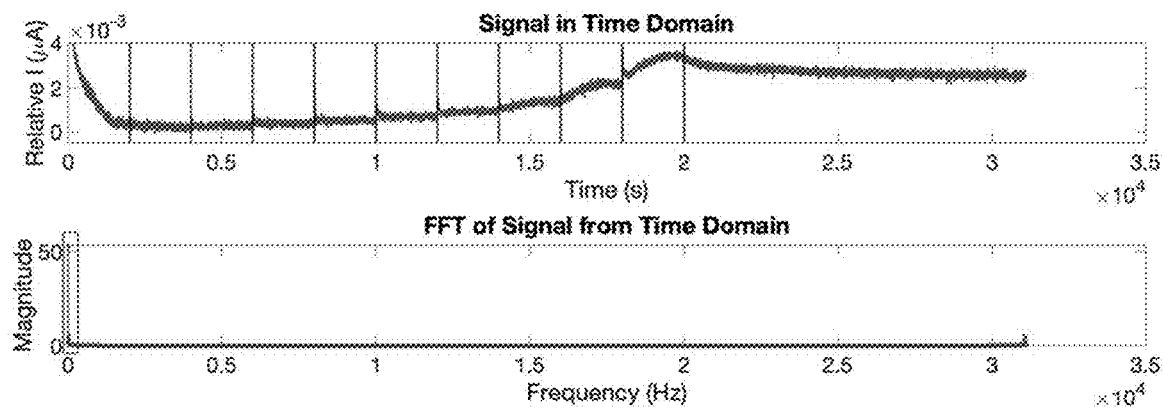
Figure 26C:
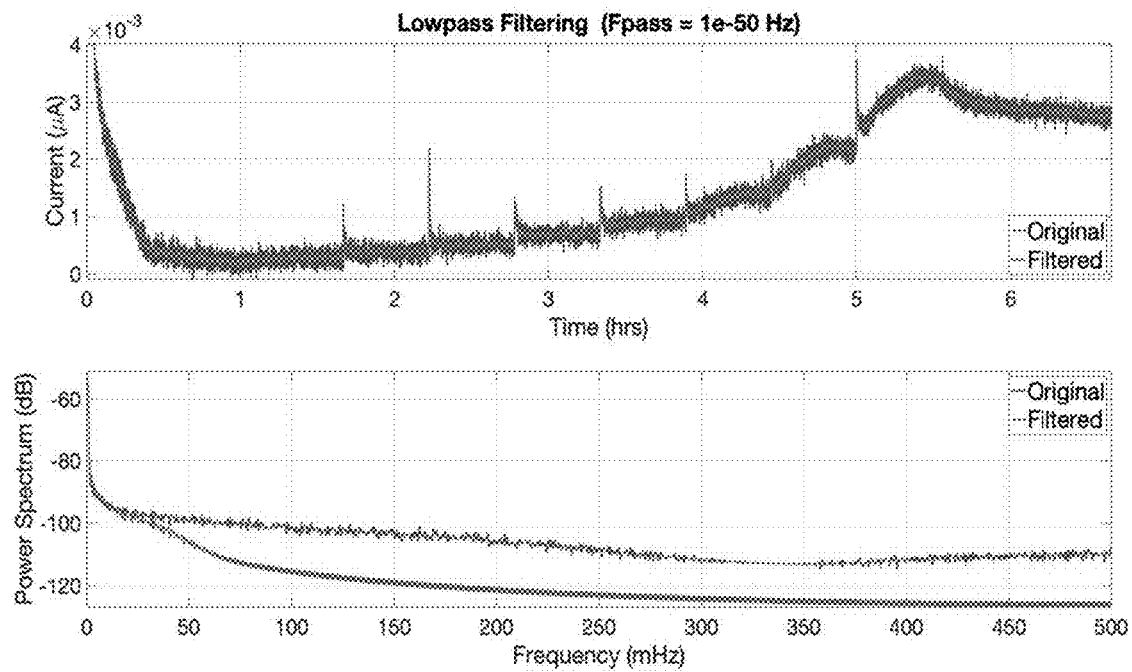
Figure 27:
FIG. 27. KSDH1 precipitation in the presence of chitosan, an immobilizing polymer, is evident.
Figure 28:
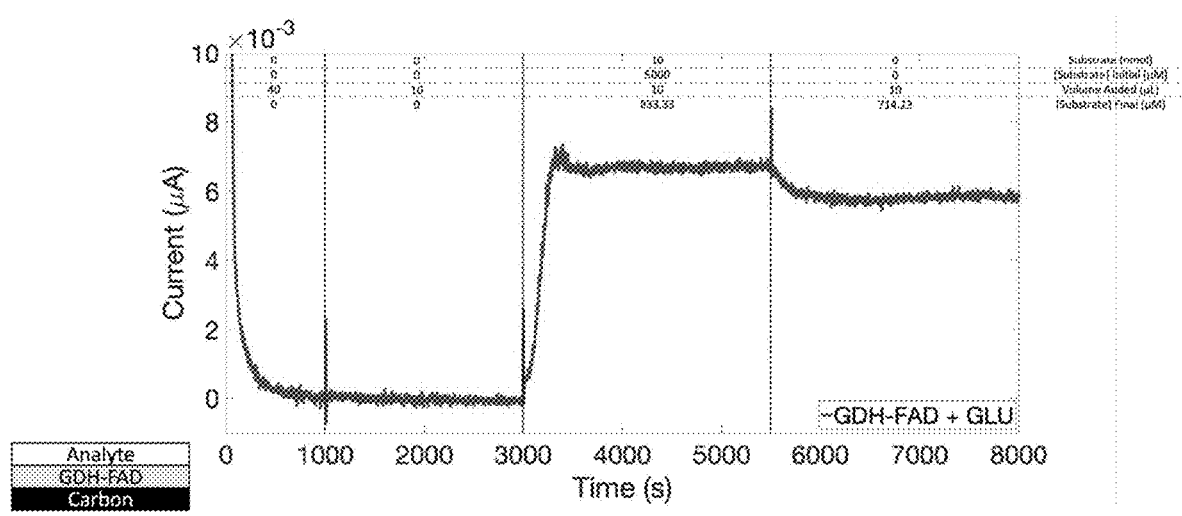
FIG. 28. $3^{rd}$ generation glucose biosensor using GDH-FAD deposited on a DS110 without chitosan demonstrating that a current can be generated in a dose-responsive fashion without immobilization.
Figures 29, 30A:
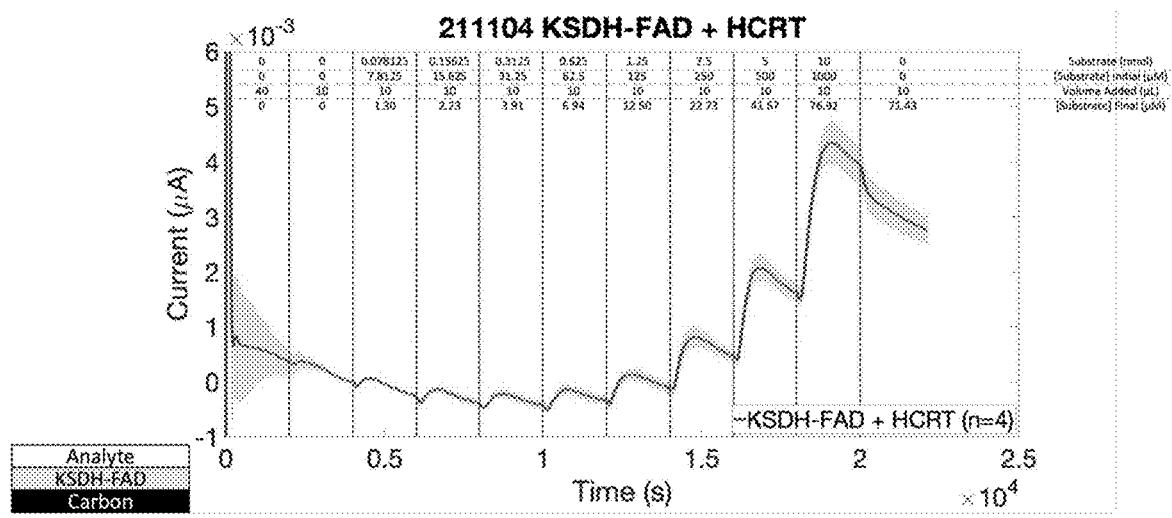
FIGS. 29. $3^{rd}$ generation cortisol biosensor cortisol dose response using KSDH1 deposited and dried on a DS110.
FIG. 30A-B. Glutaraldehyde immobilization decreases signal (FIG. 30A). KSDH1 has no change in current output after storage at 4 C for 1 week (FIG. 33A); Two electrode (2E) configuration, DS110, +0.4V; CH1: 10 µL KSDH1 400 µM (H2O); CH2: 5 µL KSDH1 400 µM (H₂O)+5 µL 0.1% Gluteraldehyde; CH3: 10 µL KSDH1 400 µM (H₂O)+10 µL 0.1% Gluteraldehyde; CH4: 10 µL KSDH1 400 µM (H₂O). Cortisol calibration curve calculated from FIG. 30A CH4 demonstrating that the biosensor can detect cortisol in quantitative and linear fashion (FIG. 30B).
Figure 30B:
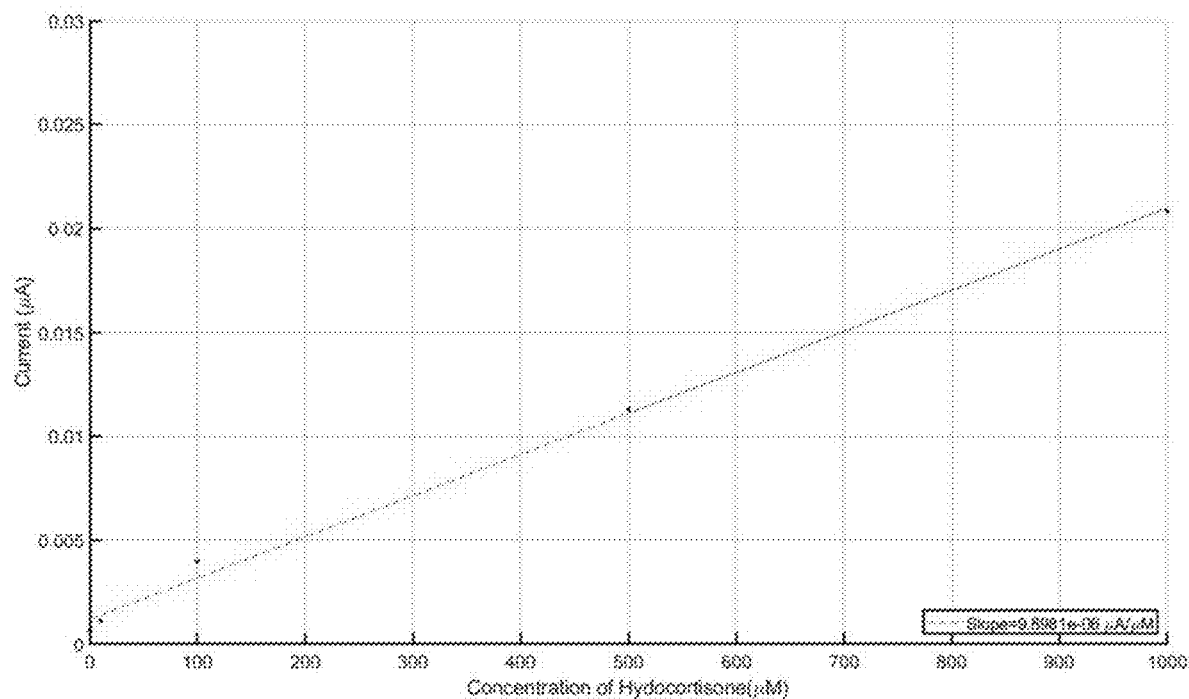
Figure 31:
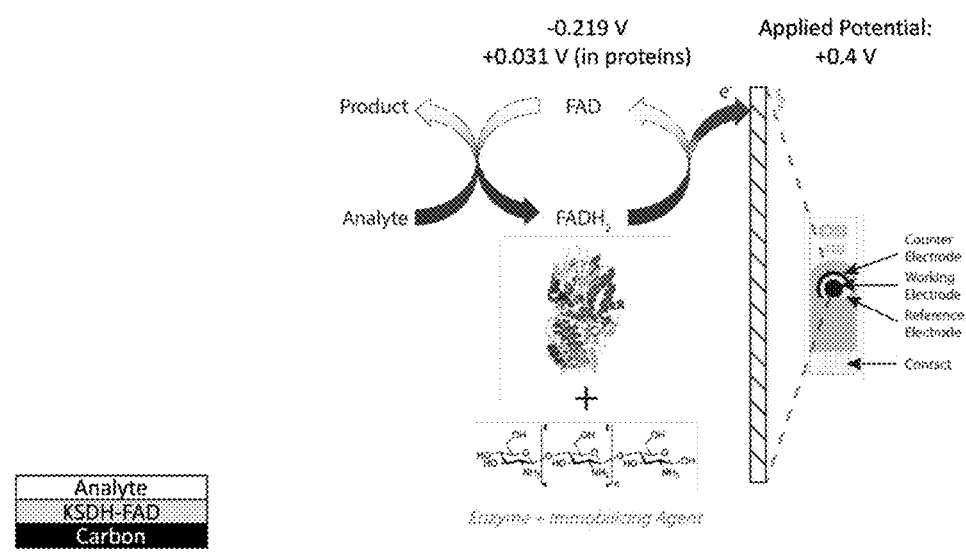
FIG. 31. Graphic of the $3^{rd}$ generation electron flow mechanism using a dehydrogenase and a carbon working electrode (DS110).
Figures 32A, 32B:
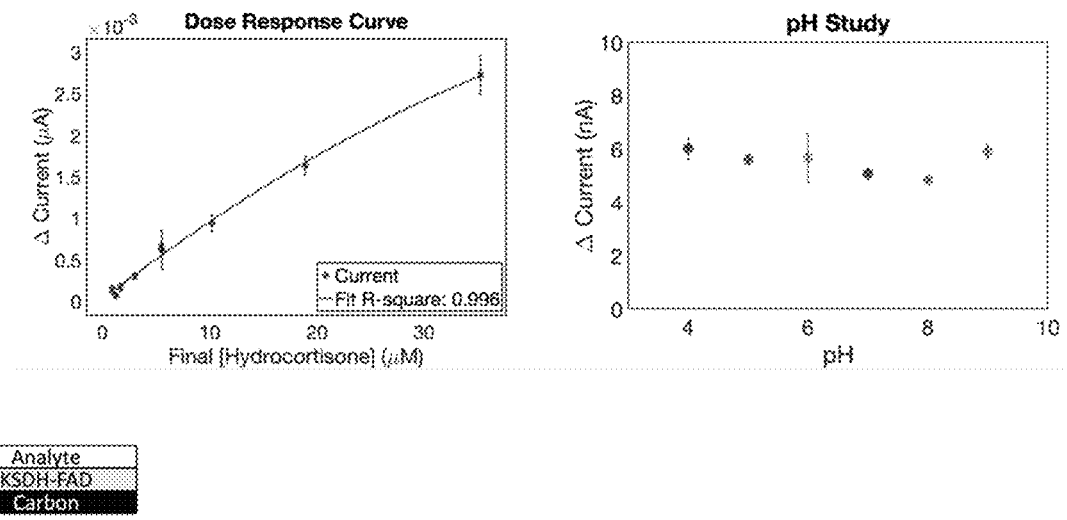
FIGS. 32A-B. Dose response curve for cortisol (FIG. 32A), and pH study (FIG. 32B).

The FAD-binding (KSDH1) enzyme was used to develop and optimize a hormone electrochemical biosensor. From an electrochemical biosensor perspective, KSDH1 catalyzes hormones, e.g. progesterone and cortisol, and results in FAD reduction, where potential can be applied to strip the cofactor electrons directly enabling quantitative detection of the amount of hormone in solution. The KSDH1 was assessed using the Amplex® UltraRed Assay™ for $H_2O_2$ detection by signal, hormones in the presence of KSDH1 were associated with an increase of fluorescence for progesterone and hydrocortisone (see e.g., FIG. 6B). KSDH1 was also assessed using a DCPIP Assay to test whether it is a dehydrogenase. In the presence of hydrocortisone, progesterone and KSDH1, DCPIP was reduced resulting in the decrease of absorbance at OD600 nm (see e.g., FIG. 9B).

In order to develop a biosensor, KSDH1 was immobilized onto an IDE (DropSens™) platinum working (WE) and reference (RE) electrodes, and the electrode was connected to a DropSens μSTAT4000P (Metrohm USA™, Riverview, Fla.) potentiostat (analogous potentiostat circuit e.g., FIG. 7).

An enzymatic biosensor for the detection and quantification of hormones from samples, such as human bodily fluids, was developed. The enzyme or sensing element comprises a 3-ketosteroid-Δ1-dehydrogenase present in *Pimelobacter simplex*. RNA-Seq on *P. simplex* in the presence and absence of hormone identified KSDH1 as a 3-ketosteroid-Δ1-dehydrogenase enzyme. Experimental data with KSDH1 demonstrated the conversion of progesterone and cortisol to product. Immobilization of KSDH1 on an interdigitated electrode produced a device that linearly responded to hormone with production of electrons for chronoamperometric measurement. The device quickly and accurately determined the concentration of hormone in urine with the same precision and accuracy as linear ion trap mass spectrometer. This hormone POC detection device can used in a clinical setting. Finally, the strategy of using metagenomic sequence mining can be used to further identify new redox enzymes for analytes of clinical relevance, especially given the diversity of microbes available for screening.

Example 2

Optimization of the Hormone Biosensor

The inventors herein optimized multiple parameters of the hormone biosensor to enable it to be used for real-time measurements of hormone, to enable it be sensitive to physiological levels of hormone in serum and sweat, as well as enable repeated detection of hormone in a variety of different samples. Table 1 lists commonly determined physiological levels of hormone in serum and sweat.

TABLE 1

Common physiological hormone concentrations.

| Compound | Serum (nM) | Sweat (nM) |
|---|---|---|
| Cortisol | 55.18-772.5 | 22.51-390.9 |
| Testosterone | 0.52-37.1 | 62.41-5794 |
| Melatonin | 0.0086-0.043 | 0.3147-1.1671 |
| Aldosterone | 5.55-27.75 | |
| Estradiol | 0.037-1.29 | 49.93-90.3 |
| Estrone | 0.026-0.74 | |
| Epinephrine | ≤0.77 | |
| Norepinephrine | 0.41-10.05 | |
| Dopamine | <0.16 | |
| Lactate | 6E+5 – 2E+7 | 13.7E+6 – 78.5E+6 |
| Creatinine | 4.5E+4 – 1.5E+5 | 14E+3 – 48E+3 |

(ii) Working Electrode Optimization

The hormone biosensor with three electrodes (a working electrode, a counter electrode and a reference electrode) and a biosensor with two electrodes (2E), i.e., a working electrode and a reference electrode, are effective in detecting hormone. As such, unlike typical electrochemical sensors such as those for glucose oxidase that comprise three electrodes, a hormone biosensor disclosed herein may be optimized to comprise only two electrodes preventing signal drift and reducing signal noise.

(iii) Surface Area

Figure 33A:
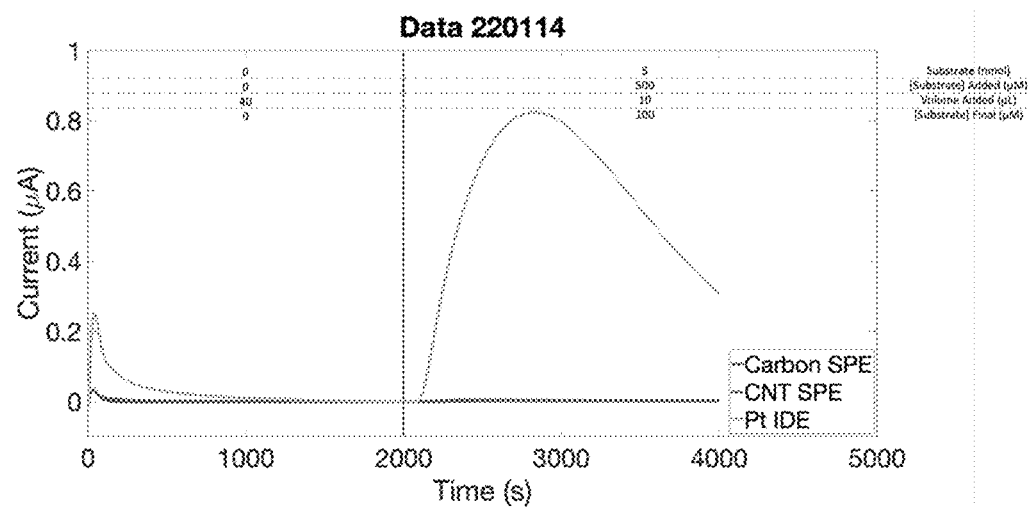
FIGS. 33A-H. Platinum interdigitated electrodes (IDEs) produce 2 logs more current than carbon and carbon with carbon nanotube (CNT) SPEs (FIG. 33A), and (FIG. 33B) and (FIG. 33C) (maximum current during amperometric detection of 100 µM cortisol). Platinum IDE controls produce no response (FIG. 33D-E). Improved sensitivity with platinum IDEs (FIG. 33F), by depositing more enzyme layers (FIG. 33G), and using different IDE geometries (FIG. 33H).
Figure 33B:
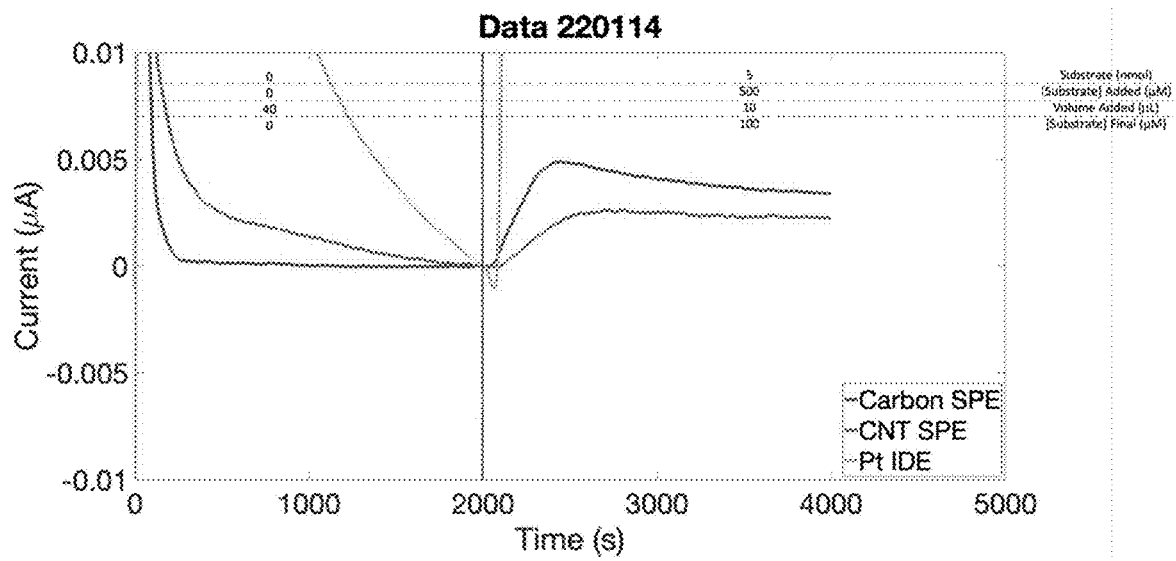
Figure 33C:
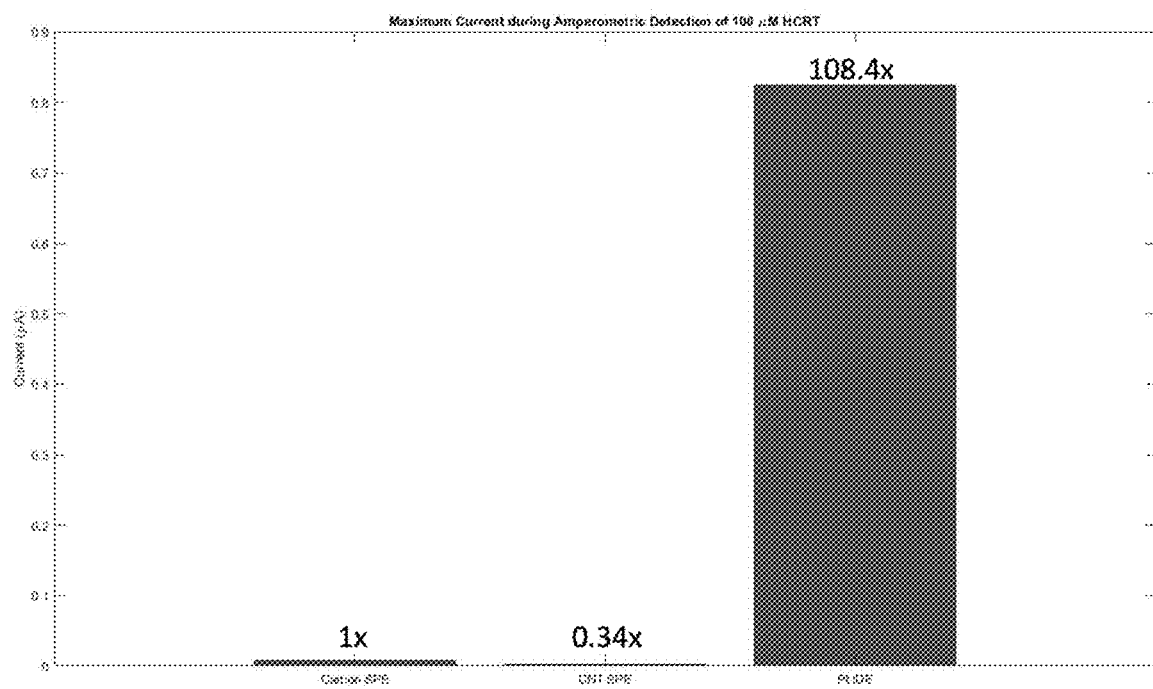
Figure 33D:
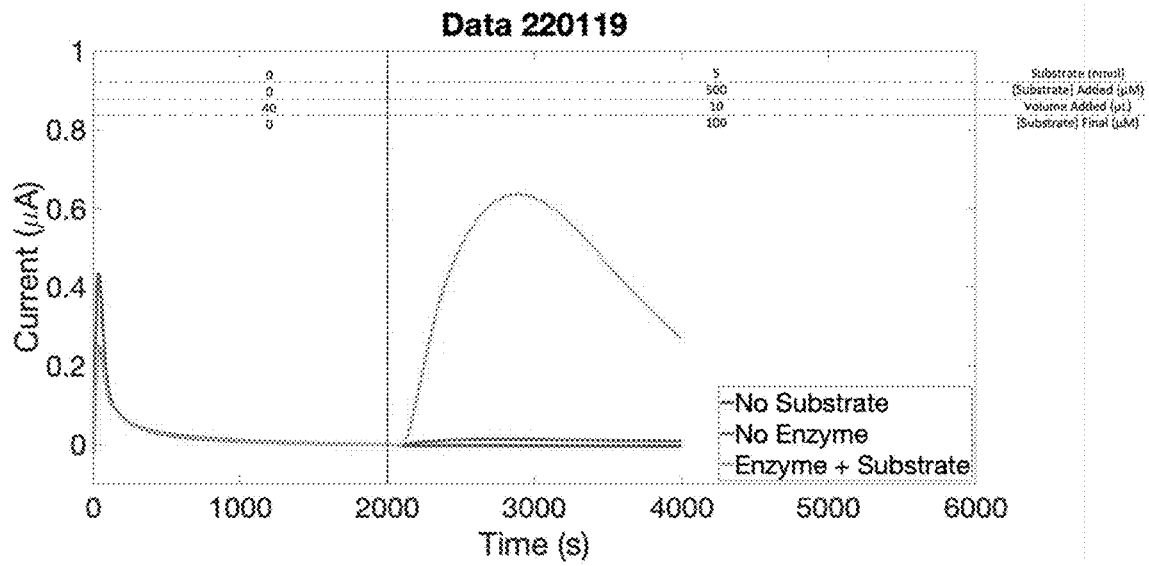
Figure 33E:
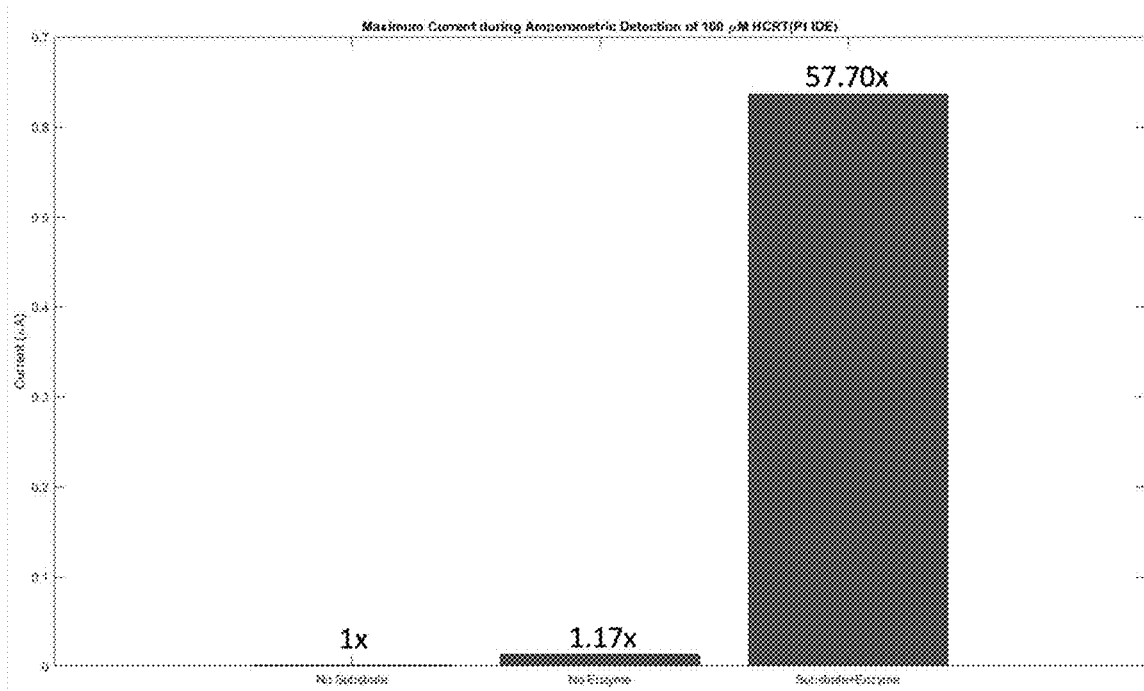
Figure 33F:
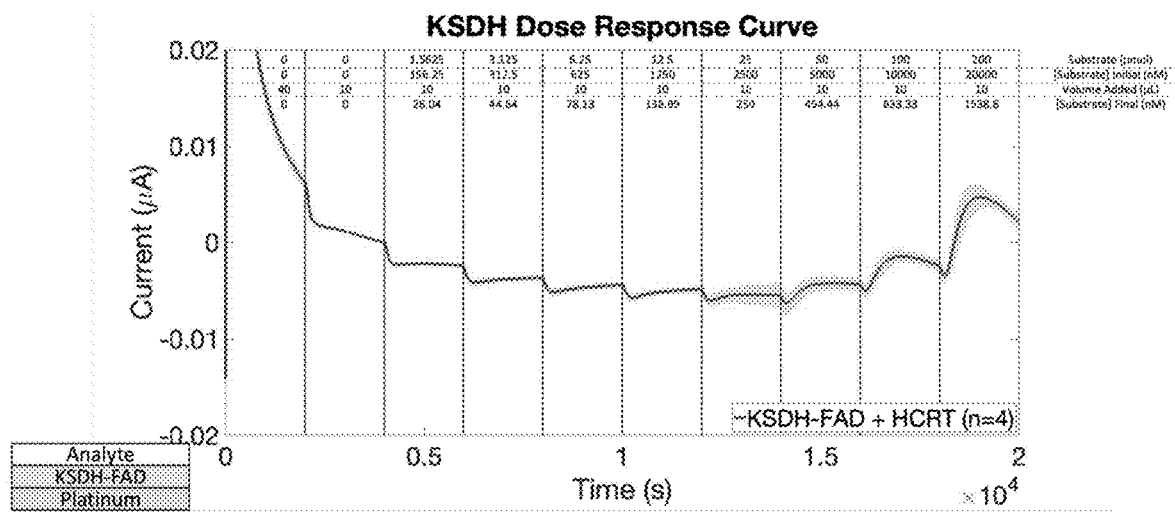
Figure 33G:
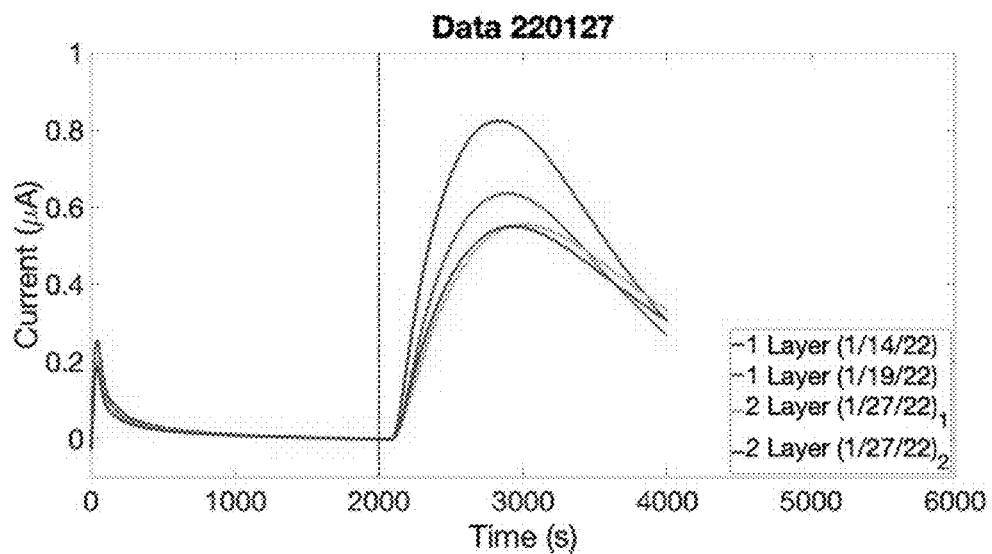
Figure 33H:
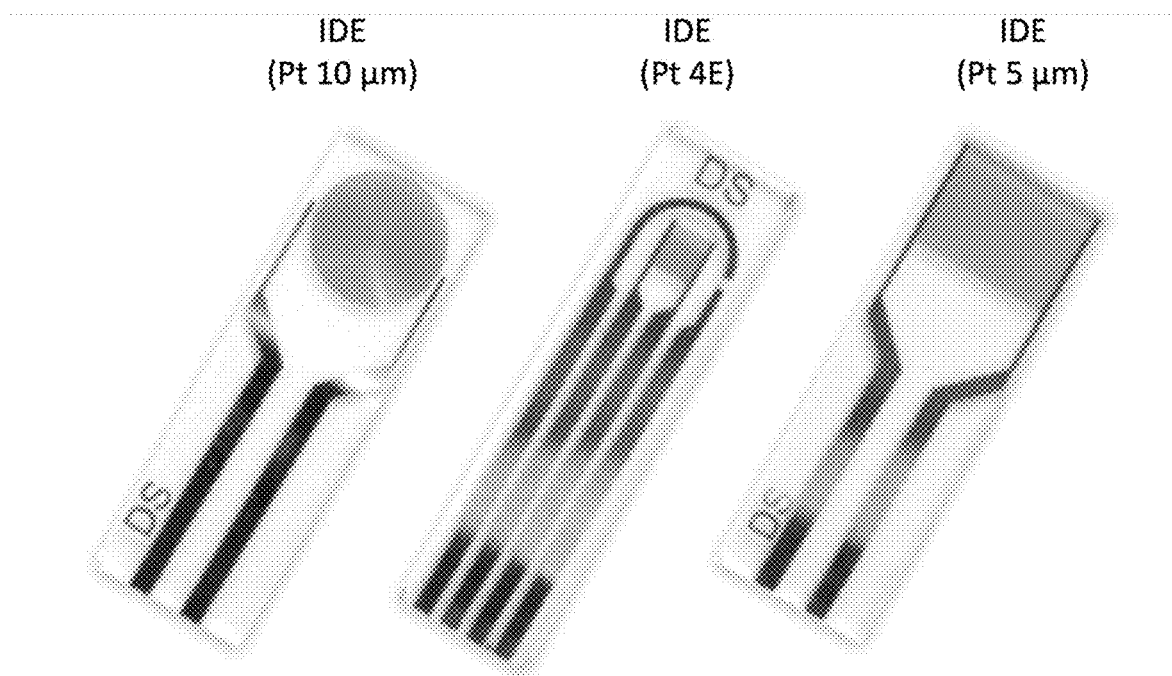
Figure 34:
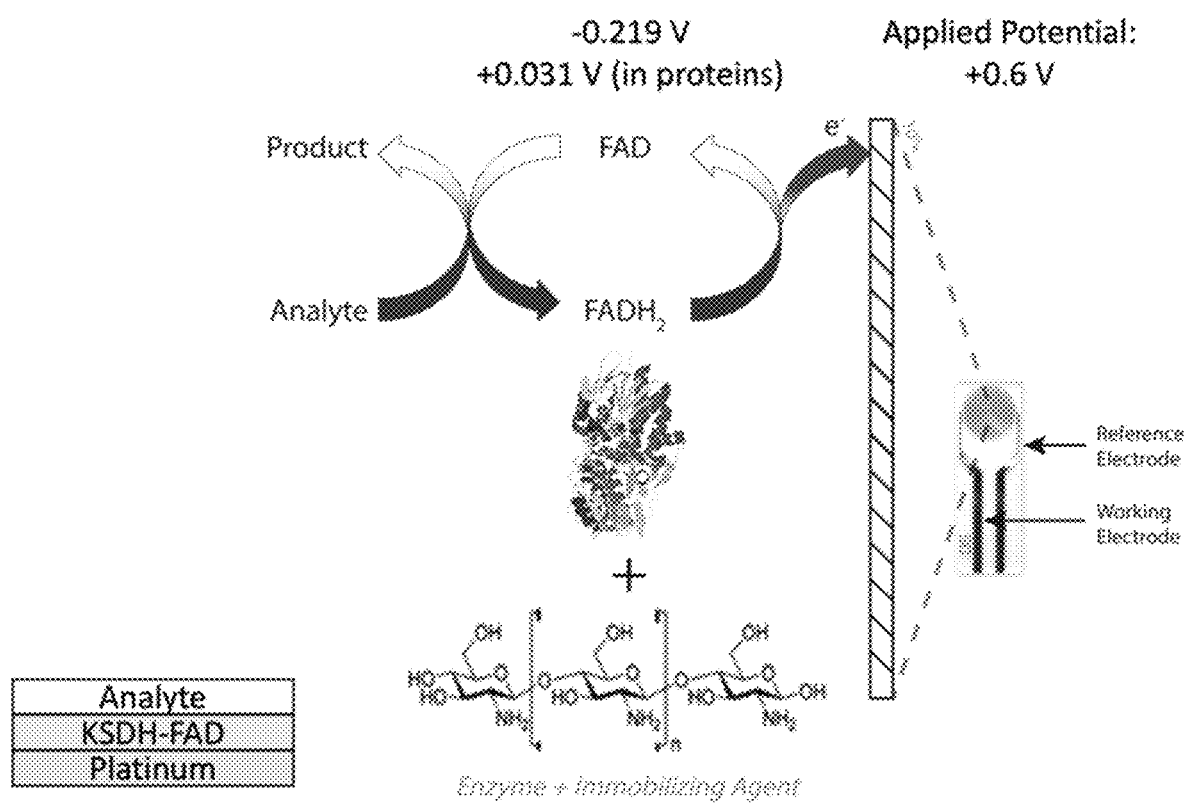
FIG. 34. Illustrates a $3^{rd}$ generation electron flow mechanism using platinum IDEs.
Figure 35A:
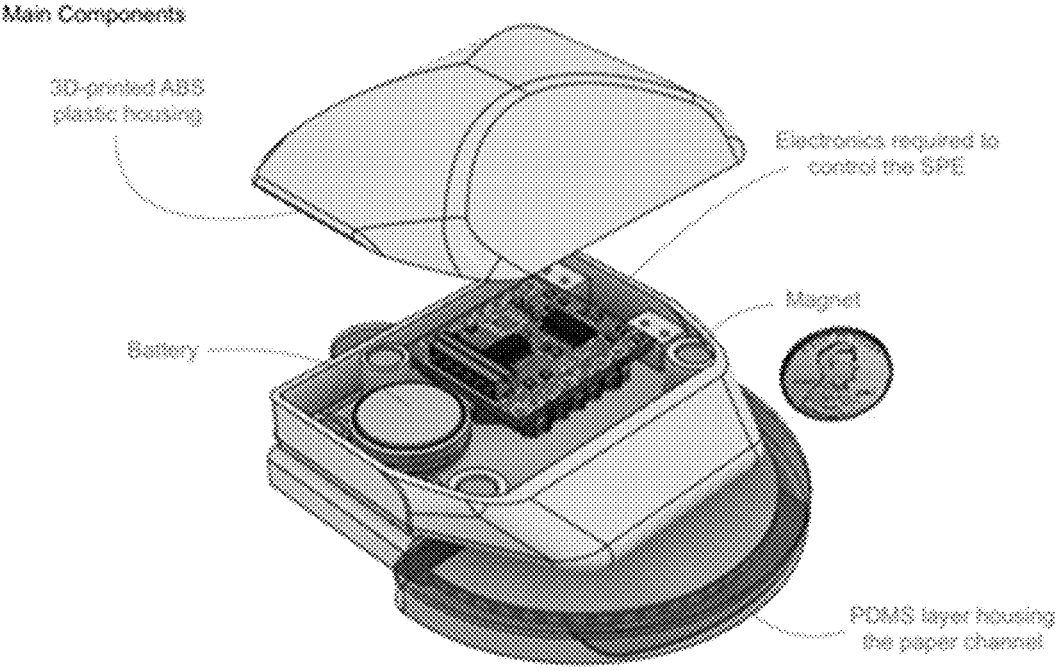
FIGS. 35A-35B. Illustrate a wearable device (FIGS. 35A-35B) which allows for the measurement of hormones continuously, quantitatively, and in real-time by integration of the described biosensor.
Figure 35B:
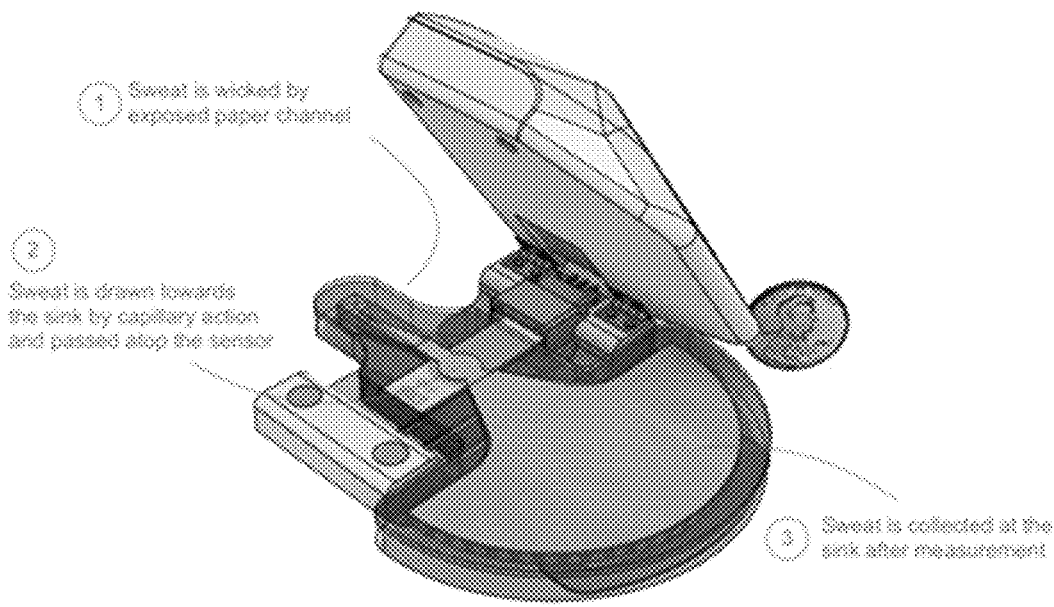

In addition, a larger surface area of the electrode resulted in the greatest preservation in current. Accordingly, a working electrode that has an area of >11π mm² results in current preservation; it may be a demonstrated efficient current detection with an electrode of 11π mm². In some embodiments, the size of the working electrode is in the range of 5-8π mm², or 8-10π mm², or 10-12π mm², or 12-15π mm², or greater than 15π mm². Interdigitated electrodes of 10 μm and 5 μm spacing were tested. As shown in FIG. 33H, electrodes with different shapes and spacing were assessed, and a circular or oval working electrode shape was sufficient for current preservation.

Example 3

Development of the KSDH1 2-Electrode Hormone Biosensor into a Wearable Biosensor.

Accordingly, a wearable hormone biosensor device may be developed, where the wearable hormone biosensor comprises the KSDH1 enzyme immobilized on a surface of a working electrode of a 2-electrode hormone biosensor. One exemplary wearable biosensor can comprise an upper housing and a lower chamber, where the upper housing can comprise a removable lid and be configured to comprise the electrical circuit and other necessary components, e.g., battery etc. The electrical circuit can be configured to be in electronic communication with one of more of the electrodes on a screen printed electrode (SPE) or interdigitated electrode (IDE), which is located in the chamber below the upper housing. In one embodiment, the lower chamber comprises a sink for collecting sweat or interstitial fluid after it has passed over the working and/or reference electrode of the SPE or IDE by capillary action. For example, in one embodiment, the lower chamber comprises a SPE or IDE comprising a 2-electrode system, which is in fluid communication with a wick, where the wick can be a paper channel that, at the proximal end contacts the surface of a subjects' skin and at the distal end contacts the chamber sink, so that as sweat or interstitial fluid moves from the proximal to the distal end of the wick (or paper channel) by capillary action it passes over at least the working electrode of the SPE or IDE. The amount of hormone in the sweat or interstitial fluid can be measured by the KSDH1 enzyme on the working electrode in the SPE or IDE. The wick (or paper channel) can be readily replaced when saturated, and the SPE or IDE can be replaced after between 3-7 days. In some embodiments, the whole wearable hormone biosensor device is affixed to the skin of a subject.

It is envisioned that the wearable hormone biosensor comprising the KSDH1 enzyme exemplified herein can be readily adapted by one of ordinary skill in the art, including using an adhesive sheet to attach the wicking apparatus to the surface of the wearers skin, as disclosed in U.S. Pat. No. 9,820,692, or use of sweat collection pads as disclosed in U.S. Pat. Nos. 10,182,795 and 10,646,142, each of which are incorporated herein their entirety by reference.

Current physiological sensors on the market such as the Fitbit™ and Apple Watch™ are limited to the detection of pH, hydration, temperature, heart rate, UX index, oxygen, sleep health, and energy expenditure with limited accuracy and reproducibility. Presently, the single best example of a commercially successful enzymatic biosensor is the glucose biosensor which has existed for approximately 50 years and has in the past two decades evolved into the continuous glucose monitor (CGM; see e.g., Olczuk et al. Diabetes Metab Syndr 2018, 12 (2), 181-187). By 2004, the glucose biosensor was responsible for about 85% of the world market for biosensors, estimated to be $5 billion USD at the time. By 2015, the market for glucose biosensors was valued at $15.3 billion USD and is expected to surpass $31 billion USD by 2024 per Hexa Research. The glucose monitor's functionality is based on the isolation and use of a glucose oxidase ($GO_X$) enzyme from *Aspergillus niger*, a fungus. Specifically, the ability of $GO_X$ to produce $H_2O_2$ from β-D-glucose and oxygen has been used to engineer the first glucose biosensor in an electrochemical fashion. With a mediator and a three-electrode system, $H_2O_2$ generated from $GO_X$ in response to β-D-glucose, along with a constant electrical potential, produces current which can be used as a readout for the amount of β-D-glucose present in solution.

Even with the immense commercial success of the glucose biosensor, comparable enzymatic biosensors have been limited. By 2007, commercially available enzyme based clinical tests could detect only glucose, lactate, choline, urea, uric acid, lysine, and oxygen. By 2008, amperometric based biosensors solely included those for glucose ($GO_X$), fructose (FDH), lactate ($LO_X$), glutamate ($LGO_X$), lysine (LDH), ethanol (ADH), and morphine (MDH) (see e.g., Dzyadevych et al. Irbm 2008, 29 (2-3), 171-180). The reason for the lack of a wide variety of biosensors is primarily due to two reasons. Of the seven biosensors listed, few have daily physiological relevance. The exception is the glucose biosensor due to diabetes affecting 382 million people and being the $8^{th}$ leading cause of death worldwide by 2013 which naturally created a large market and need for such a sensor. The second reason is that the current largest scientific vendors, such as Sigma-Aldrich™, have a limited inventory of enzymes such as $GO_X$, $LO_X$, FDH, $LGO_X$, and ADH with little intention of investing resources to provide new electrochemically relevant ones.

In response to the lack of electrochemical biosensors, biorecognition elements may be obtained from a source of bacteria. Bacteria have evolved over 3 billion years to detect and respond to virtually all classes of stimuli relevant to human physiology, and thus contain molecular sensing enzymes of interest. Using a combination of whole transcriptome RNA sequencing (RNA-Seq) and a functional screen (Amplex® UltraRed Assay), biosensing enzymes have been identified and isolated, including KSDH1. These redox enzymes can be used in biosensors, and the development of small, easy to use, and cheap electrochemical biosensors, which started from bacterial cultures for physiologically relevant analytes. These biosensors are typically composed of a screen-printed electrode (SPE), interdigitated electrode (IDE), electron mediator (e.g. Prussian Blue), and a redox enzyme. This pipeline was used to build an enzyme-based electrochemical hormone biosensor.

Existing biosensor designs outside of electrochemical ones have noticeable limitations. The most common design utilizes a biorecognition element coupled to a physicochemical transduction mechanism (see e.g., Turner, A., Trends in Biotechnology 2013, 31 (3), 119-120; Mary et al., Measurement Science and Technology 2014, 25 (3), 032001; Evtugyn, G., Biosensors: Essentials. Springer: 2014; Vol. 84). The gold standard for clinical relevant analytes use antibodies as this biorecognition element. However, antibodies suffer from several important shortcomings: 1) Traditionally, antibody production requires animal immunization followed by monoclonal isolation and is expensive, highly variable, time consuming, and challenging with small molecule analytes (see e.g., Mary et al. 2014, supra). More recent recombinant techniques simplify this process and improve reproducibility, but the process remains expensive due to the use of mammalian cell lines or heterologous hosts (see e.g., Frenzel, et al. Frontiers in immunology 2013, 4, 217; Hornsby et al. Molecular & cellular proteomics: MCP 2015, 14 (10), 2833-47). 2) Binding of the analyte to the antibody leads to only a small physicochemical change, requiring the use of a secondary assay to detect the binding event (see e.g., Mary et al. 2014, supra; az-Gonzale et al. Electroanalysis 2005, 17 (21)). Enzyme-linked immunosorbent assays (ELISAs) are the most common transduction approach and are multistep, labor-intensive, time-consuming, and not well-suited for integration into wearable technology (see e.g., az-Gonzale et al. 2005, supra). More recently, aptamers have been studied as an alternative to antibodies, but also lack an intrinsic transduction mechanism (see e.g., Mary et al. 2014, supra; Marrazza, G., Aptamer Sensors. Biosensors (Basel) 2017, 7 (1)). Due to these limitations, non-electrochemical biosensors often are suboptimal design choices for physiological monitoring.

REFERENCES

All references and publication cited in the specification and Examples are incorporated herein in their entirety by reference, including the following.

1. Ferri, S., et al., Review of glucose oxidases and glucose dehydrogenases: a bird's eye view of glucose sensing enzymes, 2011, SAGE Publications.

2. Tsuruoka, N., et al. (2017). "Bimolecular rate constants for FAD-dependent glucose dehydrogenase from *Aspergillus terreus* and organic electron acceptors." International Journal of Molecular Sciences 18(3): 604.
3. Loew, N., et al. (2017). "Mediator preference of two different FAD-dependent glucose dehydrogenases employed in disposable enzyme glucose sensors." Sensors 17(11): 2636.
4. Roberts, James G., Keri L. Hamilton, and Leslie A. Sombers. "Comparison of electrode materials for the detection of rapid hydrogen peroxide fluctuations using background-subtracted fast scan cyclic voltammetry." Analyst 136.17 (2011): 3550-3556.

We claim:

1. A biosensor for measuring a concentration of a hormone, comprising:
an electrode comprising a surface; and
a recombinant 3-ketosteroid-Δ1-dehydrogenase enzyme 1 (KSDH1) deposited on the surface of the electrode, wherein the KSDH1 enzyme catalyzes the hormone to produce an electrochemical signal, wherein the KSDH1 enzyme comprises an amino acid sequence that is at least 90% identical to SEQ ID NO:2.

2. The biosensor of claim 1, wherein the hormone is hydrocortisone or progesterone.

3. The biosensor of claim 1, wherein the KSDH1 enzyme comprises an internal enzyme cofactor flavin adenine dinucleotide (FAD).

4. The biosensor of claim 1, wherein in the presence of the hormone, the biosensor is configured such that the KSDH1 enzyme reduces an internal enzyme cofactor that releases electrons to produce the electrochemical signal, wherein the electrochemical signal is detected by current passed to the electrode.

5. The biosensor of claim 4, wherein in the presence of the hormone, the biosensor is configured such that the KSDH1 enzyme oxidizes the hormone and the internal enzyme cofactor of the KSDH1 enzyme becomes reduced, wherein an oxidized mediator ($Med_{ox}$) then strips the electrons from the internal enzyme cofactor to become a reduced mediator ($Med_{red}$), and wherein electrons are then stripped from the $Med_{red}$ by the electrode in the presence of an applied potential to produce a current signal and regenerate the $Med_{ox}$, allowing another reaction to occur.

6. The biosensor of claim 1, further comprising an electronically active mediator (Med) deposited on the surface of the electrode.

7. The biosensor of claim 1, wherein the biosensor is an amperometric biosensor, a voltammetric biosensor, an electrochemical impedance biosensor, or a potentiometric biosensor.

8. The biosensor of claim 1, wherein the electrode is connected to a potentiostat having a current resolution to at least 1 pA (100 nA range).

9. The biosensor of claim 1, wherein the biosensor comprises a working electrode and a reference electrode.

10. The biosensor of claim 9, wherein an area of the working electrode is greater than 10 mm².

11. The biosensor of claim 1, wherein the electrode is either metallic or non-metallic.

12. The biosensor of claim 1, wherein the electrode is platinum.

13. The biosensor of claim 1, wherein the electrode is non-metallic and comprises carbon.

14. The biosensor of claim 1, wherein the biosensor is a chronoamperometric biosensor.

15. A method of using a biosensor to measure a concentration of a hormone, comprising:
a. providing the biosensor of claim 1;
b. providing a sample; and
c. measuring a current produced by an oxidation of the hormone in the sample.

16. The method of claim 15, wherein the hormone is hydrocortisone or progesterone.

17. The method of claim 15, wherein in the presence of the hormone, the KSDH1 enzyme reduces an internal enzyme cofactor that releases electrons to the electrode in the presence of a potential to produce the electrochemical signal, wherein the electrochemical signal is detected by the current passed to the electrode.

18. The method of claim 15, wherein the biosensor is an amperometric biosensor.

19. The method of claim 15, wherein the biosensor comprises a working electrode and a reference electrode.

20. A wearable electrochemical hormone biosensor device comprising:
an electroconductive part comprising a housing containing an electric control circuit;

a working electrode comprising a surface; and a recombinant 3-ketosteroid-Δ1-dehydrogenase enzyme 1 (KSDH1) deposited on the surface of the working electrode, wherein the KSDH1 enzyme comprises an amino acid sequence that is at least 90% identical to SEQ ID NO:2.

21. The wearable hormone biosensor device of claim 20, wherein the biosensor device is electrically connected to a potentiostat, wherein the potentiostat is linked to at least the working electrode of the biosensor device, and the working electrode is in fluid communication with a wicking paper configured to wick sweat or interstitial fluid from a surface of skin of a subject.

22. The wearable hormone biosensor device of claim 20, wherein when attached to skin of a human subject, the biosensor device is configured to detect an amount of the hormone in sweat or interstitial fluid of the human subject, in a real time, quantitative and chronoamperometric manner.

* * * * *

SEQUENCE LISTING

```
<160> NUMBER OF SEQ ID NOS: 2

<210> SEQ ID NO 1
<211> LENGTH: 1570
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggactggg cagaagagta tgatgtgttg gtagctggat ccggtgctgg cggtatggct      60
gggacctata cggcagcgcg tgagggtctg tccgtatgtc tggtagaggc tggggacaaa     120
tttggaggca ctactgcata ctcaggcgga gggggagcgt ggtttcctgc aaatccggta    180
ctgttgcgtg cgggaaccga tgacaccatc gaggatgccc tggagtatta tcgtgctgta    240
gttggtgacc gtaccccggc tgacttgcaa gaaacctacg tacgcggggg agctgggttg    300
gtcgcctatt tggaggagga tgaccatttt tcgtttgaat cgtacccatg gcctgattat    360
tttggcgacg cccctaaggc ccgtcgtgac ggtcagcgtc atattattcc cacacccctg    420
ccggtacccc cagccccgga gttgcgcgaa gtagttcgtg gtcctttgga taatgatcgt    480
ttgggaaccc ctcaacccga tgacctgttc atcggcggac gtgccttagt tgcccgtttt    540
cttactgcct tagctaccta cccgcacgca actctggtcc gtgagactgc tttagcagag    600
cttgtggttg aggacggggt agtagtgggg gccattgtag aaaccgacgg cgtccgccgt    660
gccattcgcg cacgccgtgg tgtactgctt gcagctgggg gttttgaggc caatgacgaa    720
ttacgtcaga gtatggagt gccaggagta gcccgcgaca caatgggacc ccccacgaac    780
gttggcgcag cgcatcaggc ggccatcgcc gttggcgctg ataccgacct tatgggtgag    840
gcctggtggt cgcctggact gacacatcct gacgacgtt ctgcatttgc gctgtggttc    900
acgggaggaa tttttgttga tggagcaggt cgtcgttttg taaatgagtc cgccccatac    960
gatcgcctgg gtcgtgctgt tattgaccac ttaacagagg gaggcgtaac cccccgttat    1020
tggatggttt acgaccataa agagggctcc attcccctg tacgtgcgac taacgtaagt    1080
atggtggacg aggaacaata tgtagcagct ggactgtggc acacggcaga caccttcct    1140 gagcttgctg ctttaatcgg tgtccccgct gatgctcttg tggcgaccgt agcccgtttc    1200
aatgaacttg ttgcggatgg ctacgatgcg gattttggtc gcggggcga agcgtatgat    1260 cgcttcttt ctggagggga acctccatta gtatcaattg acgaaggtcc cttccacgcg    1320
gccgcatttg gaatctctga tttgggtaca aagggaggct tacgcacgga tacctccgcc    1380
cgcgtattaa cagccgatgg gacgcccatt ggtggattgt atgcggctgg taacacgatg    1440
gccgcaccga gtggaaccac gtacccaggg ggcggaaatc cgatcggaac gtcgatgttg    1500
ttctcccacc ttgcagtgcg ccacatgggt accgaggacg cgcgcggttc gcaccaccac    1560
caccaccact                                                          1570
```

<210> SEQ ID NO 2
<211> LENGTH: 523
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Met Asp Trp Ala Glu Glu Tyr Asp Val Leu Val Ala Gly Ser Gly Ala
1               5                   10                  15

Gly Gly Met Ala Gly Thr Tyr Thr Ala Ala Arg Glu Gly Leu Ser Val
            20                  25                  30

Cys Leu Val Glu Ala Gly Asp Lys Phe Gly Gly Thr Thr Ala Tyr Ser
        35                  40                  45

Gly Gly Gly Gly Ala Trp Phe Pro Ala Asn Pro Val Leu Leu Arg Ala
    50                  55                  60

Gly Thr Asp Asp Thr Ile Glu Asp Ala Leu Glu Tyr Tyr Arg Ala Val
65                  70                  75                  80

Val Gly Asp Arg Thr Pro Ala Asp Leu Gln Glu Thr Tyr Val Arg Gly
                85                  90                  95

Gly Ala Gly Leu Val Ala Tyr Leu Glu Glu Asp Asp His Phe Ser Phe
            100                 105                 110

Glu Ser Tyr Pro Trp Pro Asp Tyr Phe Gly Asp Ala Pro Lys Ala Arg
        115                 120                 125

Arg Asp Gly Gln Arg His Ile Ile Pro Thr Pro Leu Pro Val Pro Ser
    130                 135                 140

Ala Pro Glu Leu Arg Glu Val Val Arg Gly Pro Leu Asp Asn Asp Arg
145                 150                 155                 160

Leu Gly Thr Pro Gln Pro Asp Asp Leu Phe Ile Gly Arg Ala Leu
                165                 170                 175

Val Ala Arg Phe Leu Thr Ala Leu Ala Thr Tyr Pro His Ala Thr Leu
            180                 185                 190

Val Arg Glu Thr Ala Leu Ala Glu Leu Val Val Glu Asp Gly Val Val
        195                 200                 205

Val Gly Ala Ile Val Glu Thr Asp Gly Val Arg Arg Ala Ile Arg Ala
    210                 215                 220

Arg Arg Gly Val Leu Leu Ala Ala Gly Gly Phe Glu Ala Asn Asp Glu
225                 230                 235                 240

Leu Arg Gln Lys Tyr Gly Val Pro Gly Val Ala Arg Asp Thr Met Gly
                245                 250                 255

Pro Pro Thr Asn Val Gly Ala Ala His Gln Ala Ala Ile Ala Val Gly
            260                 265                 270

Ala Asp Thr Asp Leu Met Gly Glu Ala Trp Trp Ser Pro Gly Leu Thr
        275                 280                 285

His Pro Asp Gly Arg Ser Ala Phe Ala Leu Trp Phe Thr Gly Gly Ile
    290                 295                 300

Phe Val Asp Gly Ala Gly Arg Arg Phe Val Asn Glu Ser Ala Pro Tyr
305                 310                 315                 320

Asp Arg Leu Gly Arg Ala Val Ile Asp His Leu Thr Glu Gly Gly Val
                325                 330                 335

Thr Pro Arg Tyr Trp Met Val Tyr Asp His Lys Glu Gly Ser Ile Pro
            340                 345                 350

Pro Val Arg Ala Thr Asn Val Ser Met Val Asp Glu Glu Gln Tyr Val
```

```
                355                 360                 365
Ala Ala Gly Leu Trp His Thr Ala Asp Thr Leu Pro Glu Leu Ala Ala
            370                 375                 380

Leu Ile Gly Val Pro Ala Asp Ala Leu Val Ala Thr Val Ala Arg Phe
385                 390                 395                 400

Asn Glu Leu Val Ala Asp Gly Tyr Asp Ala Asp Phe Gly Arg Gly Gly
                405                 410                 415

Glu Ala Tyr Asp Arg Phe Phe Ser Gly Gly Glu Pro Pro Leu Val Ser
            420                 425                 430

Ile Asp Glu Gly Pro Phe His Ala Ala Ala Phe Gly Ile Ser Asp Leu
            435                 440                 445

Gly Thr Lys Gly Gly Leu Arg Thr Asp Thr Ser Ala Arg Val Leu Thr
            450                 455                 460

Ala Asp Gly Thr Pro Ile Gly Gly Leu Tyr Ala Ala Gly Asn Thr Met
465                 470                 475                 480

Ala Ala Pro Ser Gly Thr Thr Tyr Pro Gly Gly Gly Asn Pro Ile Gly
                485                 490                 495

Thr Ser Met Leu Phe Ser His Leu Ala Val Arg His Met Gly Thr Glu
            500                 505                 510

Asp Ala Arg Gly Ser His His His His His His
            515                 520
```